(12) United States Patent
Chen et al.

(10) Patent No.: US 12,042,480 B2
(45) Date of Patent: *Jul. 23, 2024

(54) METHODS, AGENTS, AND COMPOSITIONS FOR THE TREATMENT OF ACUTE MYELOID LEUKEMIA

(71) Applicant: University of Cincinnati, Cincinnati, OH (US)

(72) Inventors: Jianjun Chen, Cincinnati, OH (US); Xi Jiang, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 9 days.

This patent is subject to a terminal disclaimer.

(21) Appl. No.: 17/699,793

(22) Filed: Mar. 21, 2022

(65) Prior Publication Data

US 2022/0211669 A1 Jul. 7, 2022

Related U.S. Application Data

(62) Division of application No. 16/608,083, filed as application No. PCT/US2018/000111 on Apr. 26, 2018, now Pat. No. 11,311,513.

(60) Provisional application No. 62/490,184, filed on Apr. 26, 2017.

(51) Int. Cl.
| | |
|---|---|
| *A61K 31/4025* | (2006.01) |
| *A61K 31/365* | (2006.01) |
| *A61K 31/4525* | (2006.01) |
| *A61K 31/5377* | (2006.01) |
| *A61K 31/55* | (2006.01) |
| *A61P 35/00* | (2006.01) |

(52) U.S. Cl.
CPC ........ *A61K 31/4025* (2013.01); *A61K 31/365* (2013.01); *A61K 31/4525* (2013.01); *A61K 31/5377* (2013.01); *A61K 31/55* (2013.01); *A61P 35/00* (2018.01)

(58) Field of Classification Search
CPC .............. A61K 31/4025; A61K 31/365; A61K 31/4525; A61K 31/5377; A61K 31/55
See application file for complete search history.

(56) References Cited

U.S. PATENT DOCUMENTS

| | | | | |
|---|---|---|---|---|
| 11,311,513 | B2 * | 4/2022 | Chen | ............... A61K 31/365 |
| 2007/0123491 | A1 | 5/2007 | Axelson et al. | |
| 2012/0322807 | A1 | 12/2012 | Sekiguchi et al. | |
| 2013/0156795 | A1 | 6/2013 | Iavarone | |
| 2016/0031854 | A1 | 2/2016 | Stojanovic et al. | |
| 2017/0073335 | A1 | 3/2017 | Kanno et al. | |

FOREIGN PATENT DOCUMENTS

| | | |
|---|---|---|
| WO | 2011066864 A1 | 6/2011 |
| WO | 2012065139 A2 | 5/2012 |

(Continued)

OTHER PUBLICATIONS

Ciesielski; Tumour Biol 2017, 39, 1-8. https://doi.org/10.1177/1010428317695017 (Year: 2017).*
Sahin; Blood 2016, 128, 737. https://doi.org/10.1182/blood.V128.22.737.737 (Year: 2016).*
Yang; PLoS One 2015, 10, e0133896. https://doi.org/10.1371/journal.pone.0133896 (Year: 2015).*
Zhao; Cell Reports 2015, 13, 1692-1704. https://doi.org/10.1016/j.celrep.2015.10.037 (Year: 2015).*

(Continued)

*Primary Examiner* — Daniel R Carcanague
(74) *Attorney, Agent, or Firm* — Dinsmore & Shohl LLP

(57) ABSTRACT

A method of treating a subject suffering from a condition characterized by over-expression of Ten-eleven translocation 1 (TET1) is provided, the method including administering to the subject an effective amount of a compound, or a pharmaceutically acceptable salt thereof, having the Formula I:

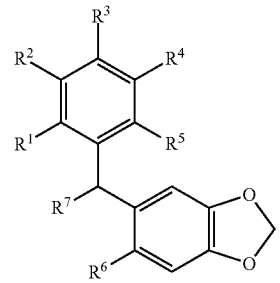

wherein: $R^1$, $R^2$, $R^3$, $R^4$, and $R^5$ are each independently selected from the group consisting of H, hydroxyl, alkyl, alkoxy, amine, halo, and trifluoromethyl, and wherein any two adjacent moieties of $R^1$, $R^2$, $R^3$, $R^4$, and $R^5$ may come together to form a heterocyclic ring; $R^6$ is H or hydroxyl; and $R^7$ is selected from H,

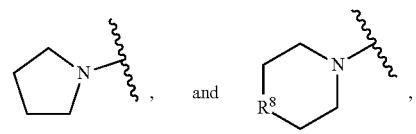

wherein $R^8$ is C or O. Also provided are methods for selectively suppressing transcription of TET1 and/or reducing a level of 5-hydroxymethylcytosine in a subject by administering an effective amount of a Formula I compound and pharmaceutical compositions comprising Formula I compounds.

9 Claims, 35 Drawing Sheets

Specification includes a Sequence Listing.

(56) References Cited

FOREIGN PATENT DOCUMENTS

WO 20150168621 A1 11/2015
WO 2019025424 A1 2/2019

OTHER PUBLICATIONS

"Understanding Leukemia" Leukemia and Lymphoma Society, 2012, 32 pages. Downloaded May 4, 2023 from https://www.lls.org/sites/default/files/2021-05/PS70_UnderstandingLeukemia_Eng_4_15reprint.pdf (Year: 2012).*
J.K. Batra et al, Methylenedioxy-genzopyran Analogs of Polophyllotoxin, a New Synthetic Class of Antimitotic Agents that Inhibit Tubulin Polymerization; Biochemical Pharmacology, Ellsevier, US, vol. 37, No. 13, Jul. 1, 1988; pp. 2595-2602.
Hao Huang et al, TET1 Plays an Essential Oncogenic Role in MLL-Rearranged Leukemia; Proceedings of the National Academy of Sciences of the United States of America, vol. 110, No. 29, Jul. 2013; pp. 11994-11999.
Antonia Lavecchia et al, Discovery of a Novel Small Molecule Inhibitor Targeting the Frataxin/Ubiquitin Interaction via Structure-Based Virtual Screening and Bioassays; Journal of Medicinal Chemistry, vol. 56. No. 7, Mar. 29, 2013, pp. 2861-2873.
Pubchem-CID 339882; Mar. 26, 2005, pp. 1-14.
Pubchem-CID 339892; Mar. 26, 2005, pp. 1-13.
Appelbaum; Nat. Rev. Clin. Oncol. 2012, 9, 376-377. doi 10.1038/nrclinonc.2012.09 (Year: 2012).
Jurd; Journal of heterocyclic chemistry, 1988, vol. 25, 89-96. DOI: 10.1002/jhet.5570250113 (Year: 1988).
Jurd; Journal of heterocyclic chemistry, 1985, 22, 993-995. DOI: 10.1002/jhet.5570220412 (Year: 1985).
Jurd; Journal of heterocyclic chemistry, 1989, 26, 1349-1352. DOI: 10.1002/jhet.5570260524 (Year: 1989).
Batra; Biochemical Pharmacology, 1986, 35, 4013-4018. DOI: 10.1016/0006-2952(86)90020-1 (Year: 1986).
NCI DTP Web Page information dated Nov. 10, 2015, 2 pages; Downloaded on Apr. 6, 2021 from https://dtp.cancer.gov/organization/dscb/obtianing/default.htm (Year: 2015).
Jiang; Nat Commun. 2017, 8, 2099. DOI: 10.1038/s41467-017-02290-w (Year: 2017).
Chemical Abstracts STN Registry Database record for RN 299420-83-0, 6-[3,5-Bis(1,1-dimethylethyl)-4-hydroxyphenyl]-4-morpholinylmethyl]-1,3-benzodioxol-5-ol, entered on Oct. 26, 2000 (Year: 2000).
National Center for Biotechnology Information. PubChem Substand Record for SID 467173, Source: DTP/NCI. https//pubchem.ncbi.nlm.nih.gov/substance/467173. Accessed Apr. 6, 2021. Date Available Mar. 26, 2005. Date Last Modified Dec. 19, 2011. (Year. 2011).
National Center for Biotechnology Information. PubChem Substand Record for SID 467527, 116409-29-1, Source: DTP/NCI. https//pubchem.ncbi.nlm.nih.gov/substance/467527. Accessed Apr. 6, 2021. Date Available Mar. 26, 2005. Date Last Modified Dec. 19, 2011. (Year. 2011).
CN First Office Action dated Oct. 18, 2022 pertaining to CN application No. 201880028052.6 filed Apr. 26, 2018, pp. 1-11.
Pubchem-SID 467527; Mar. 26, 2005, pp. 1-8.
Pubchem-CID 339882; Mar. 26, 2005, pp. 1-12.
J.K. Batra et al, Methylenedioxy-benzopyran Analogs of Podophyllotoxin, a New Synthetic Class of Antimitotic Agents that Inhibit Tubulin Polymerization; Biochemical Pharmacology, vol. 37, No. 13, Jul. 1, 1988; pp. 2595-2602.

* cited by examiner

METHODS, AGENTS, AND COMPOSITIONS FOR THE TREATMENT OF ACUTE MYELOID LEUKEMIA

CROSS REFERENCE TO RELATED APPLICATIONS

This application is a continuation of U.S. application Ser. No. 16/608,083, now U.S. Pat. No. 11,311,513, filed Oct. 24, 2019, which is a U.S. National Stage of International Application PCT/US2018/000111, filed Apr. 26, 2018, which claims priority to U.S. Provisional Application Ser. No. 62/490,184, filed Apr. 26, 2017, which are all hereby incorporated by reference in their entirety.

GOVERNMENT RIGHTS

This invention was made with government support under R01 CA-211614, R01 CA-178454, and R01 CA-182528 awarded by the National Institutes of Health. The Government has certain rights in the invention.

SEQUENCE LISTING

Incorporated herein by reference is a CRF sequence listing having file name 10738-941_SEQLIST.txt (2.20 kB), created Aug. 3, 2023.

TECHNICAL FIELD

This disclosure relates to the field of cancer therapy. More specifically, this disclosure relates to benzodioxole compounds and their compositions and methods of use in the treatment of cancers associated with over-expression of Ten-eleven translocation 1 (TET1), particularly acute myeloid leukemia (AML).

BACKGROUND

Acute myeloid leukemia (AML) is one of the most common and fatal forms of hematopoietic malignancies. Despite the improved risk stratifications and treatment-adapted strategies, with standard chemotherapies, still only 35%-40% of younger (aged <60) and 5%-15% of older (aged≥60) patients with AML can survive over 5 years. Many AML subtypes, such as the MLL-rearranged AMLs, are often associated with unfavorable outcome. Further, current treatment frequently involves intensive post-remission treatment with multiple cycles of high-dose cytarabine (Ara-C), which impairs the quality of life of the patients. While the incidence of AML is continually rising due to aging, most elderly patients cannot bear intensive chemotherapy and are associated with very poor survival. Thus, improved therapeutic strategies with less intensive treatment but a higher cure rate are urgently needed.

The Ten-eleven translocation (TET) proteins (including TET1/2/3) are known to be able to convert 5-methylcytosine (5mC) to 5-hydroxymethylcytosine (5hmC), leading to DNA demethylation. TET1, the founding member of the TET family, was first identified as a fusion partner of the MLL gene associated with t(10;11)(q22;q23) in AML. In contrast to the down-regulation and potential tumor-suppressor roles of all three TET genes reported in various types of solid tumors as well as the repression and tumor-suppressor role of TET2 observed in hematopoietic malignancies, the present inventors recently showed that TET1 was significantly up-regulated in MLL-rearranged AML and played an essential oncogenic role in the development of MLL-fusion-induced leukemia. An independent study by Zhao et al. confirmed the essential oncogenic role of Tet1 in the development of myeloid malignancies (Zhao, et al., *Combined Loss of Tet1 and Tet2 Promotes B Cell, but Not Myeloid Malignancies*, in Mice, Cell Rep 13: 1692-1704 (2015)). Thus, given the fact that knockout of Tet1 expression shows only very minor effects on normal development including hematopoiesis, TET1 is an attractive therapeutic target for AML. A need remains for effective therapies for acute myeloid leukemia (AML).

SUMMARY

Accordingly, through a series of in vitro drug screening and in vivo preclinical animal model studies, a class of benzodioxole chemical compounds has been identified as potent inhibitors that significantly and selectively suppress the viability of AML cells with high level of TET1 expression (i.e., TET1-high AML cells) and dramatically repress the progression of TET1-high AML in mice. These compounds directly bind STAT3/5 as STAT inhibitors and thereby suppress TET1 transcription and TET1 signaling, leading to potent anti-leukemic effects.

In one embodiment, a method of treating acute myeloid leukemia is provided, the method comprising administering to a subject in need thereof an effective amount of a compound, or a pharmaceutically acceptable salt thereof, having the formula:

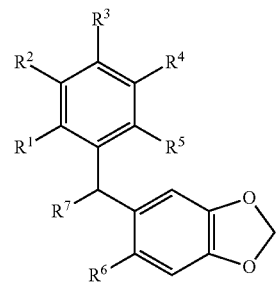

wherein:
  $R^1$, $R^2$, $R^3$, $R^4$, and $R^5$ are each independently selected from the group consisting of H, hydroxyl, alkyl, alkoxy, amine, halo, and trifluoromethyl, and wherein any two adjacent moieties of $R^1$, $R^2$, $R^3$, $R^4$, and $R^5$ may come together to form a heterocyclic ring;
  $R^6$ is H or hydroxyl; and
  $R^7$ is selected from H,

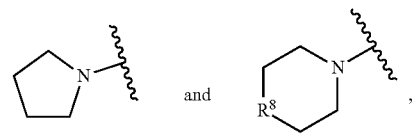

wherein $R^8$ is C or O.

In another embodiment, a pharmaceutical composition is provided, comprising (a) an effective amount of a Formula I compound, or a pharmaceutically acceptable salt thereof, and (b) at least one pharmaceutically acceptable carrier.

k,l) for 48 hrs. Relative cell viabilities are shown. (m) Cre-Tet1$^{fl/fl}$ mouse BM progenitor cells were retrovirally transduced with MLL-AF9. Transduced cells were induced with polyLC for 7 days, and then treated with 500 nM NSC-370284, UC-514321, or DMSO control for 48 hrs. Relative cell viability is shown. (n-o) THP-1 (n) and MONOMAC-6 (o) cells were infected with lentivirus of pLenti-puro vector-based Tet1 construct. Cells with or without doxycyclin inducing were treated with 250 nM NSC-370284, UC-514321 or DMSO control for 24 hrs. Relative cell viability is shown. *, P<0.05; **, P<0.01, two-tailed t-test. Error bar indicates SD of triplicate experiments.

Figure 6:
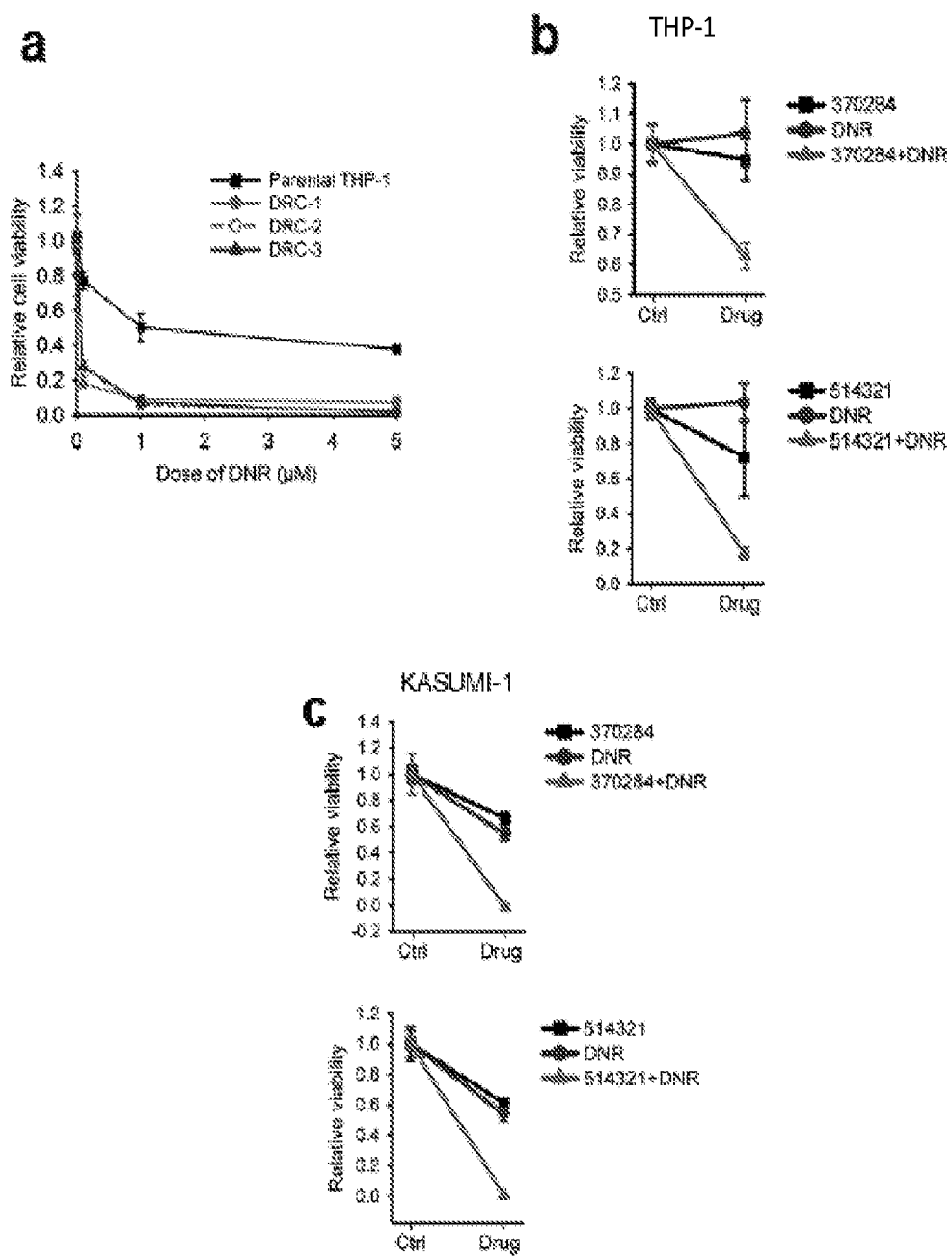
Figure 6:
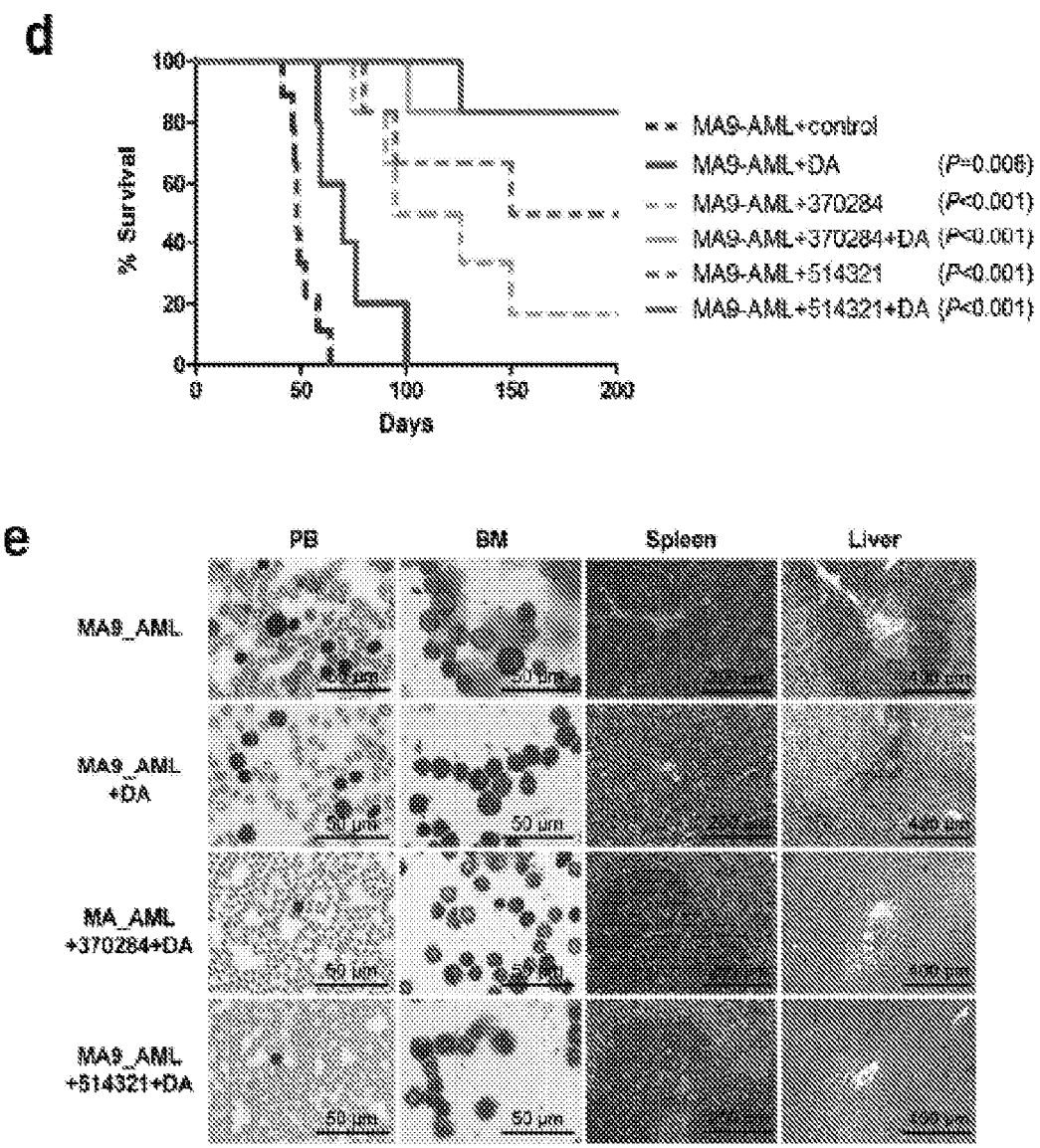

FIG. 6. Synergistic effect of NSC-370284 or UC-514321 with daunorubicin (DNR) and Ara-C in treating TET1-high AMLs in vitro and in vivo. (a) NSC-370284-resistant AML cells are sensitive to DNR. Three of the THP-1 NSC-370284-resistant clones (DRC-1-3) and the parental control were treated with DNR at indicated doses. Cell viability was tested 48 hours after the treatments. (b,c) THP-1 (b) and Kasumi-1 (c) cells were treated with DMSO (Ctrl), 25 nM NSC-370284 (upper panels) or UC-514321 (lower panels), and/or 100 nM DNR. Relative cell viability at 48 hours post drug treatment is shown. Error bar indicates SD of triplicate experiments. (d) Synergistic therapy of NSC-370284 or UC-514321 in combination with standard chemotherapy. Secondary BMT recipient mice were transplanted with primary MLL-AF9 leukemic BM cells. Upon the onset of leukemia, the mice were treated with DMSO (control), "5+3" regimen alone (i.e., a daily dose of 50 mg/kg Ara-C for five days along with a daily dose of 3 mg/kg DNR during the first three days of Ara-C treatment), or in combination with 10 days' NSC-370284 or UC-514321 treatment, 2.5 mg/kg, i.p., once per day. 5-9 mice were included in each group. Kaplan-Meier curves are shown. The P values were determined by log-rank test. (e) Wright-Giemsa staining of mouse PB and BM, or H&E staining of mouse spleen and liver of MLL-AF9 secondary BMT recipients treated with "5+3" alone, or combinational therapy.

Figure 7:

FIG. 7. Expression pattern of TET1 in TCGA database. TET1 gene expression levels were analyzed through cBio-Portal website.

Figure 8:
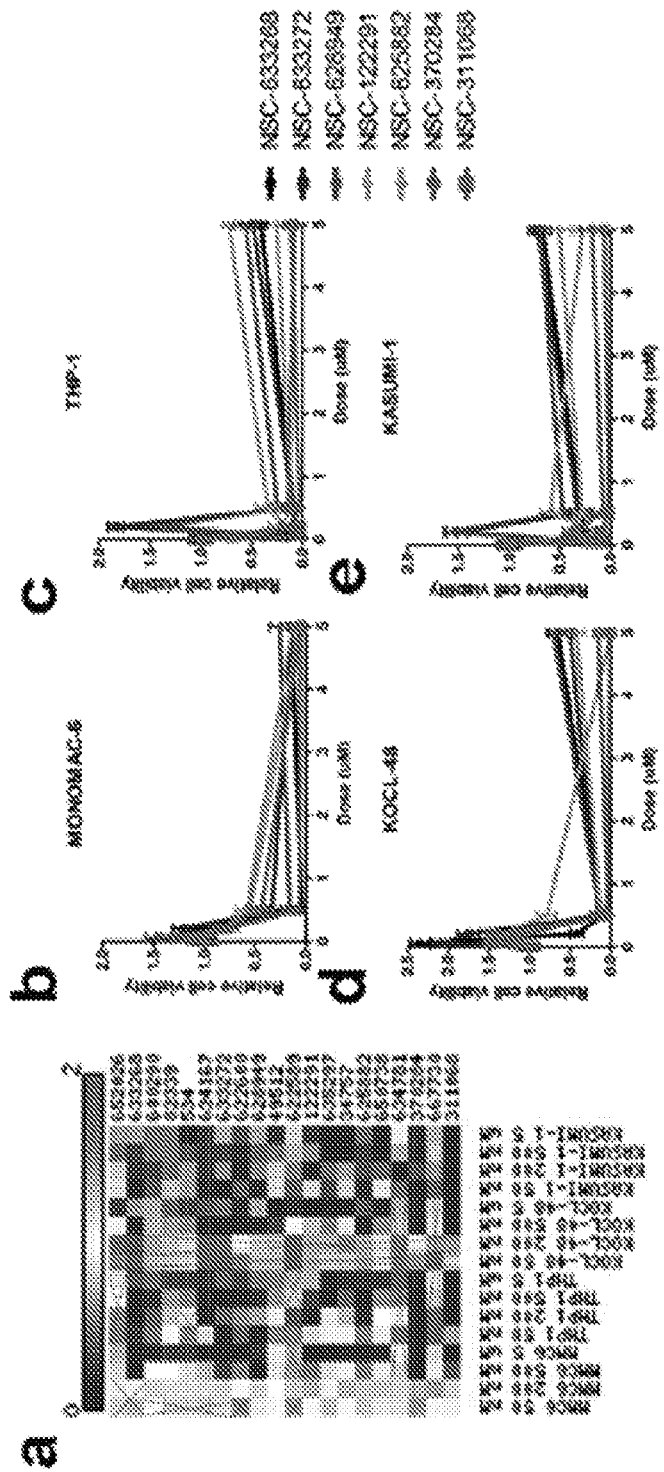
Figure 8:
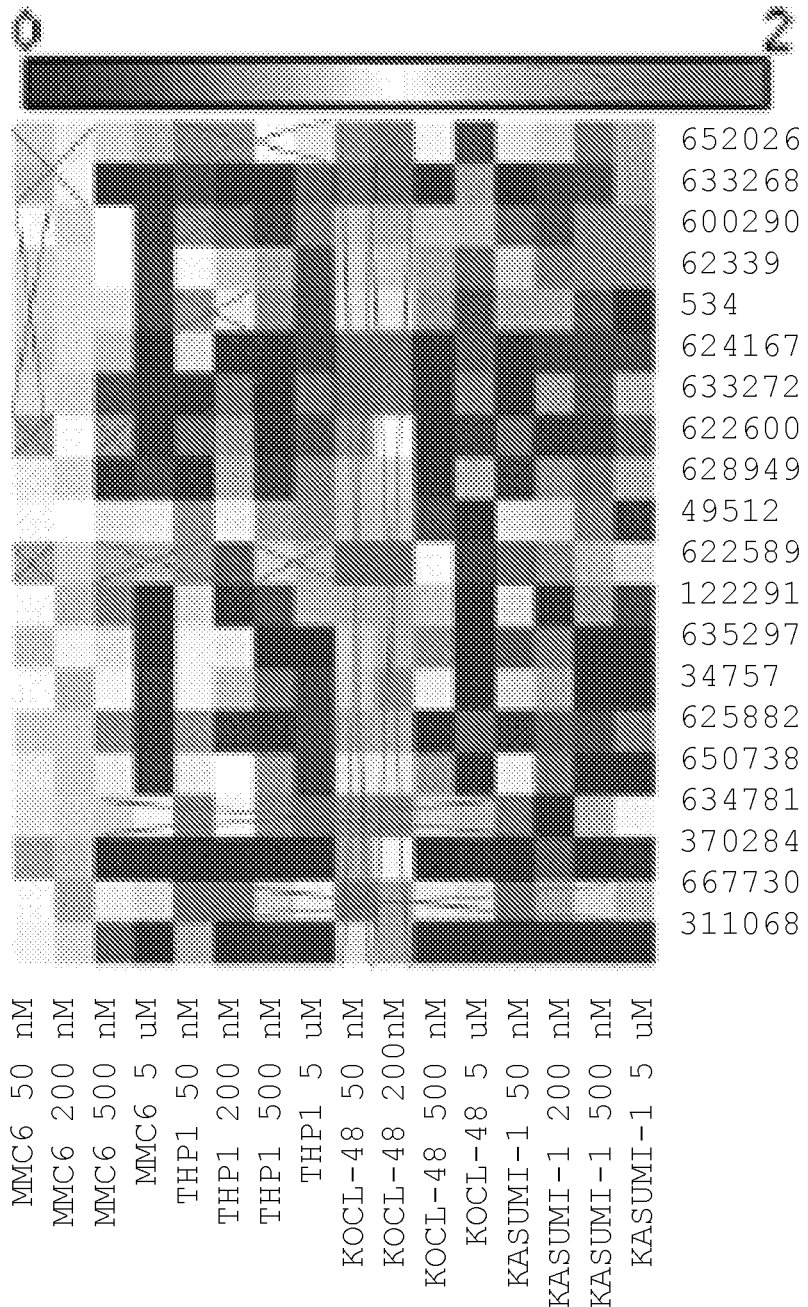
Figure 8:
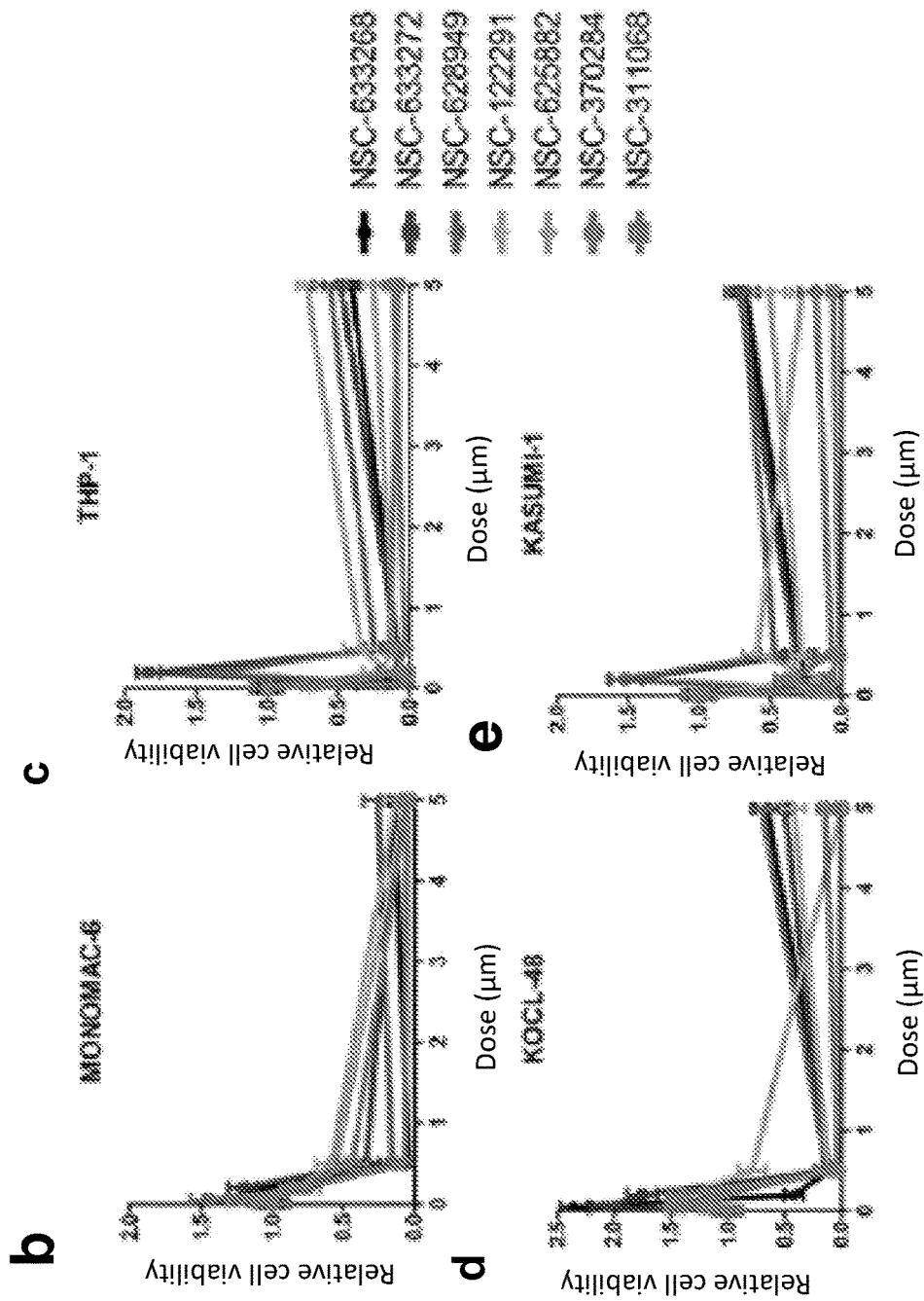

FIG. 8. Cell viability screening of the top 20 chemical compounds that showed positive correlation between drug response and TET1 level in NCI-60 panel collection. MONOMAC-6 (MMC6), THP-1, KOCL-48 and KASUMI-1 cells were treated with the 20 top candidate chemical compounds individually at indicated doses for 48 hrs. Heatmap (a) and dose curves (b-e) are shown.

Figure 9:
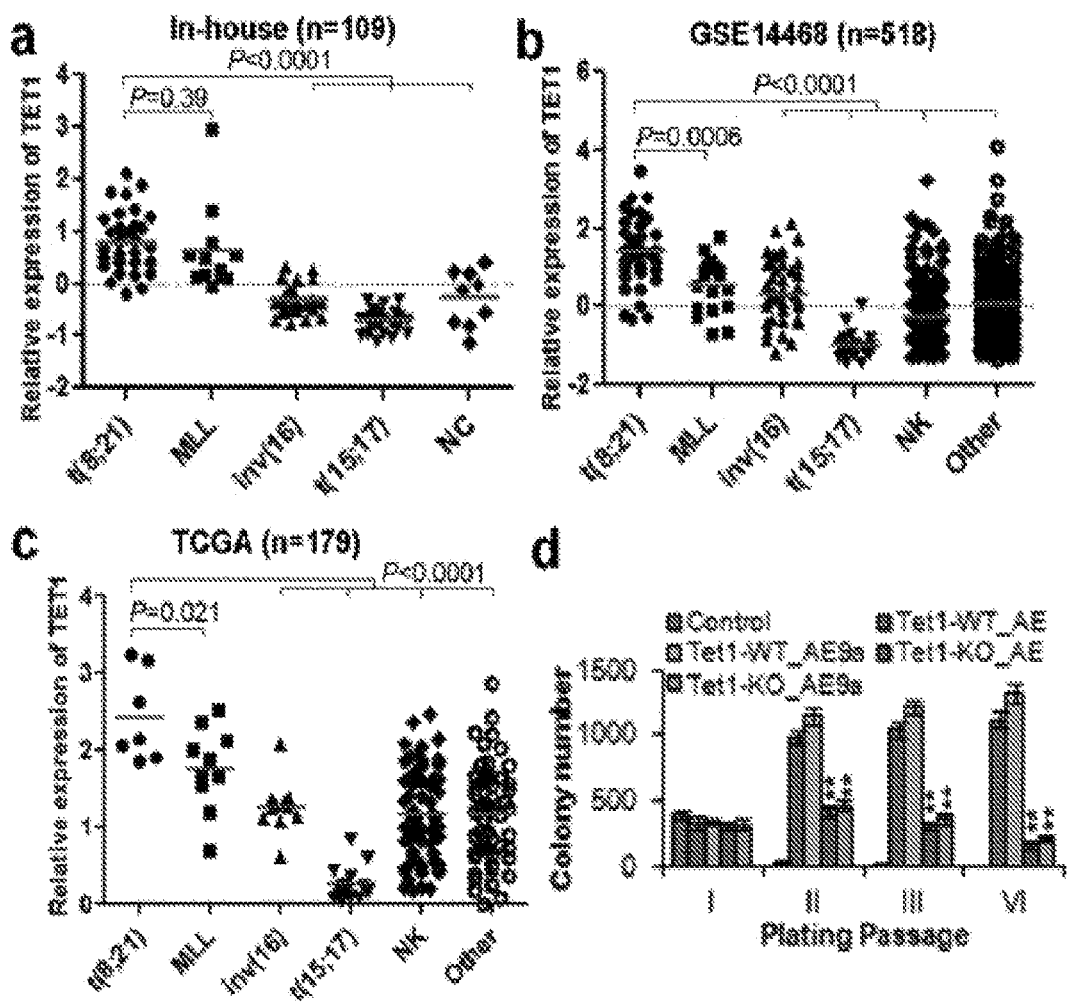

FIG. 9. High expression and oncogenic role of TET1 in t(8;21) AML. (a-c) Comparison of TET1 expression between t(8;21) AML and other subtypes of AML or normal control (NC) samples. (a) In an in-house 109-sample dataset, including 30 t(8;21), 12 MLL-rearranged (MLL), 27 inv (16), and 31 t(15;17) AML, along with 9 normal control (NC) samples. (b) In the Netherlands 518-sample dataset (GSE14468), including 38 t(8;21), 19MLL-rearranged, 42 inv(16), 25 t(15;17), 214 normal karyotype (NK) and 180 other AML samples. (c) In the TCGA 179-sample dataset, including 7 t(8;21), 11 MLL-rearranged, 11 inv(16), 16 t(15;17), 75 normal karyotype (NK) and 59 other AML samples. Two-tailed t-test was used to calculate the P values. Bars show the median values. (d) Tet1 knockout inhibits t(8;21) fusion-induced cell transformation. Colony-forming/replating assays of wild-type or Tet1$^{-/-}$ mouse BM progenitor cells transduced with MSCV-PIG-AE (AE), or MSCV-PIG-AE9a (AE9a). Wild-type cells transduced with MSCV-PIG serve as a negative control. **, P<0.01, two-tailed t-test.

Figure 10:
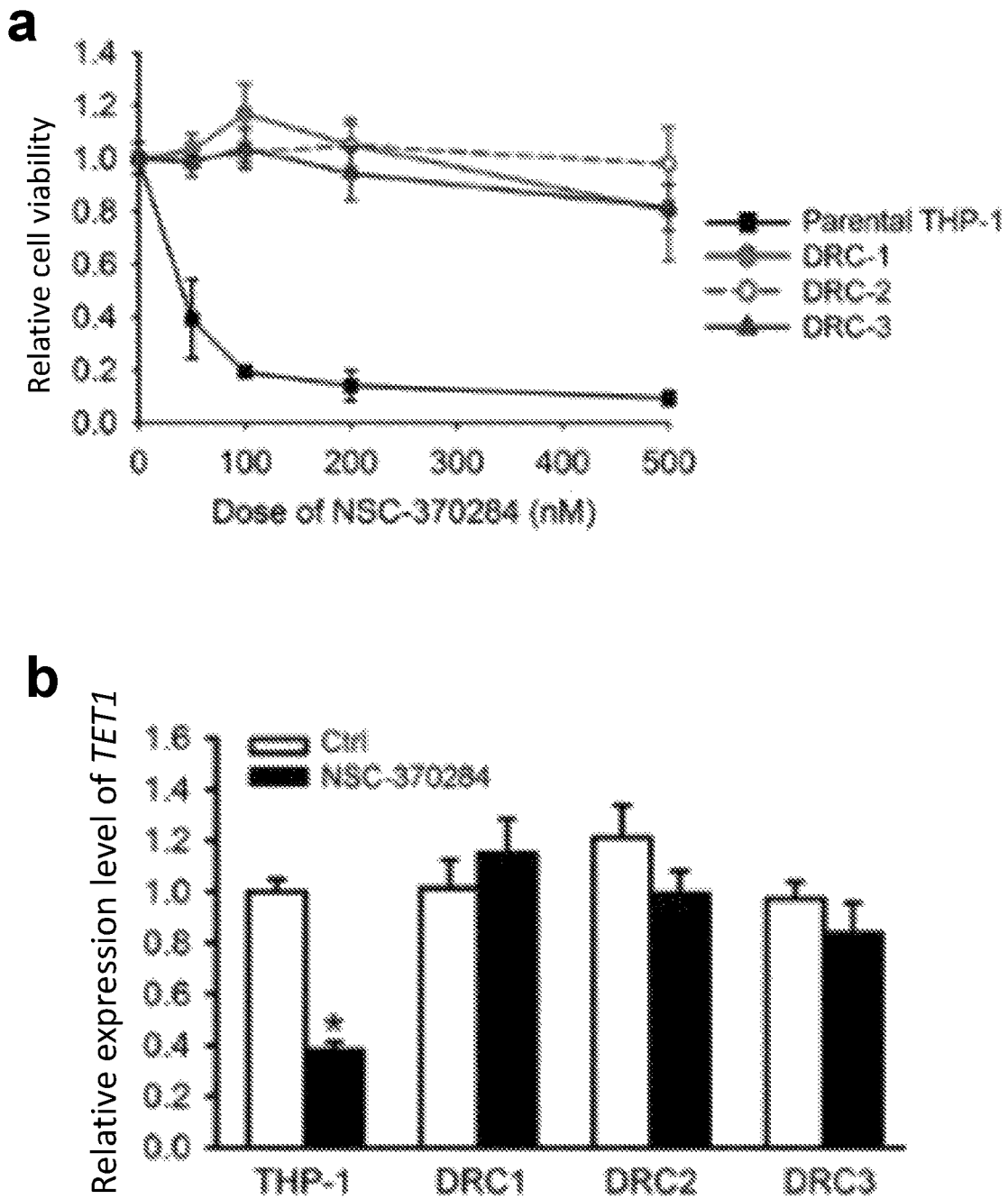
Figure 10:
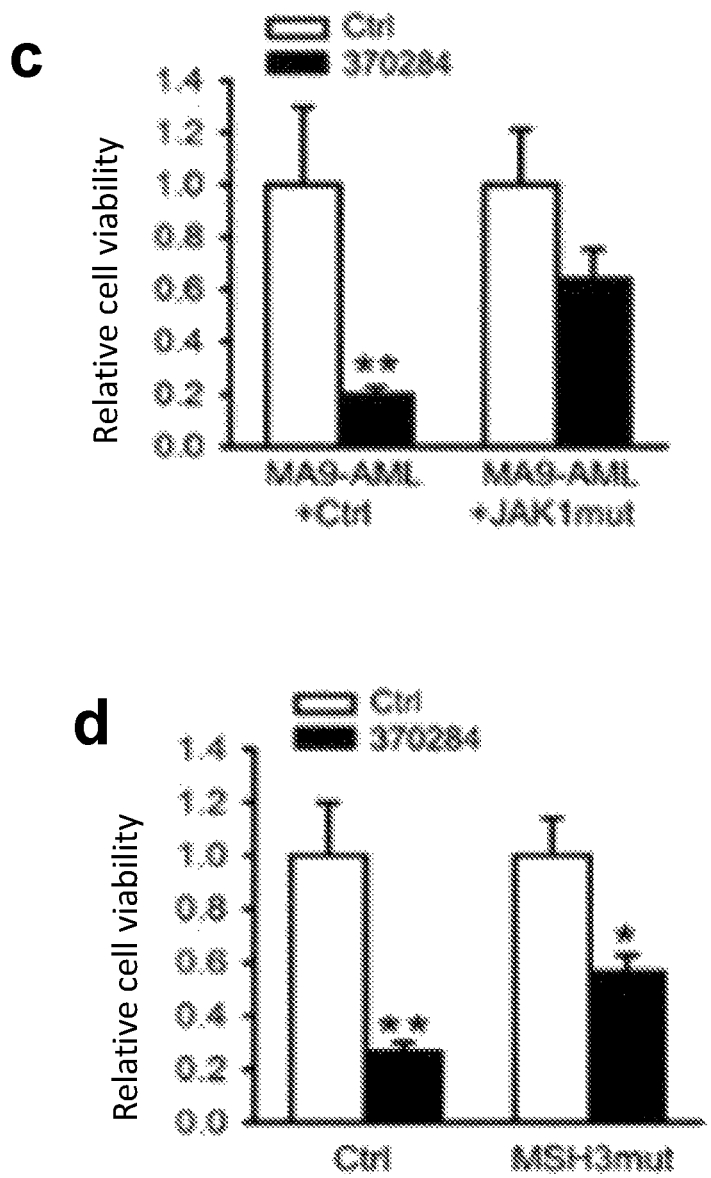
Figure 10:
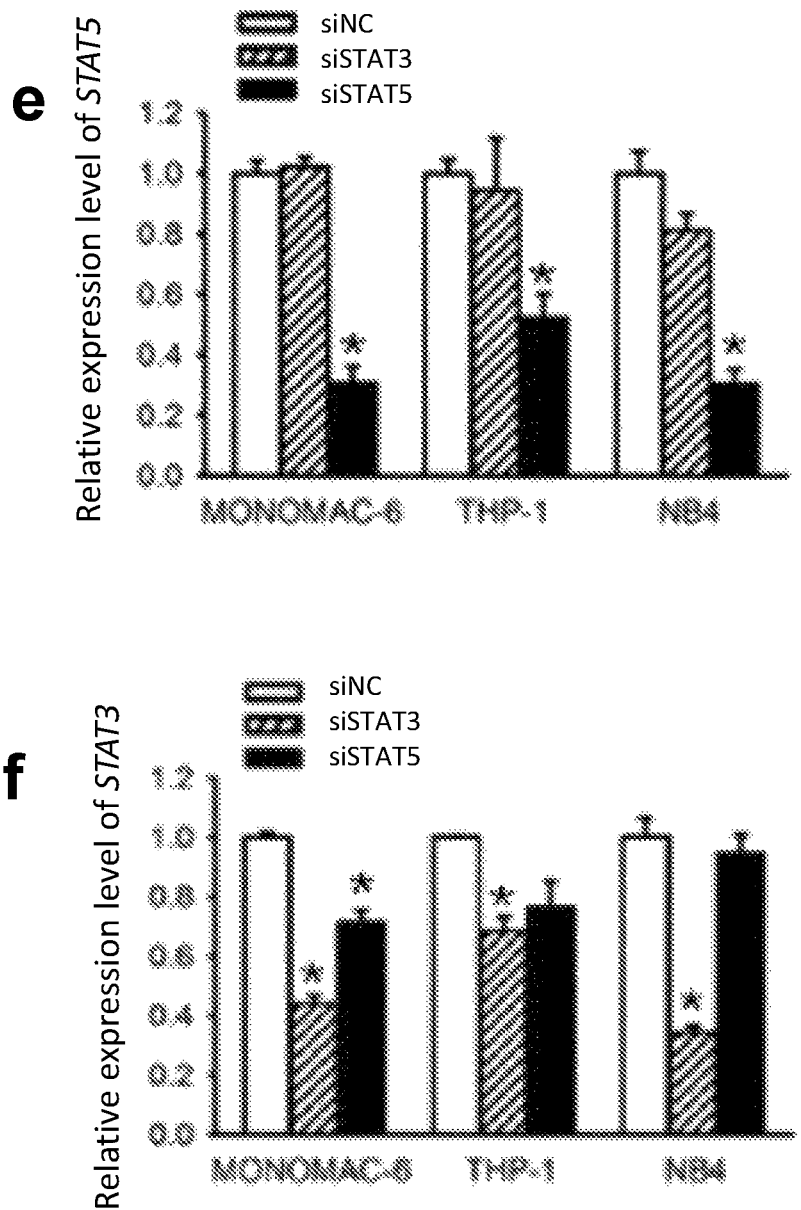
Figure 10:
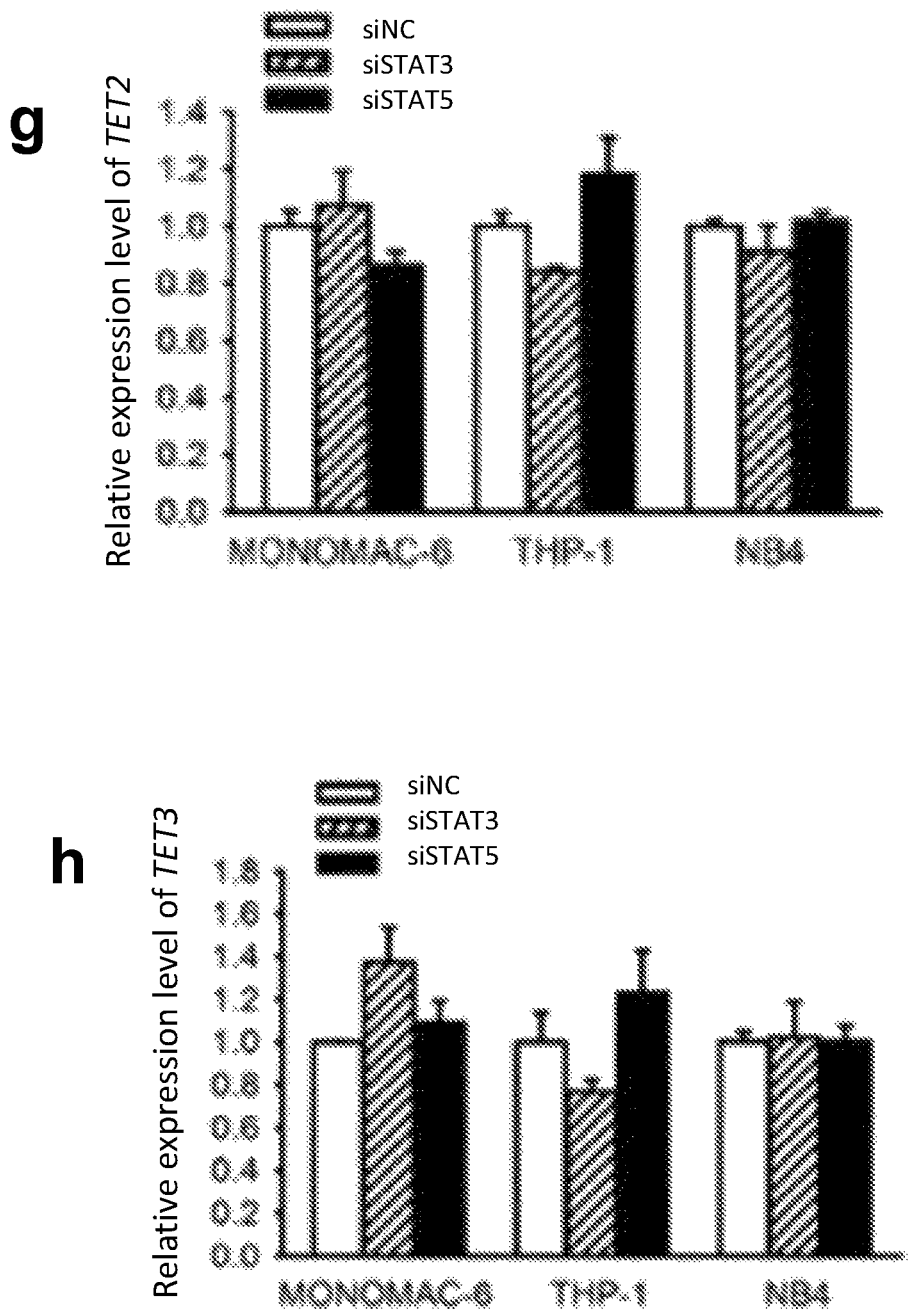
Figure 10:
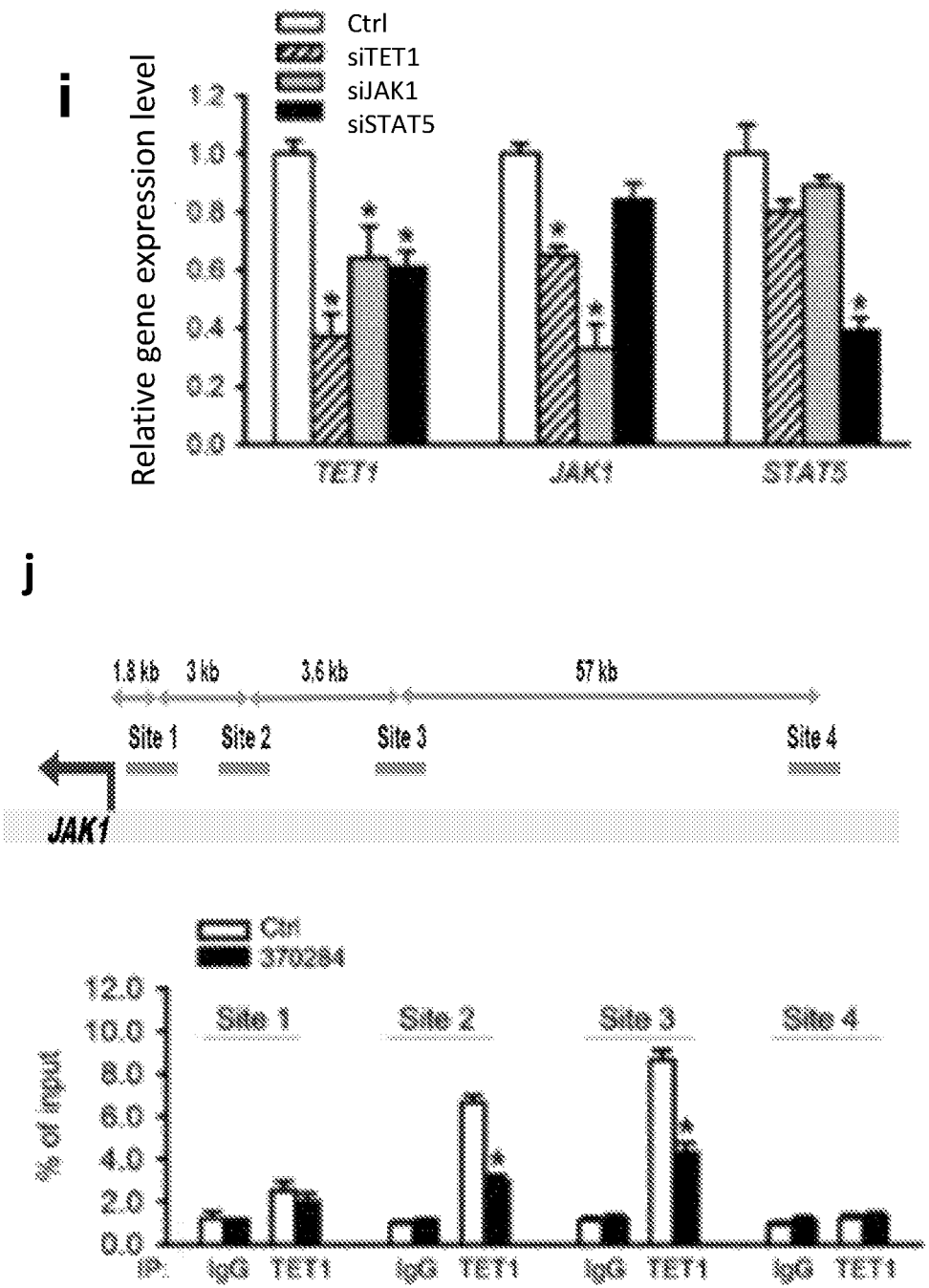
Figure 10:
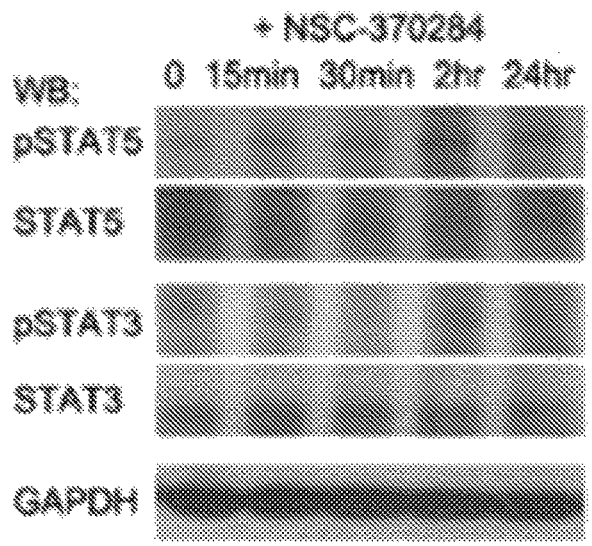
Figure 10:
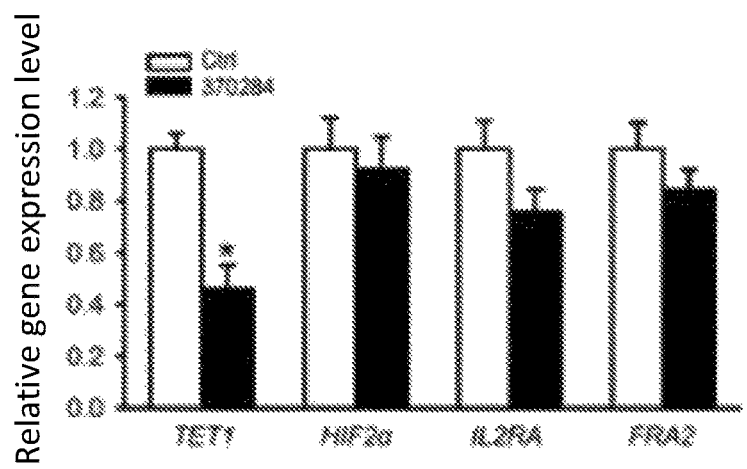
Figure 10:
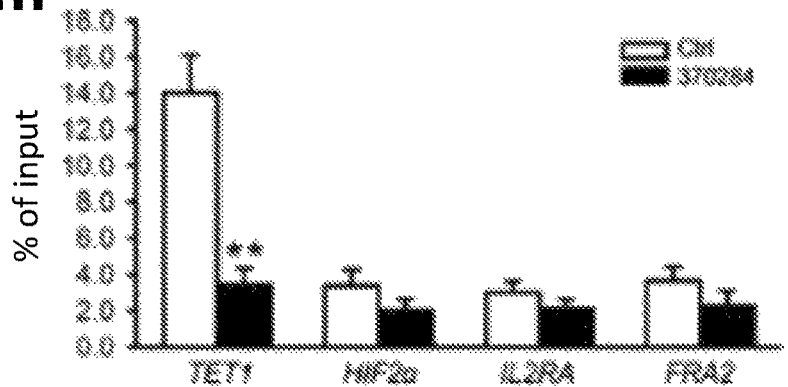

FIG. 10. NSC-370284 regulates TET1 expression through targeting STAT3/5. (a) THP-1 parental cells or representative drug-resistant clones (i.e., DRC-1, 2, 3) were treated with NSC-370284 at indicated doses for 48 hrs. Relative cell viabilities are shown. (b) THP-1 parental cells or drug resistant clones were treated with DMSO control or 500 nM NSC-370284 for 48 hrs. Levels of TET1 transcripts are shown. (c) Relative viability of MLL-AF9-AML cells transduced with MSCV-PIG-JAK1$^{A839G}$mutant (Mut) or MSCV-PIG vector (ctrl) and then treated with DMSO or NSC-370284 (50 nM) for 48 hours. (d) Relative viability of THP-1 cells transduced with pLJM1-MSH3$^{V600I}$ or pLJM1-EGFP control and then treated with DMSO or NSC-370284 (50 nM) for 48 hours. (e-h) MONOMAC-6, THP-1 and NB4 cells were transfected with control siRNA (siNC), siSTAT3, or siSTAT5. Expression levels of STAT5 (e), STAT3 (f), TET2 (g) and TET3 (h) were detected by aPCR 48 hrs post-transfection. (i) THP-1 cells were transfected with control siRNA (siNC), siTET1, siJAK1 or siSTAT5. Gene expression levels were detected by qPCR 48 hrs post-transfection. MONOMAC-6 cells were treated with DMSO control or 500 nM NSC-370284. (j) ChIP-qPCR assay was carried out 48 hrs after drug treatment. Enrichment of TET1 or IgG at the JAK1 promoter region and other regions are shown. (k) MONOMAC-6 cells were treated with 250 nM NSC-370284 for 0 min, 15 min, 30 min, 2 hrs, and 24 hrs. Protein levels were detected thereafter. (l,m) THP-1 cells were treated with DMSO or 25 nM NSC-370284 for 24 hrs. Expression levels of TET1, HIF2 a, IL2RA andFRA2 (l) were detected through qPCR. The enrichment of STAT5 on the promoters of TET1 (Site 2; CpG), HIF2a, IL2RA and FRA2 (m) was determined through ChIP-qPCR assays. *, P<0.05; **, P<0.01, two-tailed t-test. Error bar indicates SD of triplicate experiments.

Figure 11:
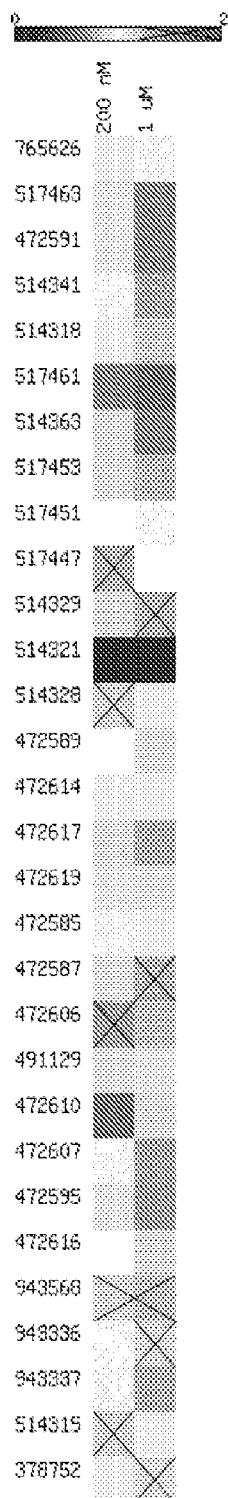

FIG. 11. Effects of 30 analogues of NSC-370284 on the viability of MONOMAC-6 cells. MONOMAC-6 cells were treated with 30 candidate analogues individually at indicated doses for 48 hrs. Heatmap of relative cell viability (as compared with DMSO treated control group) is shown.

Figure 12:
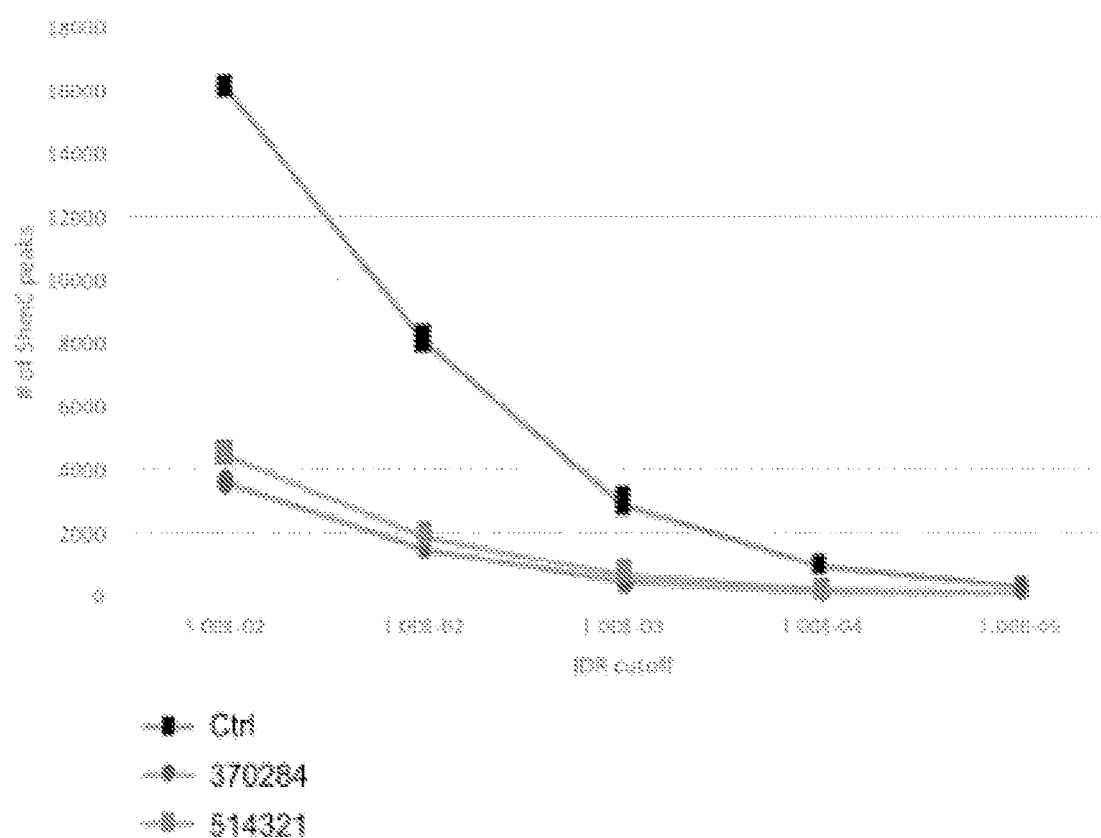
Figure 12:
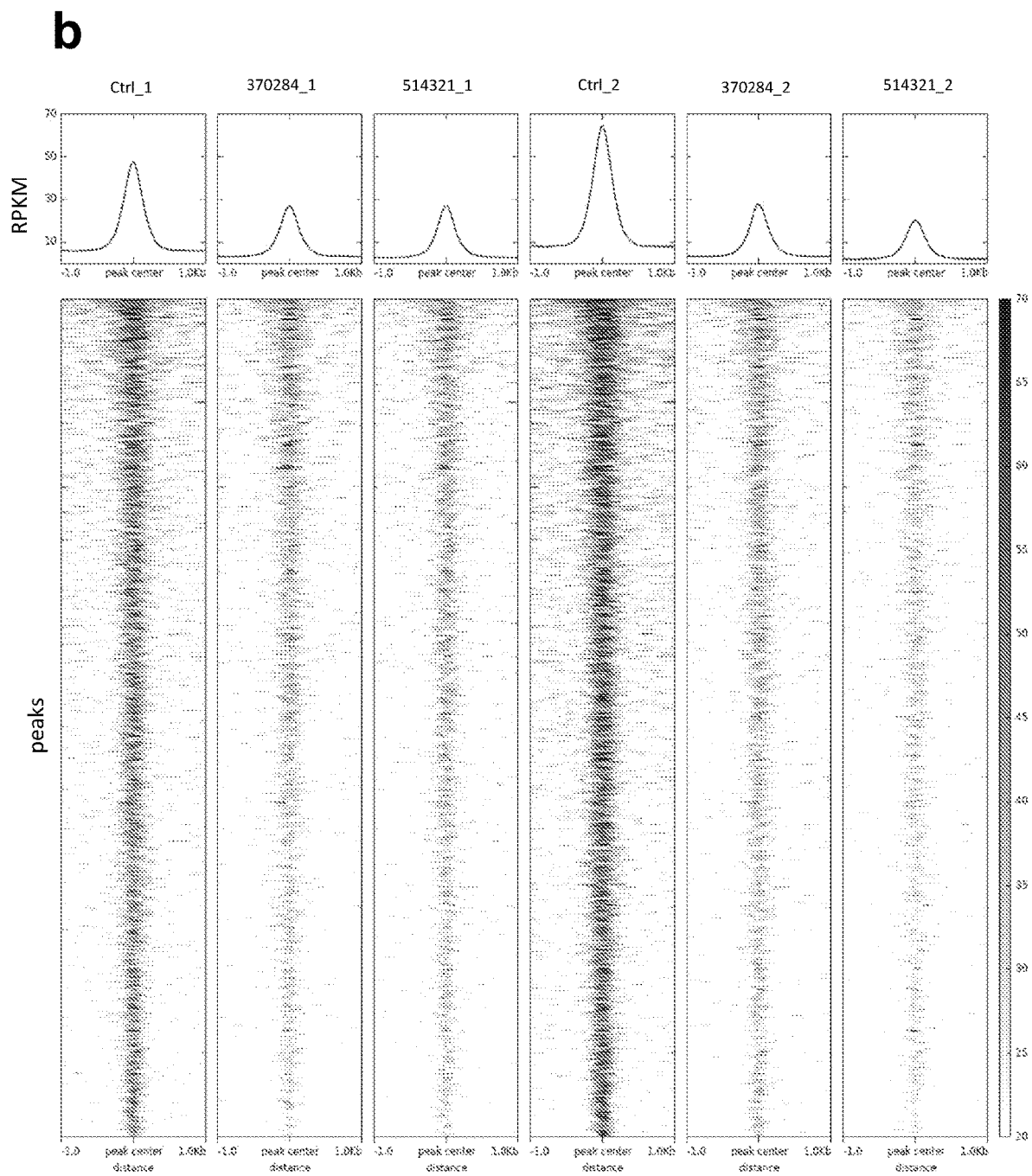
Figure 12:
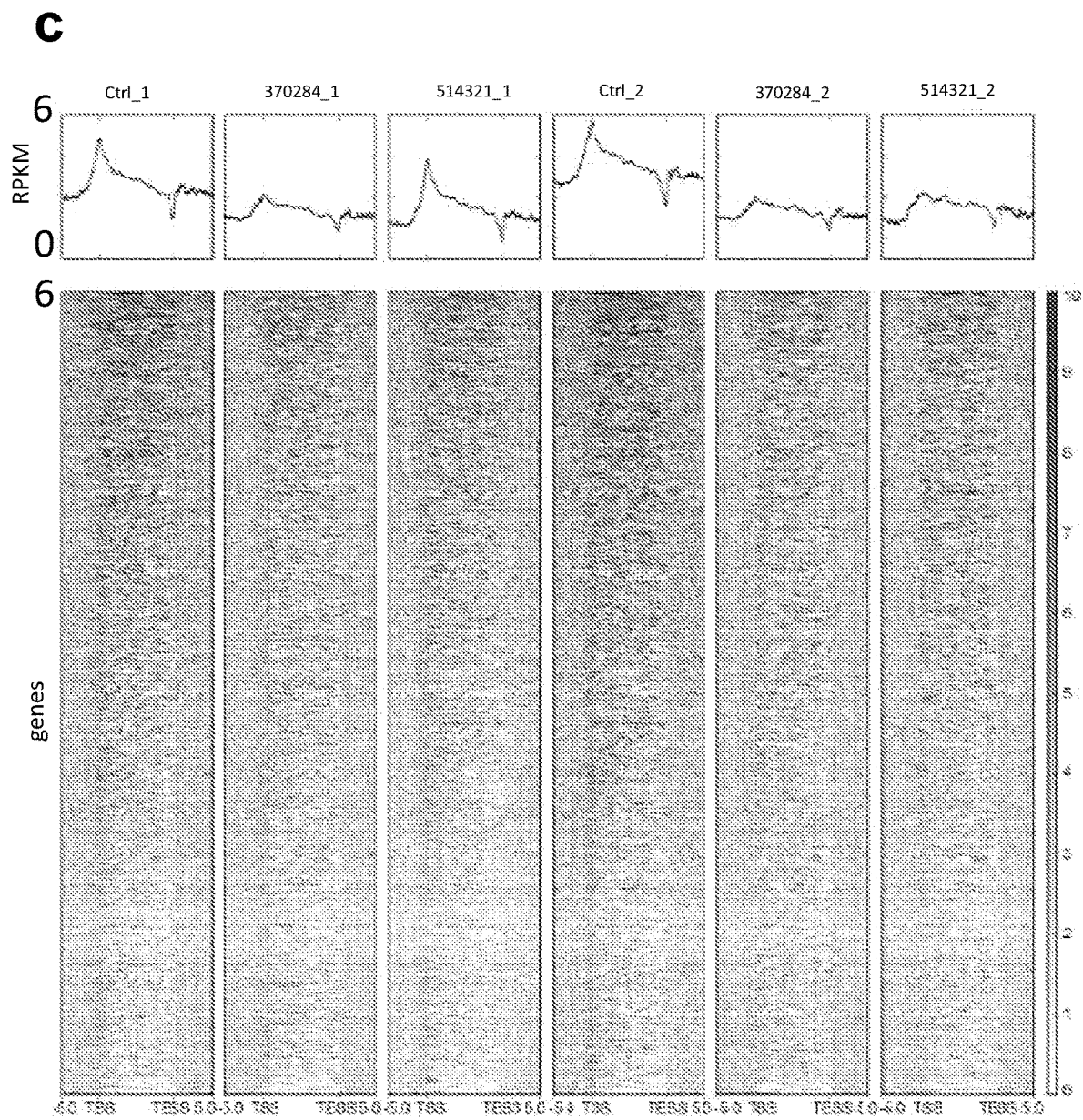

FIG. 12. Comparison of 5hmC enrichment between NSC-370284 or UC-514321-treated AML cells and control (DMSO-treated) cells. (a) Comparison of 5hmC peak numbers across the whole genome in ML-2 AML cells treated with NSC-370284 or UC-514321, or DMSO (control). 5hmC peak counts at different IDR cutoffs were shown. (b) Read density across 5hmC enriched regions. A unified catalog of 5hmC enriched regions was generated. Shown are heatmaps rank-ordered by reads per kilobase of exon model per million mapped reads (RPKM) of 5hmC-Seal samples minus that of the input samples. (c) Read density across all RefSeq genes. Shown are heatmaps of 5hmC read density changes across all RefSeq gene loci and 5 kb flanking regions (minus input values).

Figure 13:
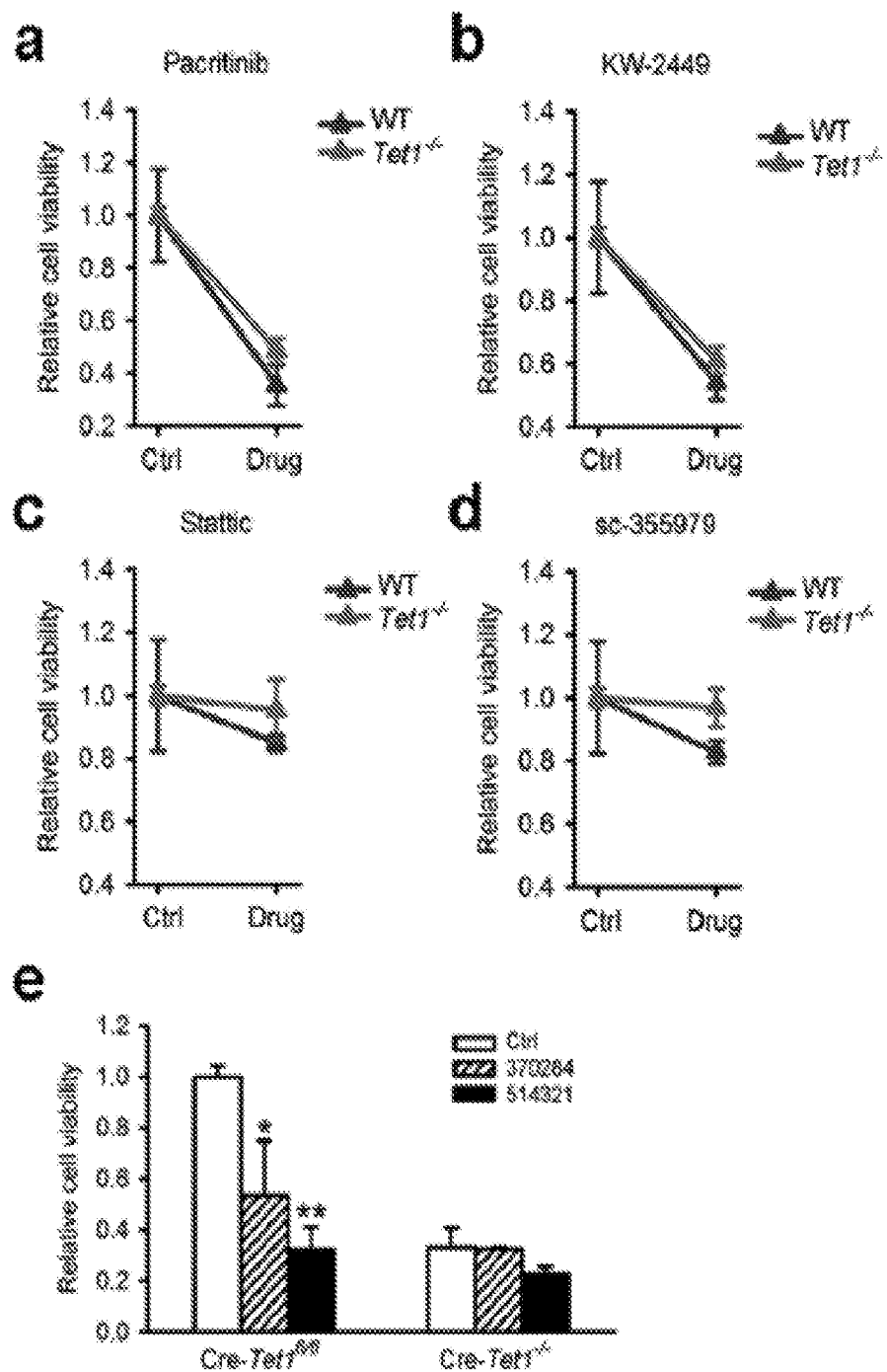
Figure 14:
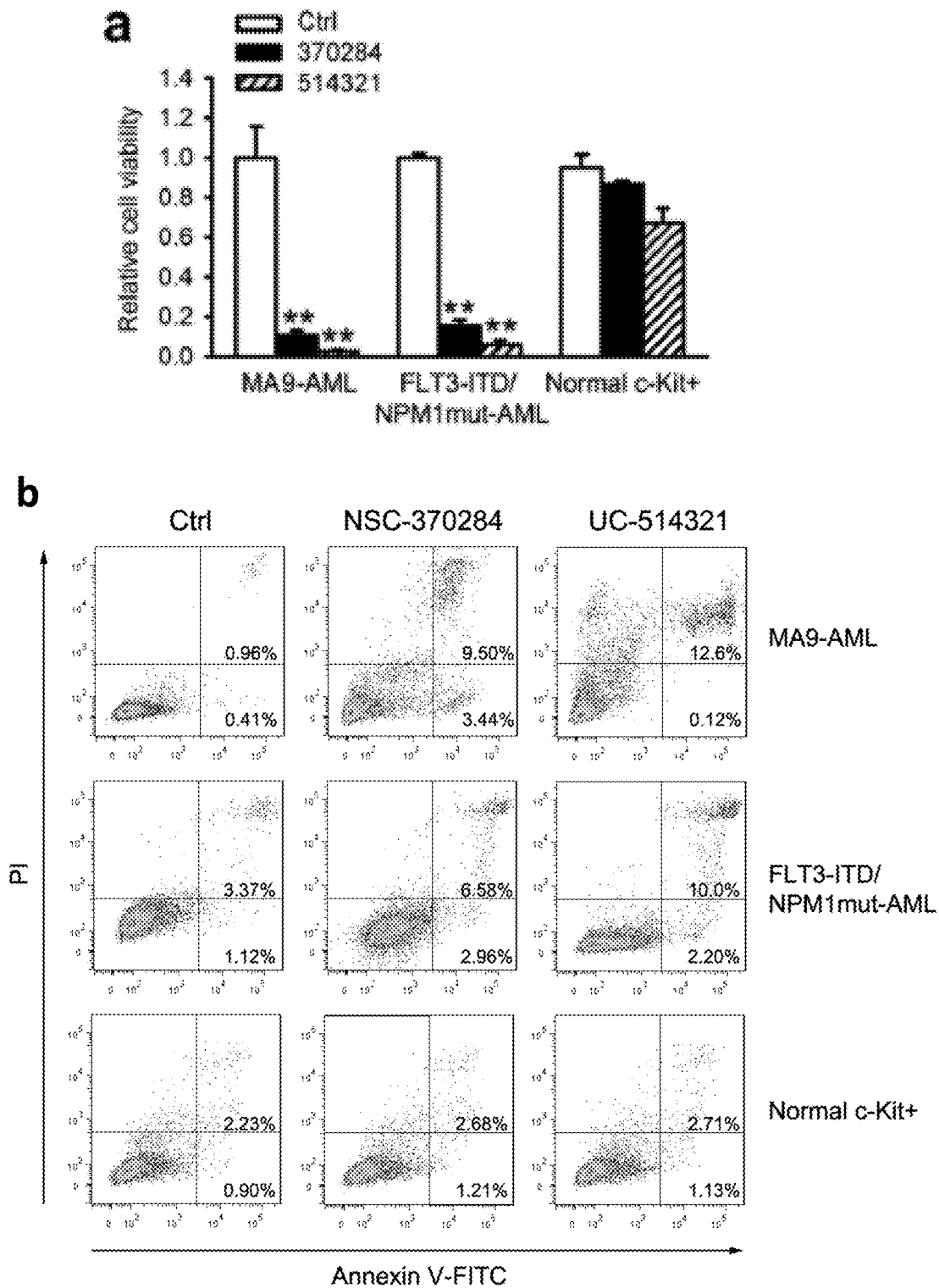
Figure 14:
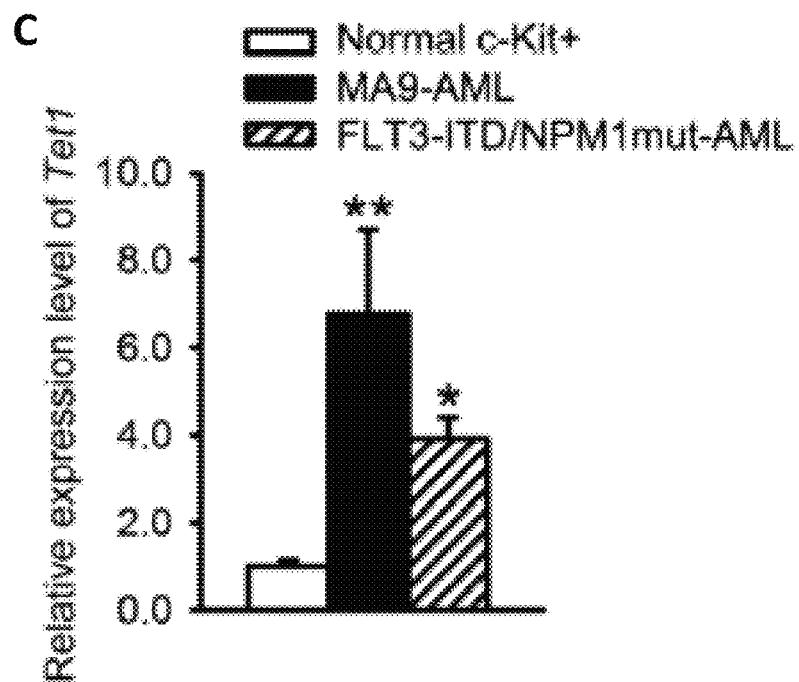

FIG. 13. Unlike those of NSC-370284 and UC-514321, the effects of a set of JAK/STAT inhibitors are less TET1-dependent. (a-d) BM progenitor cells of wild-type or Tet1$^{1/1}$ mice were retrovirally transduced with MLL-AF9. Infected cells were treated with 200 nM JAK/STAT inhibitors individually, including Pacritinib (a), KW-2449 (b), Stattic (c) or sc-355979 (d), for 48 hrs. Relative cell viabilities are shown. (e) Cre-Tet1$^{fl/fl}$ mouse BM progenitor cells were retrovirally transduced with MLL-AF9. Transduced cells were induced with polyLC for 7 days, and then treated with 500 nM NSC-370284, UC-514321, or DMSO control for 48 hrs. Cell viabilities (normalized to non-induced Cre-Tet1$^{fl/fl}$ treated with DMSO control) are shown. 'K, P<0.05; 'K'K, P<0.01, two-tailed t-test FIG. 14. Comparison of effects of NSC-370284 and UC-514321 between AML cells and normal hematopoietic stem/progenitor cells (HSPCs; herein, c-Kit+ BM progenitor cells). BM cells of leukemic mice with MLL-AF9 fusion (MA9-AML) or FLT3-ITD/NPM1$^{mut}$, and c-Kit+ HSPCs from a pool of 6 healthy donor mice were cultured in liquid medium. Cells were treated with 50 nM NSC-370284, UC-514321, or DMSO as control. MTS (a), apoptosis assays (b) and qPCR (c) were conducted 3 days after cell seeding or drug treatments. Error bar indicates SD of triplicate experiments.

Figure 15:
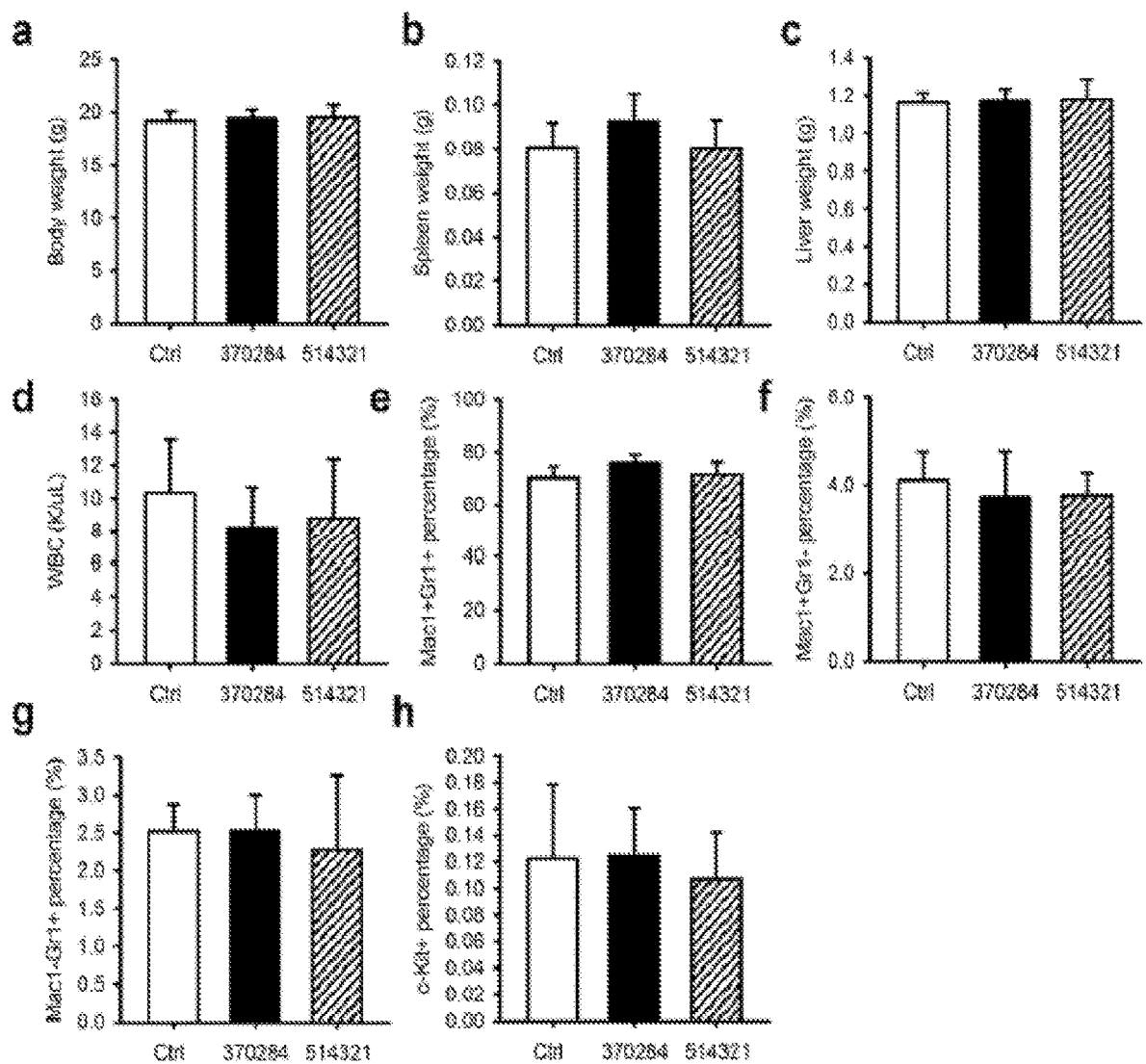

FIG. 15. Acute toxicity profiling of NSC-370284 and UC-514321. Wild-type mice (n=5 for each group) were injected with DMSO (control), 2.5 mg/kg NSC-370284 or UC-514321, i.p., once per day, for 10 days. 24 hrs after the last administration, body weights (a), weights of spleens (b), livers (c), total PB WBC counts (d), BM Mac1+Gr1+ (e), Mac1+Gr1− (f), Mac1−Gr1+ (g), and c-Kit+ (h) populations were analyzed.

Figure 16:
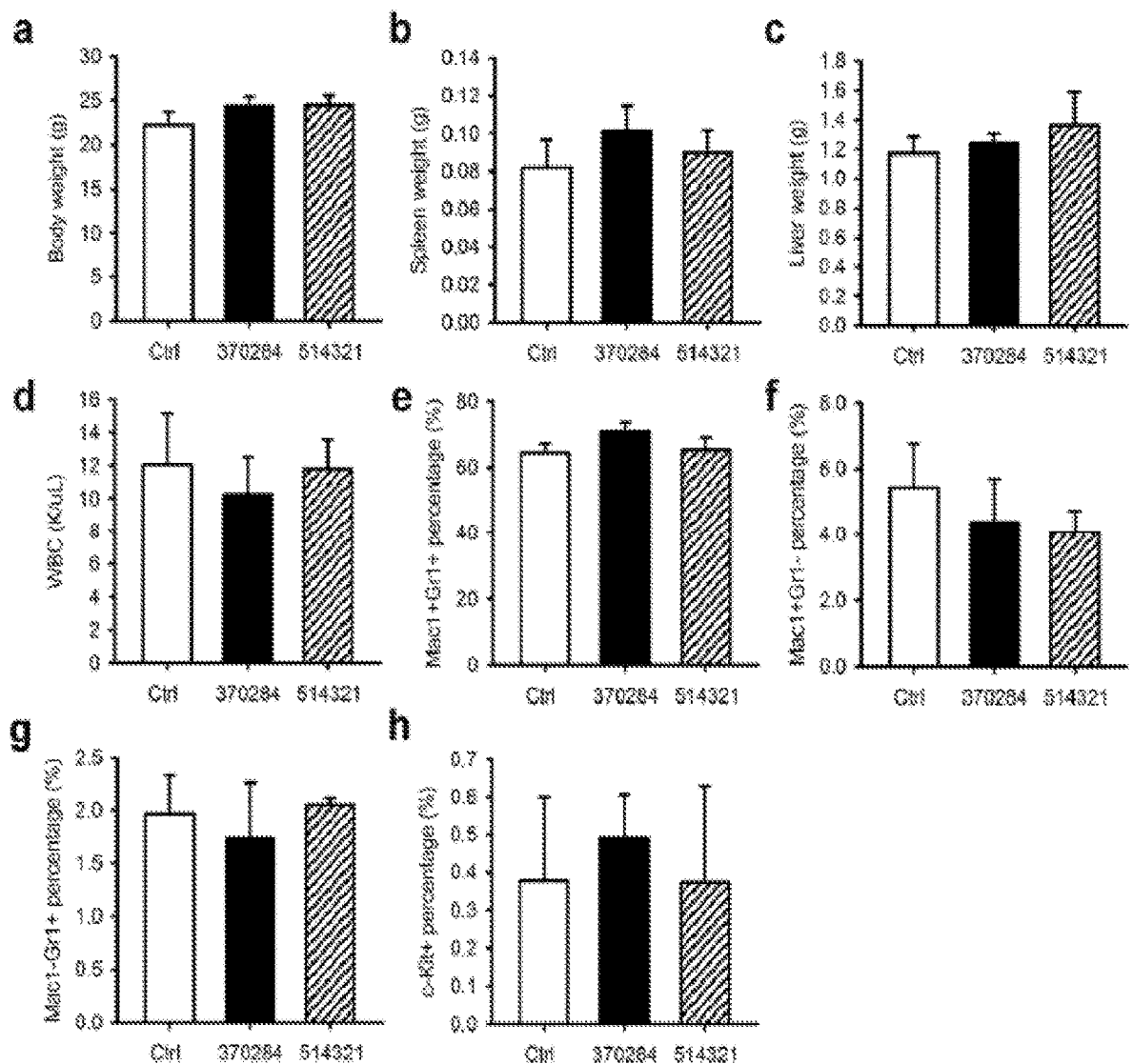

FIG. 16. Long-term toxicity profiling of NSC-370284 and UC-514321. Wild-type C57BL/6 mice (n=5 for each group) were injected with DMSO (control), 2.5 mg/kg NSC-370284 or UC-514321, i.p., once per day, for 10 days. 200 days after the last administration, body weights (a), weights of spleens (b), livers (c), total PB WBC counts (d), BM Mac1+Gr1+ (e), Mac1+Gr1+ (f), Mac1−Gr1+ (g), and c-Kit+ (h) populations were analyzed.

Figure 17:
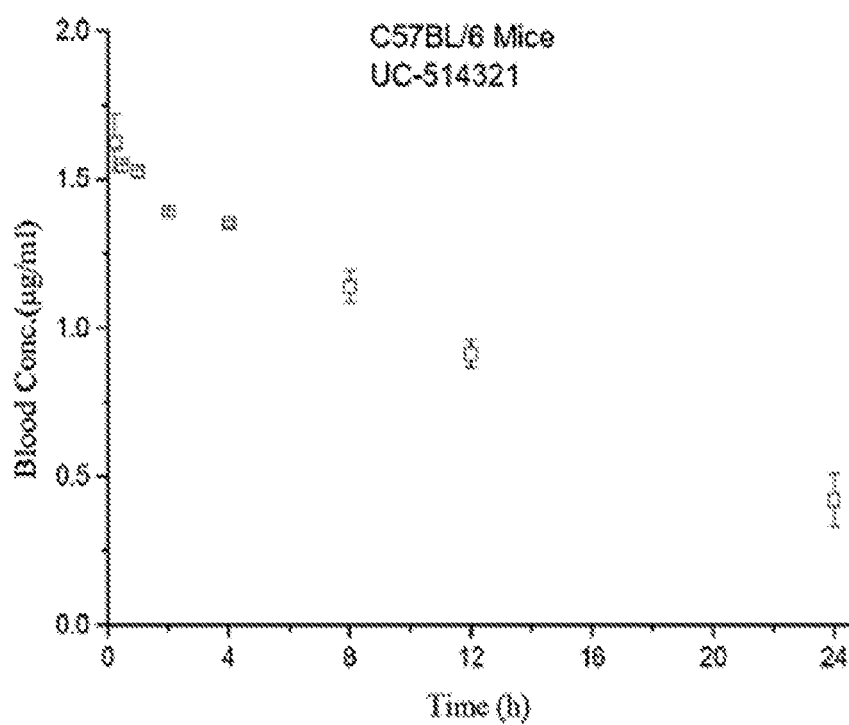

FIG. 17. Blood concentration of UC-514321 after intraperitoneal injection. Error bar indicates SD of triplicate experiments.

Figure 18:
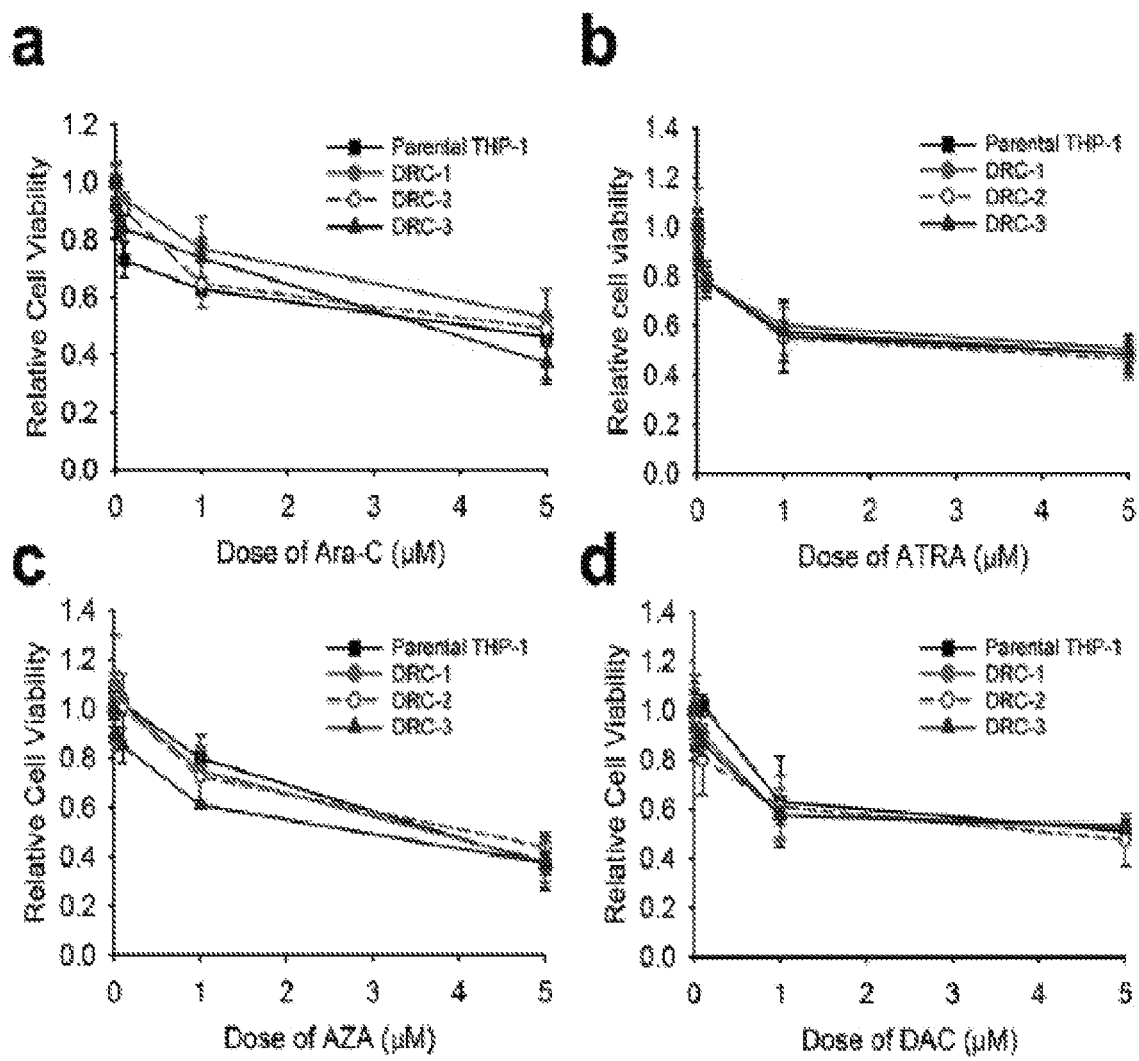

FIG. 18. Effects of standard chemotherapy reagents on the cell viability of THP-1 NSC-370284-resistant clones. Three representative THP-1 NSC-370284-resistant clones (DRC-1-3) and the parental control were treated with cytarabine (AraC) (a), all-trans retinoic acid (ATRA) (b), azacytidine (AZA) (c) and decitabine (DAC) (d) at indicated doses. Cell viability was tested 48 hours after the treatments. Error bar indicates SD of triplicate experiments.

DETAILED DESCRIPTION

The details of one or more embodiments of the presently-disclosed subject matter are set forth in this document. Modifications to embodiments described in this document, and other embodiments, will be evident to those of ordinary skill in the art after a study of the information provided herein.

While the following terms are believed to be well understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, pH, size, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

An "effective amount," as used herein, refers to an amount of a substance (e.g., a therapeutic compound and/or composition) that elicits a desired biological response. In some embodiments, an effective amount of a substance is an amount that is sufficient, when administered to a subject suffering from or susceptible to a disease, disorder, and/or condition, to treat, diagnose, prevent, and/or delay and/or alleviate one or more symptoms of the disease, disorder, and/or condition. As will be appreciated by those of ordinary skill in this art, the effective amount of a substance may vary depending on such factors as the desired biological endpoint, the substance to be delivered, the target cell or tissue, etc. For example, the effective amount of a formulation to treat a disease, disorder, and/or condition is the amount that alleviates, ameliorates, relieves, inhibits, prevents, delays onset of; reduces severity of and/or reduces incidence of one or more symptoms or features of the disease, disorder, and/or condition. Furthermore, an effective amount may be administered via a single dose or via multiple doses within a treatment regimen. In some embodiments, individual doses or compositions are considered to contain an effective amount when they contain an amount effective as a dose in the context of a treatment regimen. Those of ordinary skill in the art will appreciate that a dose or amount may be considered to be effective if it is or has been demonstrated to show statistically significant effectiveness when administered to a population of patients; a particular result need not be achieved in a particular individual patient in order for an amount to be considered to be effective as described herein.

As used herein, the term "alkyl" refers to a straight or branched saturated aliphatic hydrocarbon group having a single radical and 1-12 carbon atoms (i.e., C1-C12 alkyl). Non-limiting examples of alkyl groups include methyl, propyl, isopropyl, butyl, n-butyl, isobutyl, sec-butyl, tert-butyl, pentyl, hexyl, heptyl, octyl, nonyl, and the like. A branched alkyl means that one or more alkyl groups such as methyl, ethyl, or propyl replace one or both hydrogens in a —CH2— group of a linear alkyl chain. In certain embodiments, alkyl is a C1-C6 alkyl or a C1-C4 alkyl. In other embodiments, alkyl is selected from the group consisting of methyl, ethyl, propyl, isopropyl, butyl, n-butyl, isobutyl, sec-butyl, and tert-butyl.

Alkyl groups can optionally be unsubstituted or substituted (a "substituted alkyl") with one or more alkyl group substituents, which can be the same or different. The term "alkyl group substituent" includes but is not limited to alkyl, substituted alkyl, halo, hydroxyl, carboxyl, oxo, and the like. There can be optionally inserted along the alkyl chain one or more oxygen, sulfur or substituted or unsubstituted nitrogen atoms, wherein the nitrogen substituent is hydrogen or alkyl.

"Alkoxy" refers to an alkyl-O— group wherein alkyl is as previously described. The term "alkoxy" as used herein can refer to, for example, one or more of methoxy, ethoxy, propoxy, isopropoxy, butoxy, t-butoxy, pentoxy, and the like. In certain embodiments, alkoxy is a C1-C12 alkoxy, a C1-C6 alkoxy, or a C1-C4 alkoxy.

The term "amine," as used herein, includes primary, secondary, and tertiary amines.

The terms "halo," as used herein, refers to fluoro, chloro, bromo, and iodo groups.

"Heterocyclic" means cyclic carbon rings having one or more heteroatoms (atoms other than carbon) in the ring. The ring may be saturated, partially saturated, and unsaturated, and the heteroatoms may be selected from the group consisting of nitrogen, sulfur and oxygen. Examples of saturated heterocyclic rings include saturated 3 to 6-membered heteromonocyclic groups containing 1 to 4 nitrogen atoms, such as pyrrolidinyl, imidazolidinyl, piperidino, piperazinyl; saturated 3- to 6-membered heteromonocyclic groups containing 1 to 2 oxygen atoms, such as tetrahydrofuran, tetrahydropyranyl, dioxolane, and dioxane; saturated 3- to 6-membered heteromonocyclic groups containing 1 to 2 oxygen atoms and 1 to 3 nitrogen atoms, such as morpholinyl; saturated 3- to 6-membered heteromonocyclic groups containing 1 to 2 sulfur atoms and 1 to 3 nitrogen atoms, such as thiazolidinyl. Examples of partially saturated heterocyclic rings include furanyl, pyridinyl, imidazolyl, thiophenyl, pyrrolyl, pyrimidinyl, azole, dioxole, and the like.

When the term "independently selected" is used, the substituents being referred to (e.g., R groups, such as groups $R^1$ and $R^2$), can be identical or different. For example, both $R^1$ and $R^2$ can be the same substituent, or $R^1$ and $R^2$ can each be different substituents selected from a specified group.

The term "pharmaceutically acceptable excipient," as used herein, means any physiologically inert, pharmacologically inactive material known to one skilled in the art, which is compatible with the physical and chemical characteristics of the particular active agent selected for use. Pharmaceutically acceptable excipients include, but are not limited to, polymers, resins, plasticizers, fillers, lubricants, diluents, binders, disintegrants, solvents, co-solvents, buffer systems, surfactants, preservatives, sweetening agents, flavoring agents, pharmaceutical grade dyes or pigments, and viscosity agents.

Conditions characterized by over-expression of TET1 include conditions associated with higher levels of TET1 messenger RNA or TET1 protein. In some embodiments, higher TET1 expression is induced by oncogenic signaling, such as STAT3/5-associated signaling. In certain embodiments, conditions characterized by over-expression of TET1 include hematopoietic malignancies having higher TET1 expression compared to normal control cells.

The term "hematopoietic malignancy," as used herein, refers to malignancies of the hematopoietic and lymphoid tissues. Examples include, but are not limited to, lymphomas, leukemias, myeloproliferative neoplasms, plasma cell dyscrasias, histiocytic tumors, and dendritic cell neoplasms. In certain embodiments, hematopoietic malignancies include leukemias such as acute lymphoblastic leukemia (ALL), acute myeloid leukemia (AML), chronic lymphocytic leukemia (CLL), chronic myelogenous leukemia (CML), acute monocytic leukemia (AMoL), and the like. In other embodiments, hematopoietic malignancies include lymphomas such as Hodgkin's lymphomas, non-Hodgkin's lymphomas, and the like. In certain embodiments, hematopoietic malignancies include myelomas, such as multiple myeloma. In a specific embodiment, the hematopoietic malignancy is AML, including TET1-high AML.

The terms "over-express" or "over-expressed" as used herein refer to a gene product which is expressed at levels greater than normal endogenous expression for that gene product.

TET1-high acute myeloid leukemia (TET1-high AML) refers to AML wherein leukemic cells exhibit elevated or high level expression of TET1 relative to normal hematopoietic cells.

The terms "treat," "treatment," and "treating," as used herein, refer to a method of alleviating or abrogating a disease, disorder, and/or symptoms thereof in a subject, including a mammal. In certain embodiments, the subject is a human subject.

An "anti-cancer agent," as used herein, refers to a chemical compound or chemotherapeutic agent useful in the treatment of cancer. In certain embodiments, an anti-cancer agent is a first line chemotherapeutic agent, or an agent generally regarded as the standard therapy or first-administered therapy for a given type of cancer. In certain embodiments, the second anti-cancer agent is a chemotherapeutic agent for the treatment of AML selected from the group consisting of cytarabine, cladribine, fludarabine, topotecan, doxorubicin, daunorubicin, epirubicin, idarubicin, decitabine, azacitidine, all-trans-retinoic acid, arsenic trioxide, gemtuzumab ozogamicin, midostaurin, nelarabine, clofarabine, dasatinib, imatinib, ponatinib, JQ1, methotrexate, corticosteroids, histamine dihydrochloride, interleukin 2, and combinations thereof.

Compounds and Methods of Treatment

DNA methylcytosine dioxygenase Ten-eleven translocation 1 (TET1) is a critical oncoprotein in AML. Through a series of data analysis and drug screening, a class of compounds that selectively suppresses TET1 transcription and 5-hydroxymethylcytosine (5hmC) modification is disclosed herein. These compounds effectively inhibit cell viability in AML with high level expression of TET1 (i.e., TET1-high AML), including AML carrying t(11q23)/MLL-rearrangements and t(8;21) AML.

While knockout of Tet1 expression shows only very minor effects on normal development including hematopoiesis, recent studies have demonstrated that TET1 plays a critical oncogenic role in AML through promoting expression of oncogenic targets (e.g. HOXA9, MEIS1 and PBX3, etc.) and repressing expression of tumor-suppressor targets (e.g., miR-22). Thus, targeting TET1 signaling is a promising therapeutic strategy to treat TET1-high AMLs. In order to target critical oncogenic proteins with catalytic activity, one of the most popular approaches is to interfere the catalytic activity of oncogenic proteins, such as FLT3 inhibitor Quizartinib that represses the kinase activity of FLT3, and STAT inhibitor Stattic that blocks the dimerization of STAT3, etc. However, as shown in a number of clinical reports, treatments of catalytic activity inhibitors often result in aberrant up-regulation of the target oncoproteins or trigger gene mutations, which eventually leads to drug resistance. The discovery of the bromodomain and extra-terminal (BET) inhibitor JQ1 as an effective strategy to target c-Myc signaling suggested an alternative strategy of repressing the TET1 signaling instead of directly targeting the enzymatic activity of TET1. Any drugs that efficiently target the expression, i.e., transcription, translation, or degradation, of the oncogenes or oncogenic proteins could largely avoid drug resistance caused by target oncogene up-regulation or constitutively activated gene mutations. Moreover, it was reported previously that TET1 can recruit polycomb proteins to the promoter region of the mir-22 gene and suppress the primary transcription of this critical tumor-suppressor microRNA, and such transcriptional suppression is independent from TET1's enzymatic activity. Therefore, instead of seeking inhibitors targeting TET1 enzymatic activity directly that are unable to fully repress the function of TET1, inhibitors that suppress TET1 expression were selected in this study for treating AML.

Through correlation analysis of cell response to 20,602 chemical compounds and TET1 levels of in the NCI-60 collection of cancer cell samples, followed by MTS assays of top drug candidates in AML cells, two candidate chemical compounds (NSC-311068 and NSC-370284) were identified that each suppress AML cell viability and TET1 expression:

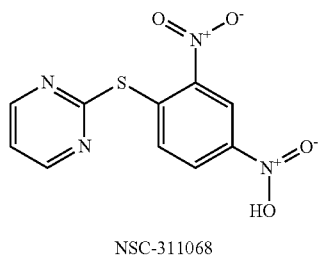

NSC-311068

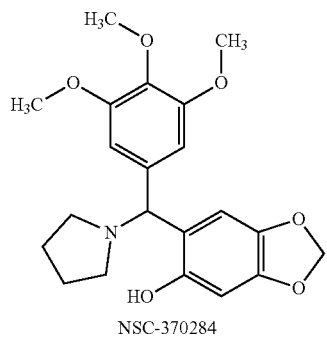

NSC-370284

Importantly, both NSC-311068 and especially NSC-370284 showed remarkable therapeutic effects in curing AML in vivo. UC-514321, a structural analog of NSC-370284, exhibited a more potent anti-leukemic activity in vitro and in vivo than NSC-370284:

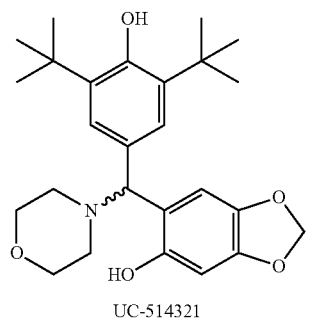 [SMILES: CC(C)(C)c1cc(C(c2cc3c(cc2O)OCO3)N2CCOCC2)cc(C(C)(C)C)c1O]

UC-514321

Mechanistically, the disclosed TET1-signaling inhibitors directly target STAT3/5, which are direct upstream regulators of TET1 transcription. Remarkably, compared to currently available JAK/STAT inhibitors (e.g., Pacritinib, KW-2449, Stattic, and sc-355979), the compounds (NSC-370284 and UC-514321) exhibit a much higher selectivity and also a higher efficacy in targeting TET1-high AML, which likely due to the unique property of our TET1-signaling inhibitor as they directly bind to the DNA-binding domain (DBD) of STAT3/5, interfere with the binding of STAT3/5 to TET1 promoter region, and thereby repress the transcription of TET1. Moreover, both NSC-370284 and UC-514321 exhibit a synergistic effect with daunorubicin in treating TET1-high AML cells in vitro and in vivo. Notably, NSC-370284-resistant THP-1 AML cells are even more sensitive to daunorubicin than parental THP-1 cells. Taken together, these findings highlight the therapeutic potential of targeting TET1, a key oncogenic epigenetic regulator related to DNA demethylation, in AML. The data also reveal that STAT3 and STAT5 are direct upstream regulators of TET1 and are suitable targets to suppress TET1 signaling. The data suggest that application of small-molecule compounds that selectively and effectively target the STAT/TET1 signaling, particularly in combination with standard chemotherapy agents, represents an effective novel therapeutic strategy for the treatment of TET1-high AML (including MLL-rearranged AML and t(8;21) AML), which accounts for approximately 30% of total AML cases. Moreover, these effective inhibitors can also be employed as tool compounds in both basic and translational research to selectively target the STAT/TET1 signaling axis and suppress 5hmC globally.

Structural analysis suggested a potential direct binding of NSC-370284 to the conserved DBD of STAT3 or STAT5. Such binding and the binding sites were identified by use of NMR chemical shift perturbation (CSP). Complex formation with compound NSC-370284 induced extensive CSPs at the isoleucine (Ile) residues of STAT3 at 1:2 of protein: ligand molar ratio.

Based on the structure of compound NSC-370284, structural analogs were explored using BioVia Pipeline Pilot (Version 8.5.0.200) against the University of Cincinnati Compound Library, a collection of approximately 360,000 compounds. The most structurally similar compounds were selected to explore the Structure Activity Relationships (SAR) (Tables A and B). The Table A compounds disclosed herein share the core aryl amine benzodioxole scaffold with NSC-370284, varying primarily in the amine substituents and in the aryl substituents.

Accordingly, provided herein are methods of treating a subject suffering from a condition characterized by overexpression of TET1, which comprise administering to the subject an effective amount of a compound, or pharmaceutically acceptable salt thereof, having the Formula: wherein:

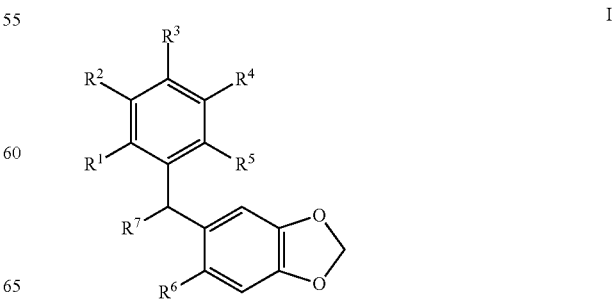

$R^1$, $R^2$, $R^3$, $R^4$, and $R^5$ are each independently selected from the group consisting of H, hydroxyl, alkyl, alkoxy, amine, halo, and trifluoromethyl, and wherein any two adjacent moieties of $R^1$, $R^2$, $R^3$, $R^4$, and $R^5$ may come together to form a heterocyclic ring;

$R^6$ is H or hydroxyl; and $R^7$ is selected from H,

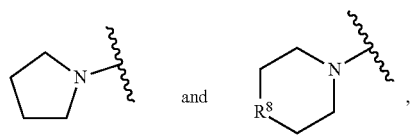

and wherein $R^8$ is C or O.

In certain embodiments, the condition characterized by over-expression of TET1 is a hematopoietic malignancy. In a specific embodiment, the condition is acute myeloid leukemia (AML). In a very specific embodiment, the condition is TET1-high AML.

In some embodiments, alkyl comprises straight or branched chain unsubstituted or substituted C1-C12 alkyl groups. In other embodiments, alkyl comprises straight or branched chain unsubstituted or substituted C1-C6 alkyl groups. In other embodiments, alkyl comprises straight or branched chain unsubstituted or substituted C1-C4 alkyl groups. In specific embodiments, alkyl is selected from the group consisting of methyl, ethyl, propyl, isopropyl, n-butyl, isobutyl, sec-butyl, and tert-butyl.

In some embodiments, alkoxy comprises straight or branched chain unsubstituted or substituted C1-C12 alkoxy groups. In other embodiments, alkoxy comprises straight or branched chain unsubstituted or substituted C1-C6 alkoxy groups. In other embodiments, alkyl comprises straight or branched chain unsubstituted or substituted C1-C4 alkoxy groups. In specific embodiments, alkoxy is selected from the group consisting of methoxy, ethoxy, propoxy, butoxy, and pentyloxy. In a very specific embodiment, alkoxy comprises methoxy and ethoxy.

In certain embodiments, $R^1$, $R^2$, $R^3$, $R^4$, and $R^5$ are each independently selected from H, hydroxyl, methyl, ethyl, methoxy, ethoxy, amine, halo, and trifluoromethyl. In certain embodiments, any two adjacent $R^1$, $R^2$, $R^3$, $R^4$, and $R^5$ may come together to form a heterocyclic ring. In such embodiments, the heterocyclic ring may be a 5- or 6-membered ring. In specific embodiments, the heterocyclic ring formed by any two adjacent $R^1$, $R^2$, $R^3$, $R^4$, and $R^5$ is selected from the group consisting of azole, dioxole, and dioxolane.

Suitable Formula I compounds for use in the methods and compositions disclosed herein include any of the analogs set forth in Table A, alone or in combination. In specific embodiments, the Formula I compound is 6-{[4-Hydroxy-3,5-bis(2-methyl-2-propanyl)phenyl](4-morpholinyl) methyl}-1,3-benzodioxol-5-ol (UC-514321) or 6-(1-Pyrrolidinyl(3,4,5-trimethoxyphenyl)methyl)-1,3-benzodioxol-5-ol (NSC-370284).

TABLE A

Formula I Compounds

| Compound Number | Structure | Lab Reference Number (NSC or UC number) | MW | Formula |
|---|---|---|---|---|
| 1 | 6-{1-Pyrrolidinyl[4-(trifluoromethyl)phenyl]methyl}-1,3-benzodioxol-5-ol | 765626 | 365.3463 | |
| 2 | 6-[4-Morpholinyl(3,4,5-trimethoxyphenyl)methyl]-1,3-benzodioxol-5-ol | 517451 | 403.4257 | |
| 3 | 6-[(2-Hydroxy-3-methoxyphenyl)(4-morpholinyl)methyl]-1,3-benzodioxol-5-ol | 472619 | 359.3731 | |

TABLE A-continued

Formula I Compounds

| Compound Number | Structure | Lab Reference Number (NSC or UC number) | MW Formula |
|---|---|---|---|
| 4 | 6-[1-Pyrrolidinyl(2,4,6-trimethoxyphenyl)methyl]-1,3-benzodioxol-5-ol | 472616 | 387.4263 |
| 5 | 6-((4-(Dimethylamino)phenyl)(4-morpholinyl)methyl)-1,3-benzodioxol-5-ol | 517463 | 356.4156 |
| 6 | 6-[(2-Methoxyphenyl)(4-morpholinyl)methyl]-1,3-benzodioxol-5-ol | 472585 | 343.3737 |
| 7 | 6-{piperidino[4-(trifluoromethyl)phenyl]methyl}-1,3-benzodioxol-5-ol | 943568 | 379.3729 |
| 8 | 6-((2,4-Dimethoxyphenyl)-4-morpholinylmethyl)-1,3-benzodioxol-5-ol | 472591 | 373.3997 |
| 9 | 2-[1,3-Benzodioxol-5-yl(4-morpholinyl)methyl]-4-methylphenol | 514329 | 327.3743 |
| 10 | 6-[(2,3-Dimethoxyphenyl)(4-morpholinyl)methyl]-1,3-benzodioxol-5-ol | 472587 | 373.3997 |

TABLE A-continued

Formula I Compounds

| Compound Number | Structure | Lab Reference Number (NSC or UC number) | MW Formula |
|---|---|---|---|
| 11 | 6-{morpholino[4-(trifluoromethyl)phenyl]methyl}-1,3-benzodioxol-5-ol | 943336 | 381.3457 |
| 12 | 6-[1,3-Benzodioxol-5-yl(4-morpholinyl)methyl]-1,3-benzodioxol-5-ol | 514341 | 355.3844 |
| 13 | 6-{[4-Hydroxy-3,5-bis(2-methyl-2-propanyl)phenyl](4-morpholinyl)methyl}-1,3-benzodioxol-5-ol | 514321 | 441.5598 |
| 14 | 6-[4-Morpholinyl(2,3,4-trimethoxyphenyl)methyl]-1,3-benzodioxol-5-ol | 472606 | 403.4257 |
| 15 | 6-[(4-Fluorophenyl)(4-morpholinyl)methyl]-1,3-benzodioxol-5-ol | 943337 | 331.3382 |
| 16 | 6-{[4-(Dimethylamino)phenyl](1-pyrrolidinyl)methyl}-1,3-benzodioxol-5-ol | 514318 | 340.4162 |

TABLE A-continued

Formula I Compounds

| Compound Number | Structure | Lab Reference Number (NSC or UC number) | MW Formula |
|---|---|---|---|
| 17 | 6-(3,4,5-Trimethoxybenzyl)-1,3-benzodioxol-5-ol | 514328 | 318.3212 |
| 18 | 6-{[4-(Dimethylamino)phenyl](1-piperidinyl)methyl}-1,3-benzodioxol-5-ol | 491129 | 354.4427 |
| 19 | 6-((2-Hydroxyphenyl)(4-morpholinyl)methyl)-1,3-benzodioxol-5-ol | 472589 | 329.3472 |
| 20 | 6-[(2,3-Dimethoxyphenyl)(1-pyrrolidinyl)methyl]-1,3-benzodioxol-5-ol | 472610 | 357.4003 |
| 21 | 6-[1,3-Benzodioxol-5-yl(4-morpholinyl)methyl]-1,3-benzodioxol-5-ol | 514363 | 357.3573 |
| 22 | 6-[(2-Hydroxy-3-methoxyphenyl)(1-pyrrolidinyl)methyl]-1,3-benzodioxol-5-ol | 472614 | 343.3737 |
| 23 | 6-[(2,4-Dimethoxyphenyl)(1-pyrrolidinyl)methyl]-1,3-benzodioxol-5-ol | 472607 | 357.4003 |
| 24 | 6-[1,3-Benzodioxol-5-yl(1-pyrrolidinyl)methyl]-1,3-benzodioxol-5-ol | 517453 | 341.3579 |

TABLE A-continued

Formula I Compounds

| Compound Number | Structure | Lab Reference Number (NSC or UC number) | MW Formula |
|---|---|---|---|
| 25 | 6-[(2-Methoxyphenyl)(1-pyrrolidinyl)methyl]-1,3-benzodioxol-5-ol | 472617 | 327.3743 |
| 26 | 6-[(2,4-Dimethoxyphenyl)(1-piperidinyl)methyl]-1,3-benzodioxol-5-ol | 472595 | 371.4269 |
| 27 | 6-(1-Pyrrolidinyl(3,4,5-trimethoxyphenyl)methyl)-1,3-benzodioxol-5-ol | 370284 | |

TABLE B

Additional analogs of NSC-370284

| Compound Number | Structure | Lab Reference Number | MW Formula |
|---|---|---|---|
| 28 | 4-Hydroxy-3-[(6-hydroxy-1,3-benzodioxol-5-yl)(3,4,5-trimethoxyphenyl)methyl]-2(5H)-furanone | 514315 | 416.3781 |
| 29 | 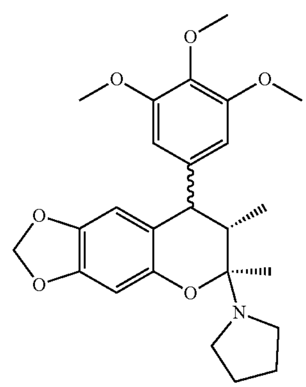 [SMILES: COc1cc(C2c3cc4c(cc3O[C@](C)(N3CCCC3)[C@H]2C)OCO4)cc(OC)c1OC] | 517461 | 441.5167 |
| 30 | 1-[(7-Methoxy-1,3-benzodioxol-5-yl)methyl]azepane | 378752 | 263.3321 |

Also provided herein are methods of treating a subject suffering from a condition characterized by over-expression of TET1, the method comprising administering to the subject an effective amount of a compound, or a pharmaceutically acceptable salt thereof, as set forth in Table B.

TABLE B-continued

Additional analogs of NSC-370284

| Compound Number | Structure | Lab Reference Number | MW Formula |
|---|---|---|---|
| 31 | 4,5-Dimethoxy-2-[4-morpholinyl(3,4,5-trimethoxyphenyl)methyl]phenol | 517447 | 419.4682 |

In certain embodiments, the Formula I or Table B compounds disclosed herein are administered with a second anti-cancer agent to provide a synergistic or enhanced efficacy or inhibition of cancer cell growth. For example, the Formula I or Table B compounds of the present disclosure can be administered in combination with a chemotherapeutic agent including, for example, cytarabine, cladribine, fludarabine, topotecan, doxorubicin, daunorubicin, epirubicin, idarubicin, decitabine, azacitidine, all-trans-retinoic acid, arsenic trioxide, gemtuzumab ozogamicin, midostaurin, nelarabine, clofarabine, dasatinib, imatinib, ponatinib, JQ1, methotrexate, corticosteroids, histamine dihydrochloride, interleukin 2, and combinations thereof. In some embodiments, the Formula I or Table B compound is co-administered with the second anti-cancer agent. In certain embodiments, "co-administered" means a Formula I or Table B compound is administered together with a second anti-cancer agent in the same unit dosage. In other embodiments, "co-administered" means a Formula I or Table B compound and a second anti-cancer agent are administered in separate dosage forms, concurrently or consecutively.

Pharmaceutical Compositions

Provided herein are compositions comprising an effective amount of a compound according to Formula I or Table B, or a pharmaceutically acceptable salt thereof, and a pharmaceutically acceptable carrier.

It will be appreciated that the Formula I or Table B compounds disclosed herein can be administered to a patient or subject either alone or as part of a pharmaceutical composition. The Formula I or Table B compounds can be administered to patients either orally, rectally, parenterally (intravenously, intramuscularly, or subcutaneously), intracisternally, intravaginally, intraperitoneally, intravesically, locally (powders, ointments, or drops), or as a buccal or nasal spray.

Compositions comprising the Formula I or Table B compounds of the present disclosure suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active ingredient is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethylene glycols, and the like.

Solid dosage forms such as tablets, dragées, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethylene glycols and fatty acid esters of sorbitan or mixtures of these substances, and the like.

Besides such inert diluents, the compositions can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal or vaginal administrations are preferably suppositories which can be prepared by mixing the compounds of the present invention with suitable non-irritating excipients or carriers such as cocoa butter, polyethylene glycol or a suppository wax, which are solid at ordinary temperatures but liquid at body temperature and therefore, melt in the rectum or vaginal cavity and release the active component.

Dosage forms for topical administration of Formula I or Table B compounds of the present invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

In addition, the Formula I or Table B compounds of the present invention can exist in unsolvated as well as solvated forms with pharmaceutically acceptable solvents such as water, ethanol, and the like. In general, the solvated forms are considered equivalent to the unsolvated forms for the purposes of the present disclosure. Enantiomers and racemates of the Formula I or Table B compounds are also suitable for use in the compositions and methods disclosed herein.

The Formula I or Table B compounds of the present invention can be administered to a patient at dosage levels in the range of about 1.5 mg to about 150 mg per day; it is also possible to administer larger amounts, such as from about 150 mg to 1 g per day. A unit dosage form of Formula I or Table B compounds is an amount which would be administered as a single dose. For a normal human adult having a body weight of about 70 kilograms, a dosage in the range of about 0.2 mg to about 2.0 mg per kilogram of body weight per day is suitable. The specific dosage used, however, can vary. For example, the dosage can depend on a number of factors including the requirements of the patient, the severity of the condition being treated, and the pharmacological activity of the compound being used. The determination of optimum dosages for a particular patient is well known to those skilled in the art. The Formula I or Table B compounds of the present invention can be given in single and/or multiple dosages.

The Formula I or Table B compounds disclosed herein are synthesized using standard organic synthetic techniques known to the ordinary skilled artisan.

EXAMPLES

The following detailed methodology and materials are set forth to support and illustrate particular aspects and embodiments of the invention, and should not be construed as limiting the scope thereof.

Example 1. Chemical Compounds NSC-311068 and NSC-370284 Effectively Inhibit the Viability of TET1-High AML Cells The high expression and oncogenic role of TET1 in AML has been previously reported. In fact, high expression of TET1 was found not only in AML, but also in various tumors including uterine cancer, glioma, etc., and especially, in testicular germ cell malignancies (FIG. 7). This indicates potential oncogenic role of TET1 in many cancers where TET1 expression level is relatively high.

In order to identify chemical compounds that may target TET1 signaling, the drug-sensitivity/gene expression database of a total of 20,602 chemical compounds in the NCI-60 collection of cancer cell samples was searched. Expression levels of endogenous TET1 showed a significant positive correlation with the responsiveness of cancer cells across the NCI-60 panel to 953 compounds (r>0.2; P<0.05). The top 120 with the highest r values were selected and their effects on cell viability of a TET1-high AML cell line, i.e., MONOMAC-6/t(9;11) were tested. Then, the top 20 showing the most significant inhibitory effects (Table 1) were further tested in three other TET1-high AML cell lines including THP-1/t(9;11), KOCL-48/t(4;11) and KASUMI-1/t(8;21) AML cells, along with MONOMAC-6 cells as a positive control (FIG. 8a-e and Table 2).

TABLE 1

Top 20 candidate chemical compounds that showed positive correlation in drug response and TET1 level in NCI-60 collection

| Compound Number | Lab Reference Number | Correlation |
|---|---|---|
| | 652026 | 0.59 |
| | 633268 | 0.551 |
| | 600290 | 0.538 |
| | 82339 | 0.535 |
| | 534 | 0.532 |
| | 624167 | 0.525 |
| | 633272 | 0.525 |
| | 622600 | 0.523 |
| | 628949 | 0.512 |
| | 49512 | 0.51 |
| | 622589 | 0.508 |
| | 122291 | 0.506 |
| | 635297 | 0.506 |
| | 34757 | 0.505 |
| | 625882 | 0.502 |
| | 650738 | 0.501 |
| | 634781 | 0.5 |
| 27 | 370284 | 0.499 |
| | 667730 | 0.499 |
| | 311068 | 0.498 |

TABLE 2

IC50 of the top 20 candidate chemical compounds in MONOMAC-6, THP-1, KOCL-48 and KASUMI-1 cells.

|         | 652026   | 633268   | 600290   | 82339    | 534      | 624167   | 633272   | 622600   | 628949   | 49512    |
|---------|----------|----------|----------|----------|----------|----------|----------|----------|----------|----------|
| MMC6    | 6.88E+04 | 5.36E-02 | 2.21E+04 | 2.05E+01 | 5.03E+00 | 7.35E+04 | 7.90E-01 | 7.35E+04 | 2.53E-04 | 7.46E-05 |
| THP-1   | 1.09E+00 | 1.92E-06 | 8.42E-01 | 6.09E-01 | 7.70E-01 | N/A      | 1.31E+00 | 9.49E-04 | N/A      | 8.30E-03 |
| KOCL-48 | 5.09E+00 | 5.79E-06 | 1.36E+00 | 1.30E+00 | 1.23E+00 | 6.85E-01 | 3.28E-01 | 1.10E-02 | 1.63E-05 | 9.34E-01 |
| KASUMI1 | 3.68E-04 | 4.83E+06 | 2.00E-06 | 2.33E-04 | 6.08E-01 | N/A      | N/A      | 5.79E-06 | 2.47E+00 | 1.56E+00 |
| Average | 1.72E+04 | 1.21E+06 | 5.53E+03 | 5.61E+00 | 1.91E+00 | 3.68E+04 | 8.10E-01 | 1.84E+04 | 8.24E-01 | 6.26E-01 |

|         | 622589   | 122291   | 635297   | 34757    | 625882   | 650738   | 634781   | 370284   | 667730   | 311068   |
|---------|----------|----------|----------|----------|----------|----------|----------|----------|----------|----------|
| MMC6    | 1.22E+00 | 8.93E-01 | 7.59E+00 | 8.09E+01 | 8.28E-01 | 9.58E+00 | N/A      | 3.85E-04 | N/A      | 6.74E-01 |
| THP-1   | N/A      | N/A      | 1.07E-02 | 1.16E-01 | 2.10E-04 | 1.30E+00 | 2.29E+00 | 3.56E-04 | 7.10E+00 | 2.35E-04 |
| KOCL-48 | 5.62E+00 | 4.76E+00 | 2.20E+00 | 8.56E+00 | 1.46E-01 | 2.02E+00 | N/A      | 3.82E-02 | 1.30E+00 | 7.26E-01 |
| KASUMI1 | 2.46E-05 | 3.81E-04 | 4.16E-04 | 2.38E-04 | N/A      | 7.27E-05 | N/A      | 4.93E-06 | 4.93E+00 | 4.20E-06 |
| Average | 2.28E+00 | 1.89E+00 | 2.47E+00 | 2.24E+01 | 3.25E-01 | 3.23E+00 | 2.30E+00 | 9.75E-03 | 4.45E+00 | 3.50E-01 |

It was found that TET1 is highly expressed not only in MLL-rearranged AML as reported previously, but also in AML carrying t(8;21); moreover, depletion of Tet1 expression also significantly inhibited t(8;21) fusion gene-induced colony-forming/replating capacity of mouse bone marrow (BM) progenitor cells (see FIG. 9). Results showed that NSC-311068 and NSC-370284 exhibited the most significant effects in inhibiting cell viability of all four TET1-high AML cell lines, whereas showing no significant inhibition on viability of NB4/t(15;17) AML cells, a control cell line with very low level of TET1 expression (FIG. 1a,b). In the NCI-60 collection, cell lines with relatively higher TET1 expression levels showed more obvious positive correlation between TET1 expression level and activity of both NSC-311068 and NSC-370284, compared to that across the entire NCI-60 panel, whereas cell lines with relatively lower TET1 expression levels exhibited no obvious positive correlation (NSC-311068) or even negative correlation (NSC-370284) (FIG. 8c-d). In TET1-high AML cells, NSC-311068 and 370284 significantly repressed the level of TET1 expression (FIG. 1c), as well as the global 5hmC level (FIG. 1d). In order to rule out the possibility of non-specific toxicity, the dose of NSC-311068 and NSC-370284 was reduced to 25 nM, and gene expression and cell viability 24 hours after treatment were tested. The low dose, short-term treatments again resulted in a significant down-regulation of TET1 transcription, accompanied with a very minor decrease in the viability of MONOMAC-6, THP-1 and KOCL-48 cells (FIG. 1e-f). Thus, it is unlikely that the inhibitory effects of NSC-311068 and NSC-370284 on TET1 expression were due to nonspecific toxicity.

Example 2. NSC-311068 and NSC-370284 Suppress AML Progression In Vivo

Figure 2:
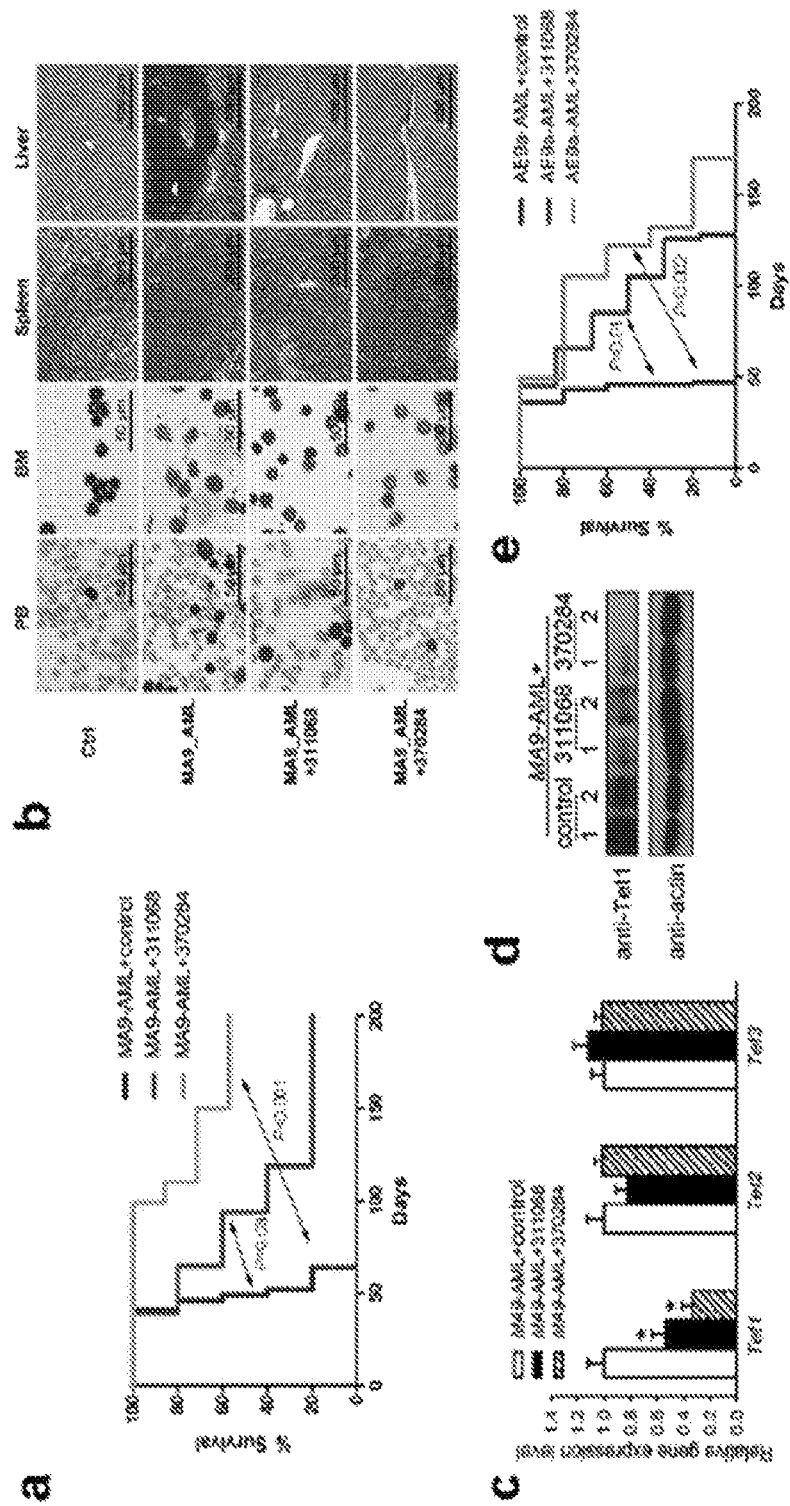
FIG. 2. Therapeutic effects of NSC-311068 and NSC-370284 in AML in vivo. (a) NSC-311068 or NSC-370284 administration inhibits MLL-AF9-AML. The secondary BMT recipient mice were transplanted with leukemic BM blast cells collected from primary MLL-AF9 AML mice. Upon the onset of leukemia, the recipient mice were treated with DMSO (control; n=5), 2.5 mg/kg NSC-311068 (n=5) or NSC-370284 (n=7), i.p., once per day, for 10 days. Kaplan-Meier curves are shown. The P values were determined by log-rank test. (b) Wright-Giemsa staining of mouse peripheral blood (PB) and BM, or hematoxylin and eosin (H&E) staining of mouse spleen and liver of the treated or control leukemic mice. (c,d) Tet1/2/3 gene expression levels (c) or Tet1 protein level (d) in BM blast cells of the treated or control leukemic mice. *, $P<0.05$, two-tailed t-test. Error bar indicates SD of triplicate experiments. (e) Effects of NSC-311068 and NSC-370284 on the AE9a-AML mouse model. The secondary BMT recipient mice were transplanted with leukemic BM blast cells collected from the primary AE9a-AML mice. Upon the onset of leukemia, the recipient mice were treated with DMSO (control; n=5), 2.5 mg/kg NSC-311068 (n=6) or NSC-370284 (n=6), i.p., once per day, for 10 days. Kaplan-Meier curves are shown. The P values were determined by log-rank test.

The potential in vivo therapeutic effects of NSC-311068 and 370284 were then tested with the MLL-AF9 AML model. NSC-311068 and especially 370284 treatments significantly inhibited MLL-AF9-induced AML in secondary BM transplantation (BMT) recipient mice, by prolonging the median survival from 49 days (control) to 94 (NSC-311068) or >200 (NSC-370284) days (FIG. 2a). Notably, 57% (4 out of 7) of the NSC-370284 treated mice were cured, as the pathological morphologies in peripheral blood (PB), BM, spleen and liver tissues all turned to normal (FIG. 2b). The in vivo down-regulation of Tet1 expression by the compounds at both RNA and protein levels was validated by qPCR (FIG. 2c) and Western blotting (FIG. 2d), respectively. In another AML model induced by AML-ETO9a (AE9a)[28], NSC-311068 and NSC-370284 also exhibited remarkable therapeutic effects, with an elongated median survival from 46 days (control) to 95 (NSC-311068) and 122 (NSC-370284) days, respectively (FIG. 2e). Interestingly, NSC-370284 has been reported previously as an analog of the natural product podophyllotoxin (PPT) that was associated with anti-leukemic activity. Given the better therapeutic effect of NSC-370284 in vivo (FIG. 2a,b,e), NSC-370284 was selected for further studies.

Example 3. NSC-370284 Suppresses TET1 Expression Through Targeting STAT3/5

Figure 3:
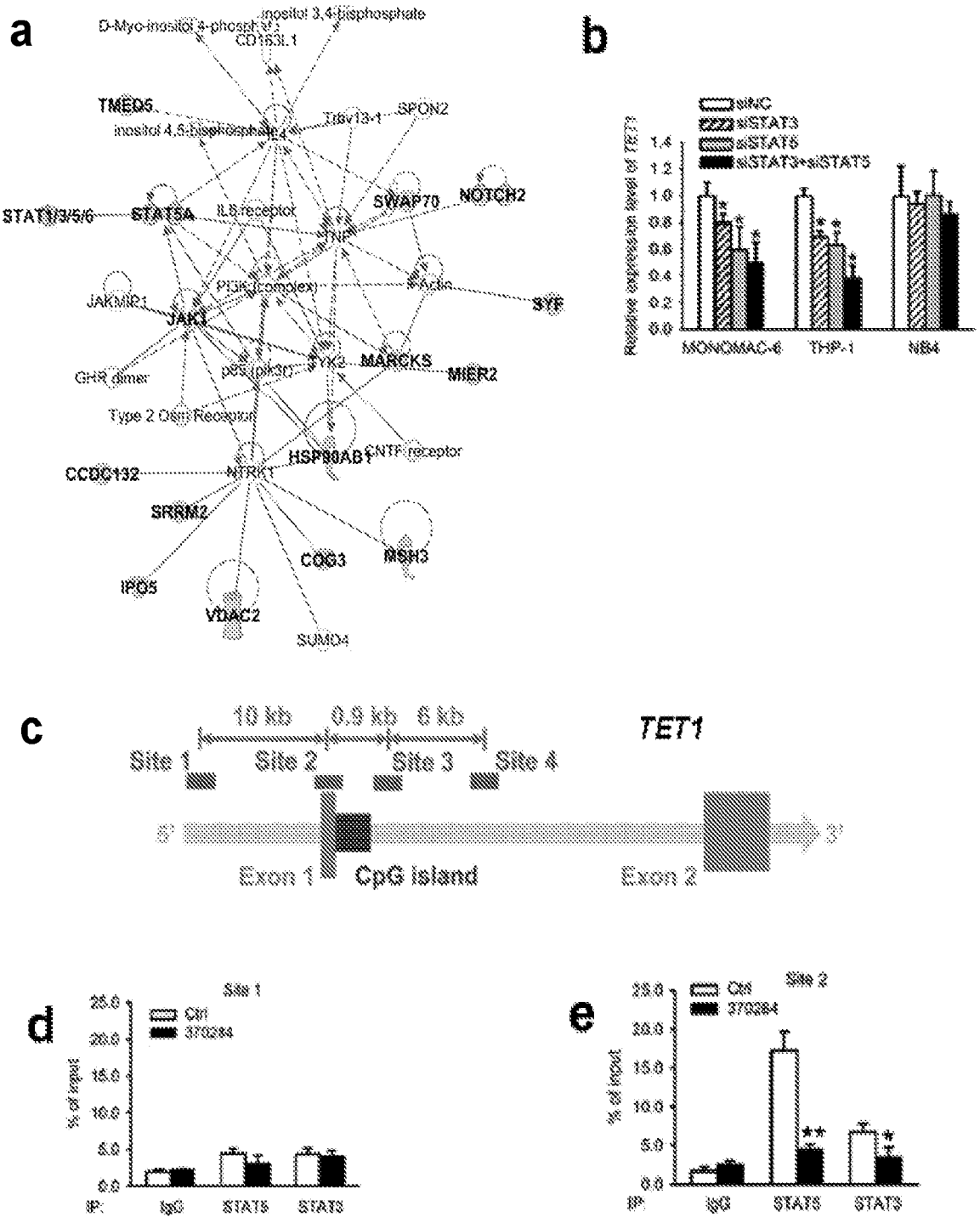
FIG. 3. STAT3 and STAT5 are potential direct targets of NSC-370284 in AML. (a) A top network identified with IPA involving all the 14 genes carrying recurrent mutations in THP-1 NSC-370284-resistant clones. Genes with mutations are labeled in bold font. (b) Knockdown of STAT3 and/or STAT5 reduces TET1 level. MONOMAC-6, THP-1 and NB4 cells were electroporated with control siRNA (siNC), siSTAT3, siSTAT5 or a combination of siSTAT3 and siSTAT5. TET1 expression level was detected by qPCR 48 hrs post-transfection. (c) Four genomic sites designed for ChIP-qPCR analysis to identify potential binding sites of STAT3 and STAT5 on TET1 promoter and other regions. (d-h) MONOMAC-6 cells (d-g) were treated with DMSO control or 500 nM NSC-370284. ChIP-qPCR assay was carried out 48 hrs after drug treatment. Enrichment of STAT3, STAT5, or IgG at the TET1 promoter region and other regions are shown. NB4 cells (h) were applied as a negative control. (i) Predicted binding of DNA (upper panel) or NSC-370284 (lower panel) with the DNA-binding domain (DBD) that is conserved between STAT3 and STAT5 proteins, from docking study on PDB ID 1bg1 using MolSoft ICM. (j) The association between STAT3 and NSC-370284 as determined with NMR chemical shift perturbation (CSP). Complex formation with compound 370284 induced extensive CSPs at the Be residues of STAT3 at 1:2 of protein:ligand molar ratio (red peaks: free STAT3; green peaks: STAT3-NSC-370284 complex). The CSP occurs at residues adjacent to the DNA-binding site (I464), and residues at or near the DBD. (k) NSC-370284 suppresses the binding between STAT3 and TET1 CpG island, as determined through EMSA. *, $P<0.05$; **, $P<0.01$, two-tailed t-test. Error bar indicates SD of triplicate experiments.
Figure 3:
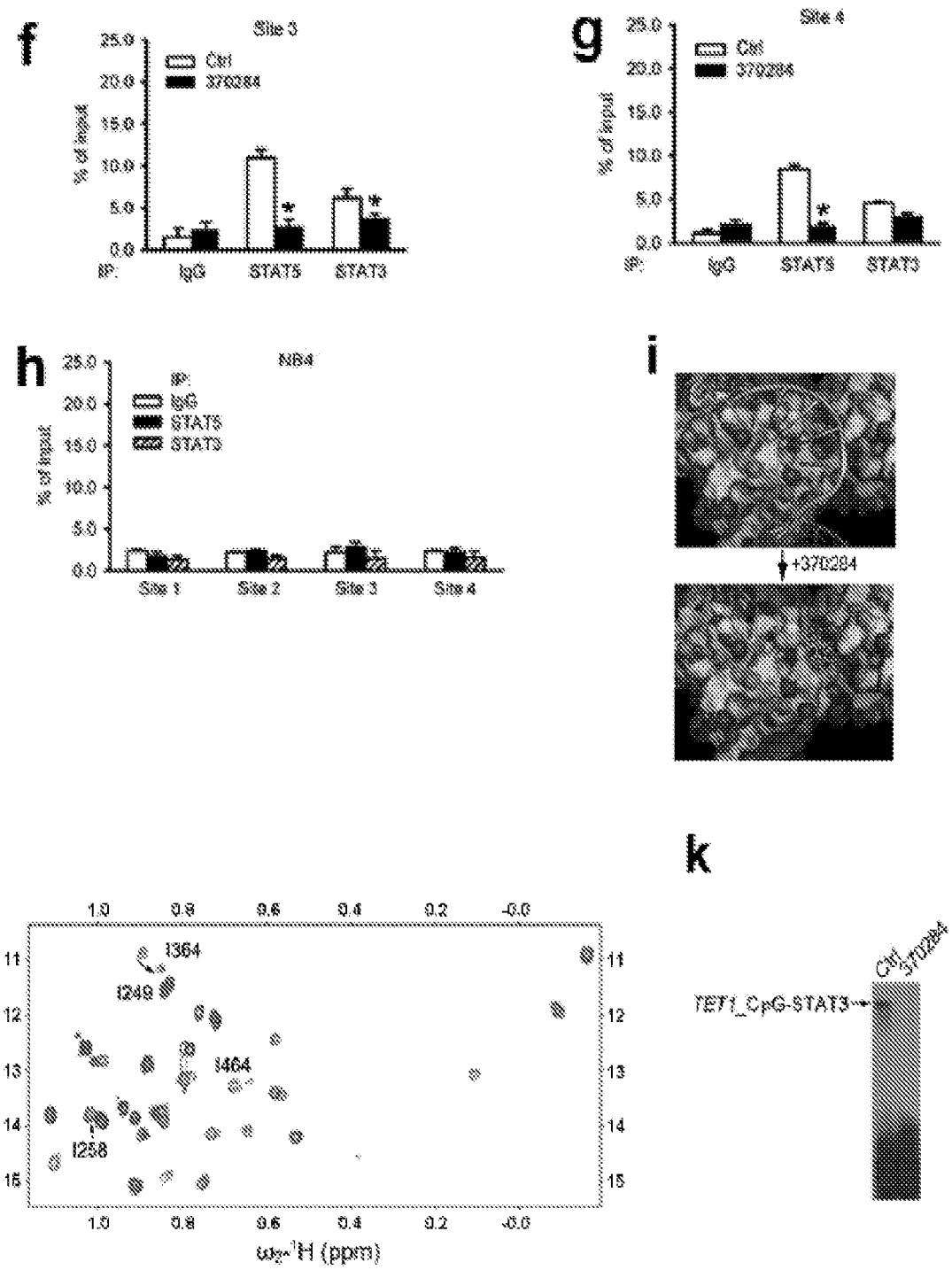

To decipher the molecular mechanism by which NSC-370284 represses TET1 expression, the strategy developed by Kapoor and colleagues EMREF 31 was adapted to identify direct target protein(s) of NSC-370284. Briefly, multiple-drug-resistant clones were established and transcriptome sequencing was conducted to find mutations in each clone; the assumption was that the critical components of the signaling of the drug target(s) would have a high chance to carry mutations in drug-resistant clones. To this end, THP-1 AML cells were treated with high to moderate concentration of NSC-370284 for over 100 days and then a set of individual drug-resistant THP-1 single clones were isolated (see the representatives in FIG. 10a). These drug-resistant cells showed no significant down-regulation of TET1 expression upon treatment of NSC-370284 (FIG. 10b). Through RNA-seq of 6 of the NSC-370284-resistant clones, recurrent mutations were found in 14 genes in at least two individual clones. Ingenuity pathway analysis (IPA) was used to analyze biological relationships amongst the 14 mutated genes (Table 3). The top five networks identified by IPA, based on Fisher's exact test, are associated with cancer, hematological disease, immunological disease, etc. (Table 4). The top one network identified by IPA involving all of the 14 genes is closely associated with the JAK/STAT5 pathway (FIG. 3a). A number of these genes have been reported to be associated with the JAK/STAT signaling. It is likely that mutations in such genes may overcome NSC-370284-mediated inhibitory effect on AML cell viability/growth, and thereby confer drug resistance to the AML clones. To test this, we chose JAK1 and MSH3 as two representatives and cloned constructs carrying the JAK1$^{A893G}$ mutant or the MSH3$^{V600I}$ mutant that was detected in our drug-resistant THP-1 cells (Table 3). As expected, forced expression of either mutant at least partially reversed the inhibitory effect of NSC-370284 on AML cell viability (FIG. 10c-d).

TABLE 3

Genes with recurrent mutations in THP-1 NSC-370284-resistant clones.

| Gene | ExonicFunc | AAChange | Chr | Pos | Ref | Obs |
|---|---|---|---|---|---|---|
| MSH3 | nonsynonymous SNV | NM_002439:c.G1798A:p.V600I | chr5 | 80057399 | G | A |
| COG3 | nonsynonymous SNV | NM_031431:c.A1903G:p.I635V | chr13 | 46090371 | A | G |
| IPO5 | nonsynonymous SNV | NM_002271:c.G2524A:p.V842I | chr13 | 98668012 | G | A |
| TMED5 | nonsynonymous SNV | NM_001167830:c.T415C:p.W139R | chr1 | 93621913 | A | G |
| HSP90AB1 | nonsynonymous SNV | NM_001271969:c.T593G:p.V198G | chr6 | 44217836 | T | G |
| CCDC132 | nonsynonymous SNV | NM_017667:c.A1877T:p.N626I | chr7 | 92952944 | A | T |
| MIER2 | nonsynonymous SNV | NM_017550:c.G1396A:p.A466T | chr19 | 307339 | C | T |
| SYF2 | nonsynonymous SNV | NM_207170:c.G206C:p.W69S | chr1 | 25554653 | C | G |
| VDAC2 | nonsynonymous SNV | NM_001184823:c.G826C:p.G276R | chr10 | 76990688 | G | C |
| SWAP70 | nonsynonymous SNV | NM_0150555:c.A1527T:p.E509D | chr11 | 9769576 | A | T |
| NOTCH2 | frameshift deletion | NM_001200001:c.17_18del:p.6_6del | chr1 | 120612003 | GG | — |
| MARCKS | nonsynonymous SNV | NM_002356:c.G130C:p.D44H | chr6 | 114180886 | G | C |
| SRRM2 | frameshift deletion | NM_016333:c.5444_5445del:p.1815_1815del | chr16 | 2815973 | GG | — |
| JAK1 | nonsynonymous SNV | NM_002227:c.A893G:p.E298G | chr1 | 65332646 | T | C |

TABLE 4

Top 5 signaling pathways and associated diseases of the genes with recurrent mutations in THP-1 NSC-370284-resistant clones.

(a) Top 5 canonical pathways involving the genes with recurrent mutations in THP-1 NSC-370284-resistant clones.

| Name of Canonical Pathways | P value |
|---|---|
| IL-22 Signaling | 1.17E−04 |
| Role of JAK family kinases in IL-6-type Cytokine Signaling | 1.27E−04 |
| IL-9 Signaling | 2.37E−04 |
| Oncostatin M Signaling | 2.37E−04 |
| Role of JAK2 in Hormone-like Cytokine Signaling | 2.37E−04 |

(b) Top 5 diseases and disorders involving the genes with recurrent mutations in THP-1 NSC-370284-resistant clones.

| Diseases and Disorders | P value range |
|---|---|
| Cancer | 4.84E−02~2.14E−05 |
| Hematological Disease | 4.26E−02~2.14E−05 |
| Immunological Disease | 4.26E−02~2.14E−05 |
| Organismal Injury and Abnormalities | 4.84E−02~2.14E−05 |
| Developmental Disorder | 4.13E−02~2.14E−05 |

Consistent with this, it was shown that knockdown of STAT3 and/or STAT5 in MONOMAC-6 and THP-1 cells resulted in a down-regulation of TET1, but not TET2 or TET3 (FIG. 3b and FIG. 10c-f). Through searching the UCSC Genome Browser (genome.ucsc.edu/index.html), it was found that STAT5 has a putative binding site (ttccct-gaacagcttttaca tgtg (SEQ ID NO: 1); the consensus binding motif: ttcnnngaa (SEQ ID NO: 2); FIG. 3c, Site 4) located within the promoter region of TET1 gene, suggesting TET1 might be a direct target of the STAT proteins. The direct binding of STAT3 and STAT5 on the TET1 loci was further validated in MONOMAC-6 cells through chromatin immunoprecipitation (ChIP)-qPCR assay, and such binding could be disturbed by NSC-370284 treatment (FIG. 3c-g). In NB4 cells, no significant binding of STAT3 or STAT5 on the TET1 loci was detected (FIG. 3h). JAK1 was known as the upstream activator of the STAT pathway. Surprisingly, knockdown of TET1 resulted in a reduction of JAK1 transcription in AML cells (FIG. 10i). ChIP-qPCR results showed direct binding of TET1 to the JAK1 promoter (FIG. 10j). The above findings suggest JAK/STAT pathway promotes TET1 transcription via direct binding of STAT3/5 to the TET1 promoter, and TET1 also binds to the JAK1 promoter and activates JAK1 transcription. This indicates a feedback loop between JAK1/STAT/TET1 in AML.

Structural analysis suggested a potential direct binding of NSC-370284 to the conserved DNA-binding domain (DBD) of STAT3 or STAT5 (FIG. 3i). Such binding and the binding sites were identified by use of NMR chemical shift perturbation (CSP). Complex formation with compound NSC-370284 induced extensive CSPs at the isoleucine (Ile) residues of STAT3 at 1:2 of protein:ligand molar ratio (FIG. 3j). The CSPs occurred at residues adjacent to the DNA-binding site (I464) and those at or near DBD (FIG. 3j), indicating that compound NSC-370284 binds to STAT3 at or near DBD. The association between STAT3 and the TET1 CpG island was further verified with electrophoretic mobility shift assay (EMSA); this association could almost be completely blocked by NSC-370284 (FIG. 3k). In order to test whether NSC-370284 also inhibits the phosphorylation of STAT3 and STAT5, MONOMAC-6 cells were treated with NSC-370284 for a series of time points. Western blotting showed no significant alterations of the levels of STAT3 and STAT5 phosphorylation (FIG. 10k). It is likely NSC-370284 mainly competes against DNA for STAT binding, but not does suppress STAT activation.

These results indicate that STAT3 and STAT5 are direct targets of NSC-370284, which can interfere with the binding of STAT3/5 to TET1 promoter region and thereby suppress the transcription of TET1. Similarly, a previous study also reported a compound C48, a structural analog of NSC-370284, can bind directly to the DNA binding domain of STAT3 protein and lead to apoptosis and inhibition of tumor cell growth.

Notably, the inhibitory effects of NSC-370284 on the expression of other STAT5 target genes, such as HIF2a, IL2RA and FRA2, were not as obvious as that on TET1 (FIG. 10l). The basal enrichment of STAT5 on the promoter of HIF2a, IL2RA or FRA2 was very low, as compared with that on the TET1 promoter; and the interruption by NSC-370284 on such association was much less obvious (FIG. 10m). The very weak, if any, basal affinity of STAT5 with most of its target genes' promoters without cytokine stimulation (e.g., IL-2, IL-3 or EPO) has been reported before. Therefore, these results revealed a very strong enrichment of STAT3/5 on TET1 promoter (FIG. 3e-g, 3k; FIG. 10l-m). Moreover, results indicate that different from typical STAT inhibitors that target STAT kinase activity, NSC-370284 may exert its function mainly through interfering with the binding of STAT protein to the DNA regions which have relatively higher basal affinity to STATs, like the TET1 promoter, in AML cells.

Figure 4:
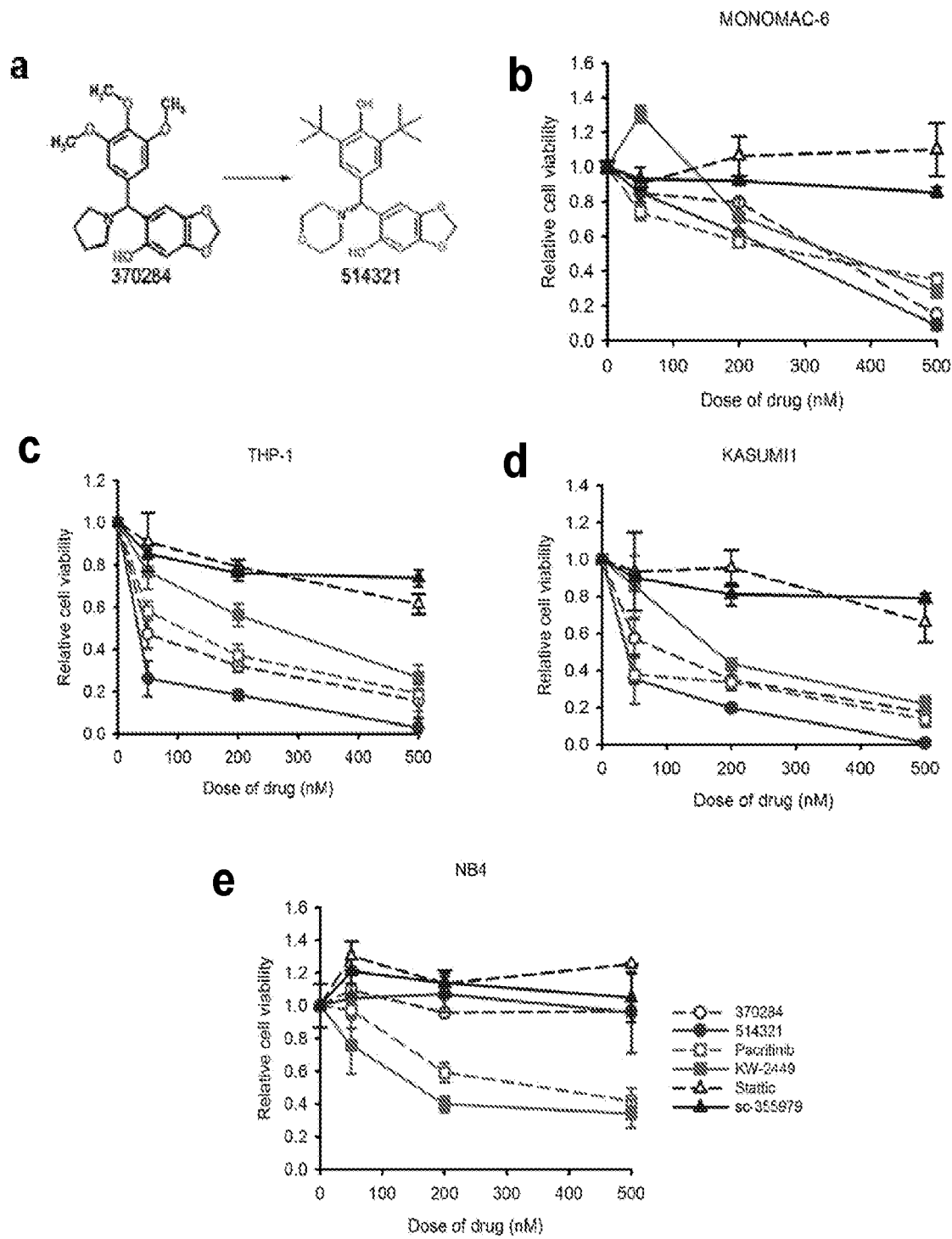
FIG. 4. Effects of UC-514321, a structural analog of NSC-370284 in treating AMLs. (a) Structures of NSC-370284 and UC-514321. (b-e) Effects of NSC-370284, UC-514321 and other JAK/STAT pathway inhibitors, i.e., Pacritinib, KW-2449, Stattic and sc-355979, on the viability of AML cell lines MONOMAC-6 (b), THP-1 (c), KASUMI1 (d) and NB4 (e). Cells were treated with drugs at indicated doses. Cell viability was detected by MTS 48 hrs post-treatment. Error bar indicates SD of triplicate experiments. (f,g) Enhanced therapeutic effect of UC-514321, relative to NSC-370284, in treating TET1-high AMLs in vivo. Secondary BMT recipient mice were transplanted with primary leukemic BM cells with MLL-AF9 (f) or AML-ETO9a (g). Upon the onset of leukemia, the recipient mice were treated with DMSO (control) (n=5), 2.5 mg/kg NSC-370284 (n=6) or UC-514321 (n=6), i.p., once per day, for 10 days. Kaplan-Meier curves are shown. The P values were determined by log-rank test. (h,i) Therapeutic effect of NSC-370284 and UC-514321 in treating MLL-AF10 AML (h) and FLT3-ITD/NPM1$^{mut}$ AML (i). Secondary BMT recipient mice were transplanted with primary leukemic BM cells with MLL-AF10 or FLT3-ITD/NPM1$^{mut}$. Upon the onset of leukemia, the recipient mice were treated with DMSO (control) (n=6 for each model), 2.5 mg/kg NSC-370284 (n=5) or UC-514321 (n=5), i.p., once per day, for 10 days. Kaplan-Meier curves are shown. The P values were determined by log-rank test. (j) Wright-Giemsa staining of mouse PB and BM, or H&E staining of mouse spleen and liver of MLL-AF9 AML secondary BMT recipients with or without drug treatment.
Figure 4:
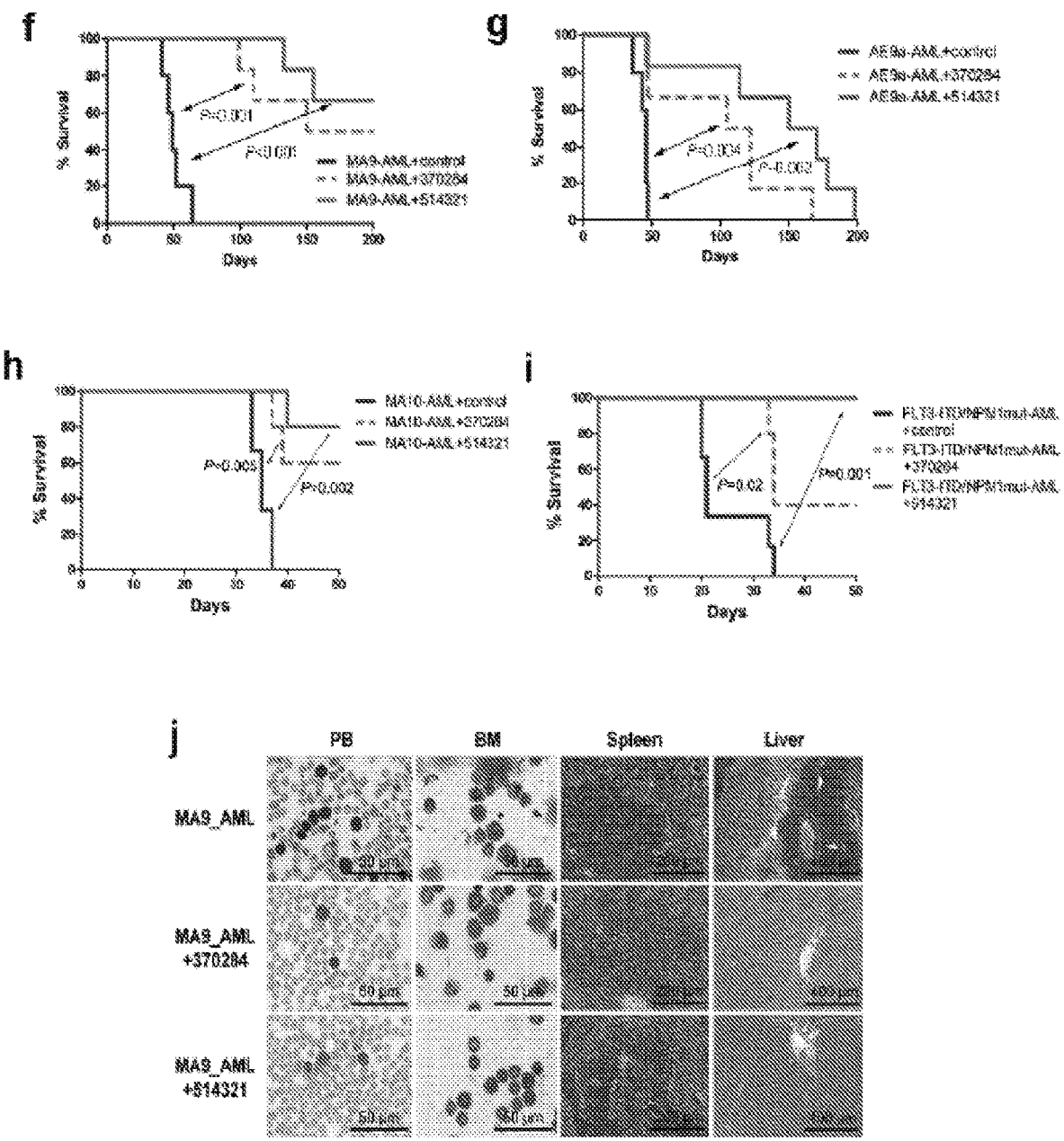

Enhanced therapeutic efficacy of NSC-370284 analog UC-514321 Based on the structure of compound NSC-370284, structural analogs were explored using BioVia Pipeline Pilot (Version 8.5.0.200) against the University of Cincinnati Compound Library, a collection of approximately 360,000 compounds. The most structurally similar compounds were selected to explore the Structure Activity Relationships (SAR) (Tables A and B). The Table A compounds share the core aryl amine benzodioxole scaffold with NSC-370284, varying primarily in the amine substituents and in the aryl substituents. Results of MTS assays showed that one of the analog compounds, UC-514321, most significantly repressed MONOMAC-6 cell viability (FIG. 4a and FIG. 11). UC-514321 showed an enhanced effect in repressing the viability of TET1-high AML (including MONOMAC-6, THP-1, and KASUMI-1) cells, as compared with NSC-370284 and other JAK/STAT inhibitors, e.g. Pacritinib, KW-2449, STAT3/5 inhibitor Stattic, or STAT5 inhibitor sc-355979 (FIG. 4b-d). Similar to NSC-370284, UC-514321 showed no inhibitory effect on the viability of TET1-low AML (i.e., NB4) cells (FIG. 4e). Thus, the anti-tumor effect of UC-514321 is also TET1-signaling dependent. Notably, the STAT3/5 specific inhibitors Stattic and sc-355979 did not show significant inhibitory effects on the viability of these AML cells, probably because their $IC_{50}$ values are much higher than 500 nM, the maximum concentration we tested. Overall, compared to other JAK and/or STAT inhibitors, UC-514321 is more effective and selective in inhibiting the viability of TET1-high AML cells.

Moreover, compared to the parental compound (NSC-370284), UC-514321 also showed an improved therapeutic effect in AML mouse models in vivo. In MLL-AF9-AML mice, UC-514321 prolonged median survival from 49 days (control) to >200 days, better than NSC-370284 (FIG. 4f). In the AE9a-AML model, the median survival of UC-514321 treated mice was 160 days, much longer than the control (46 days) and NSC-370284 (114 days) treated groups (FIG. 4g). Thus, in both AML animal models, UC-514321 prolonged the median survival over 3 folds (FIG. 4f-g). Moreover, the therapeutic effects of NSC-370284 and UC-514321 were tested in two other AML models, i.e., MLL-AF10 AML and FLT3-ITD/NPM1$^{mut}$ AML. NSC-370284 prolonged median survival of MLL-AF10 leukemic mice from 35 days to >50 days, and that of FLT3-ITD/NPM1$^{mut}$ leukemic mice from 21 days to 34 days. UC-514321 showed an even better therapeutic effect, as it prolonged median survival of both MLL-AF10 and FLT3-ITD/NPM1$^{mut}$ leukemic mice to >50 days (FIG. 4i,j). Notably, UC-514321 treatment cured 66.7% (4 out of 6) of the MLL-AF9 AML mice (FIG. 4f,h), and none of the UC-514321-treated FLT3-ITD/NPM1$^{mut}$ AML recipients developed full-blown AML within 50 days (FIG. 4j).

Figure 5:
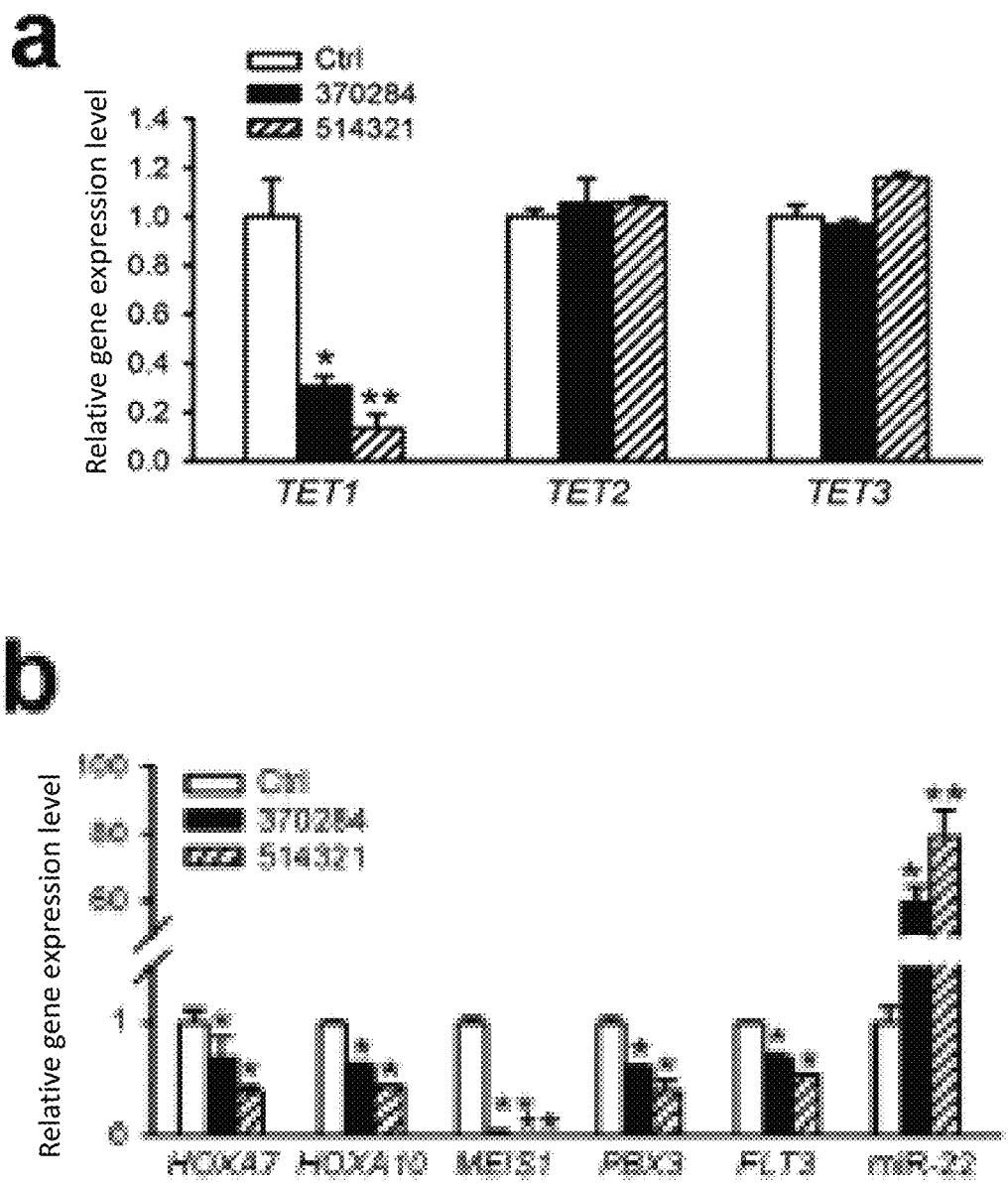
FIG. 5. NSC-370284 and UC-514321 function as TET1-transcription inhibitors in TET1-high AMLs and their anti-leukemic effects are TET1-dependent. (a) NSC-370284 and UC-514321 inhibit the transcription of TET1, but not TET2 or TET3. MONOMAC-6 cells were treated with DMSO control, 500 nM NSC-370284 or UC-514321 for 48 hrs. Gene expression levels are shown. (b) Effects of NSC-370284 and UC-514321 in downstream gene targets of TET1. (c) NSC-370284 and UC-514321 repressed global 5hmC level in MONOMAC-6 cells. (d) The association between STAT3 and UC-514321 as determined with NMR CSPs. (e-h) MONOMAC-6 cells were treated with DMSO control, 500 nM NSC-370284 or UC-514321. ChIP-qPCR assay was carried out 48 hrs after drug treatment. Enrichment of STAT3, STAT5, or IgG at the TET1 promoter region and other regions are shown. (i-l) Functions of NSC-370284 and UC-514321 depend on Tet1 expression. BM progenitor cells of wild-type or Tet1$^{-/-}$ mice were retrovirally transduced with MLL-AF9. Infected cells were treated with NSC-370284, UC-514321 and other JAK/STAT pathway inhibitors, i.e., Pacritinib, KW-2449, Stattic and sc-355979, at indicated doses (i,j) or at a particular dose (i.e., 500 nM.
Figure 5:
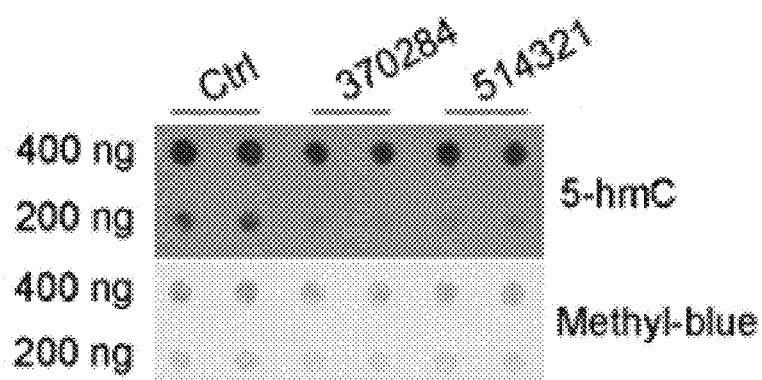
Figure 5:
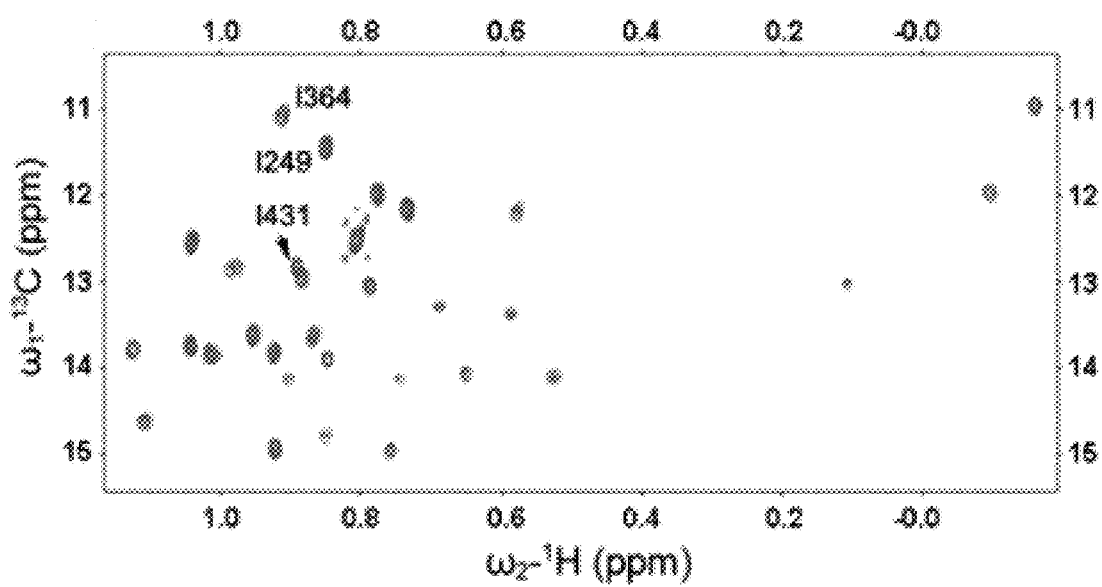
Figure 5:
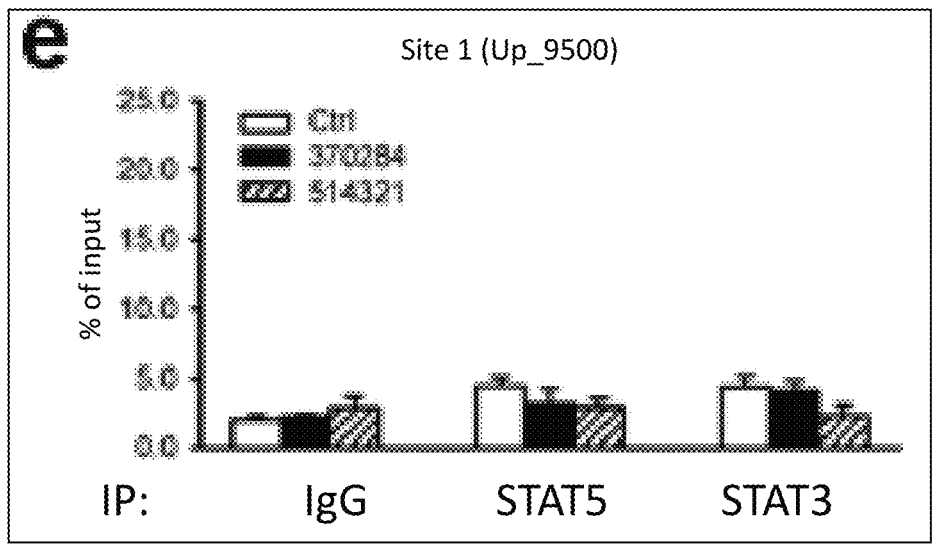
Figure 5:
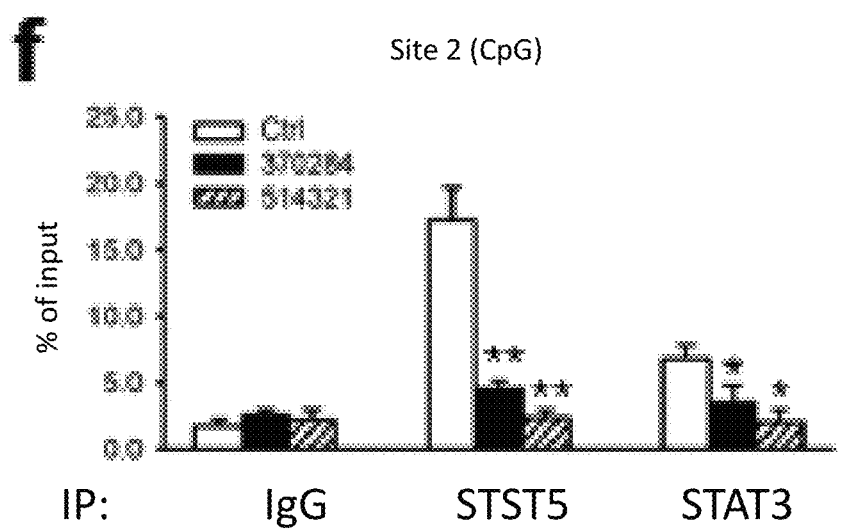
Figure 5:
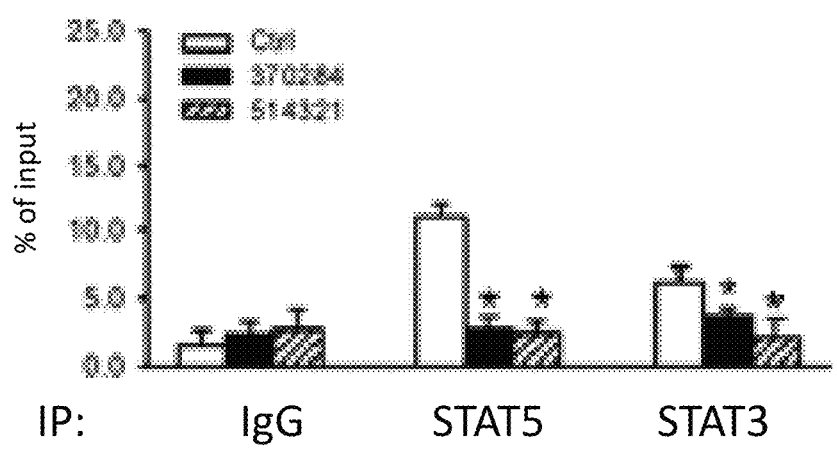
Figure 5:
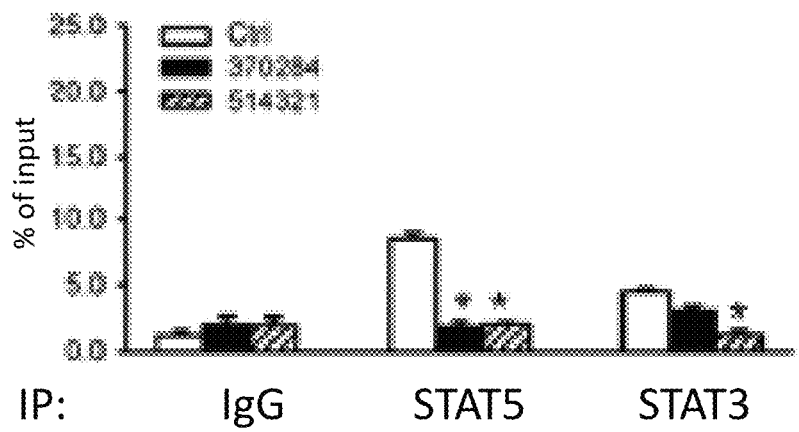
Figure 5:
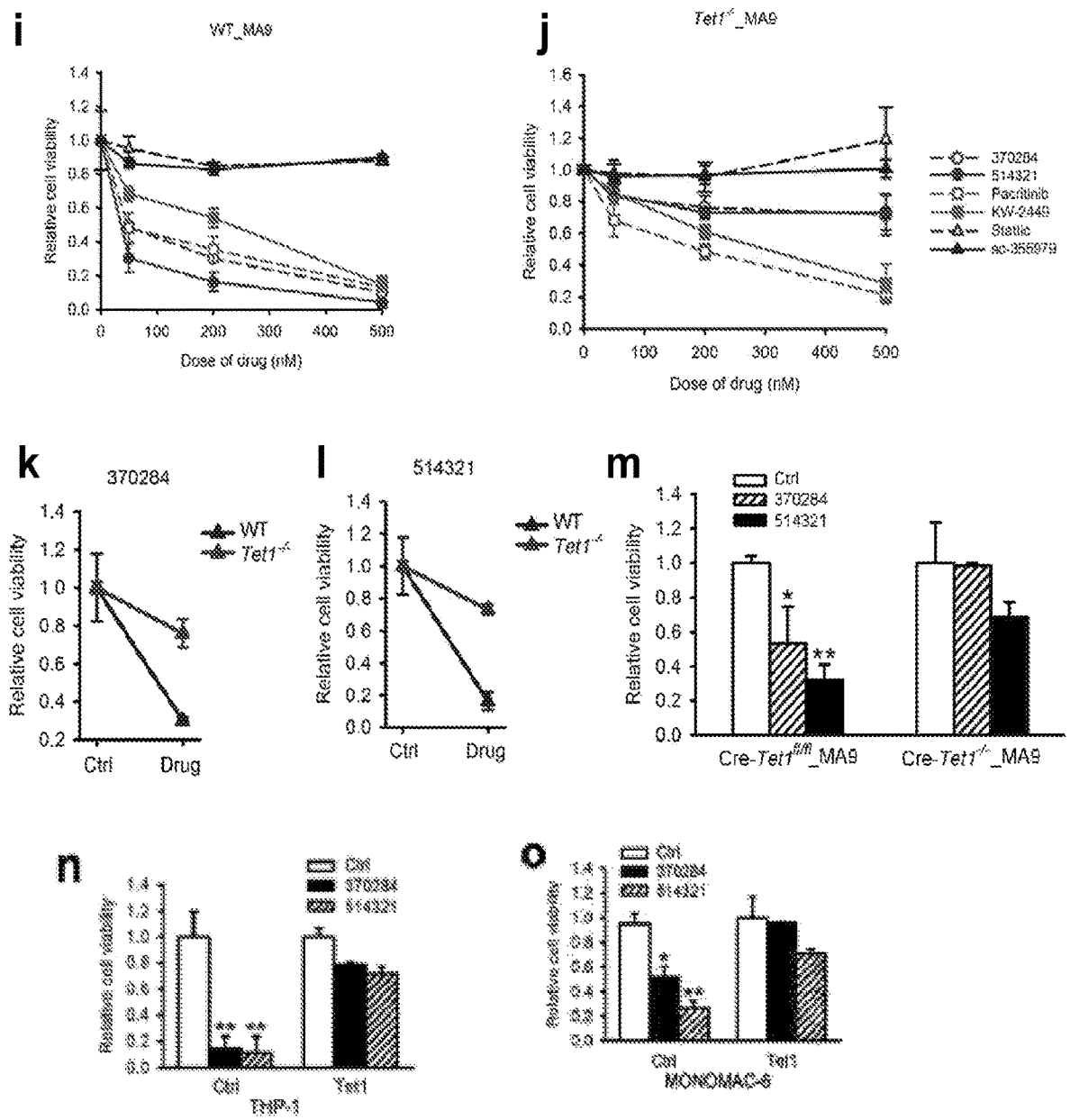

To determine whether the mechanism underlying UC-514321 function is similar to that of NSC-370284, a series of mechanistic studies were performed. As expected, similar to NSC-370284, UC-514321 significantly repressed expression of TET1, but not TET2 or TET3, along with the down-regulation of putative target genes of TET1, e.g., HOXA7, HOXA10, MEIS1, PBX3 and FLT3, etc., and the up-regulation of negative targets, e.g., miR-22, in MONOMAC-6 cells (FIG. 5a,b). Notably, compared to NSC-370284, UC-514321 exhibited an enhanced effect on the changes in gene expressions (FIG. 5a,b). Both NSC-370284 and UC-514321 significantly reduced global 5hmC levels (FIG. 5c), and their inhibitory effect was further confirmed with genome-wide 5hmC-seq in AML cells. We found both NSC-370284 and UC-514321 treatments resulted in around 75% reduction of 5hmC peak enrichment in the whole genome (FIG. 12a-c). Similar to NSC-370284 (FIG. 3j), the largest CSPs induced by UC-514321 treatment were also observed at the residues adjacent to DNA-binding surface (I431) and those near or in DBD (FIG. 5d). In contrast, Stattic and sc-355979 target the STAT SH2 domain. Therefore, both NSC-370284 and UC-514321 induce CSP at residues at or adjacent to the DNA-binding surface, and thus they likely interfere with STAT protein's binding to DNA. This was further verified with ChIP-qPCR assays. In MONOMAC-6 cells, UC-514321 treatment also resulted in a remarkable repression on the binding of STAT3/5 to TET1 promoter, even more significant than NSC-370284 at the CpG region (FIG. 5e-h).

Figure 1:
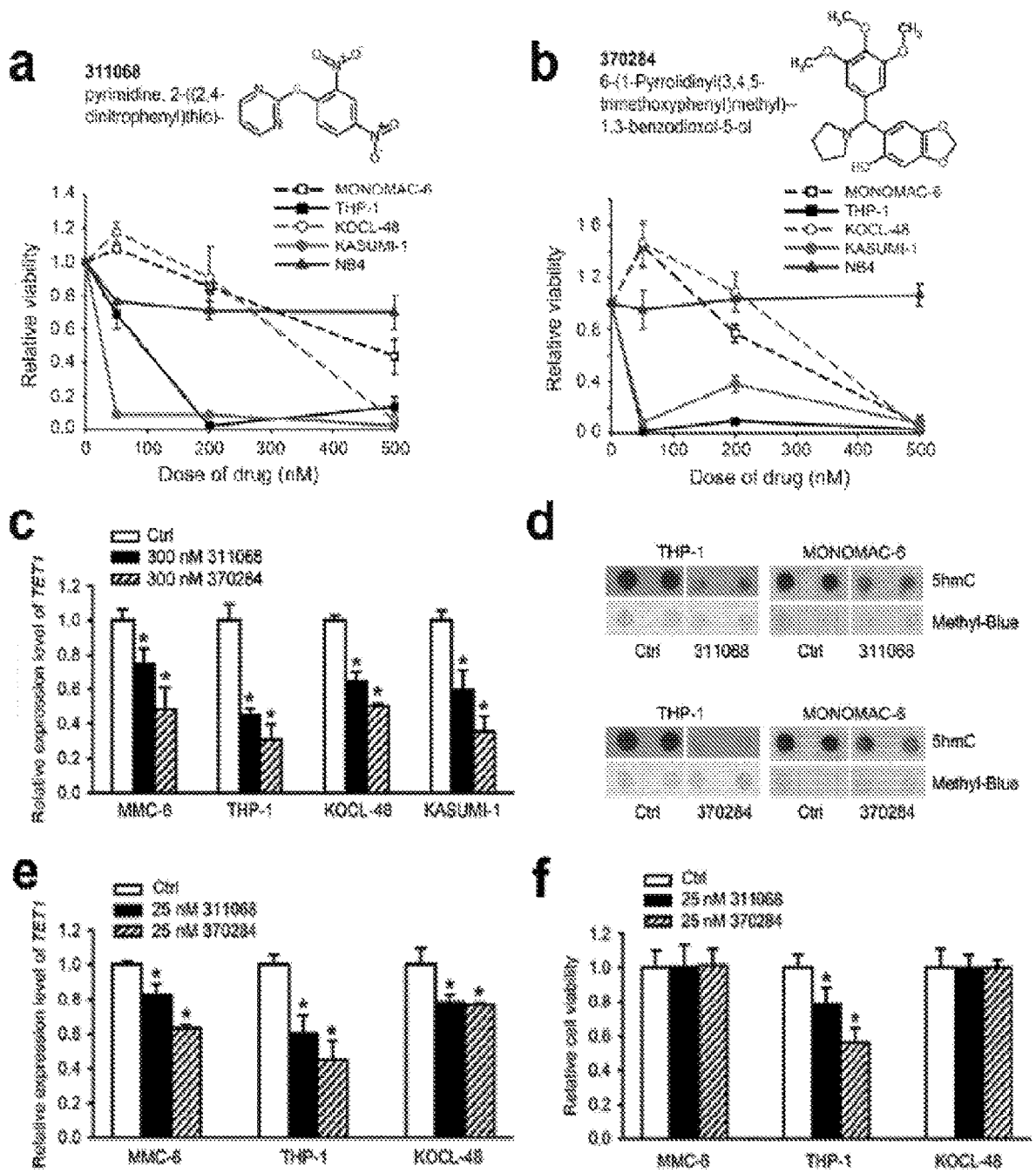
FIG. 1. NSC-311068 and NSC-370284 suppress the viability of AML cells with high TET1 level. (a-b) TET1-high AML cell lines including MONOMAC-6, THP-1, KOCL-48, and KASUMI-1, along with a TET1-low control cell line (i.e., NB4), were treated with NSC-311068 (a) or NSC-370284 (b) at indicated doses (0, 50, 200, 500 nM). Cell viability was analyzed by MTS 48 hours post-treatment. (c) Repression of TET1 expression by NSC-311068 and NSC-370284 in AML cell lines. Cells were treated with DMSO, or 300 nM NSC-311068 or NSC-370284. TET1 expression levels were detected by qPCR 48 hrs post-treatment. (d) NSC-311068 and NSC-370284 (both at 300 nM) repressed global 5hmC level in THP-1 (left panels) and MONOMAC-6 (right panels) cells. (e,f) MONOMAC-6, THP-1 and KOCL-48 cells were treated with DMSO, or 25 nM NSC-311068 or NSC-370284. TET1 expression levels (e) and cell viability (f) were detected 24 hrs post-treatment. *, $P<0.05$, two-tailed t-test. MM6, MONOMAC-6. Error bar indicates SD of triplicate experiments.

In wild-type mouse BM progenitor cells transduced with MLL-AF9, treatment with NSC-370284 or UC-514321 resulted in a remarkable repression of cell viability, and no such inhibition was observed in Tet1 deficient counterpart cells (FIG. 5i-1). Other JAK/STAT inhibitors (i.e. Pacritinib, KW-2449, Stattic, and sc-355979) showed no significant differences in affecting cell viability between wild-type and Tet1 deficient cells (FIG. 5i,j and FIG. 13a-d). Further, in MLL-AF9-transduced BM progenitor cells from conditional Tet1 knockout mice, NSC-370284 and UC-514321 also showed no significant effect in inhibiting the viability of the cells with induced Tet1 deficiency (FIG. 5m and FIG. 13e). In addition, a pLenti-puro vectored Tet1 construct was created and transduced into THP-1 and MONOMAC-6 cells, which showed that ectopic expression of Tet1 sufficiently reversed the inhibitory effects of NSC-370284 and UC-514321 and restored viability of the AML cells (FIG. 5n-o). Taken together with the selective effect of NSC-370284 on TET1-high AML cell lines (FIG. 1b), the above results suggest that the anti-leukemic effects of NSC-370284 and UC-514321 are TET1-signaling dependent.

Example 5. NSC-370284 and UC-514321 Show No Obvious Toxicity in Healthy Mice

Cell viability and apoptosis assays were first carried out to assess the effects of NSC-370284 and UC-514321 on normal hematopoietic stem/progenitor cells (HSPCs; herein we used c-Kit$^+$ BM cells) in vitro. Remarkably, NSC-370284 or UC-514321 treatment dramatically suppressed the viability of AML cells, but not that of normal HSPCs (FIG. 14a). In addition, the compounds significantly increased apoptosis in AML cells, but not in normal HSPCs (FIG. 14b). Thus, these two compounds showed no obvious toxicity on normal HSPCs. This is consistent with endogenous Tet1 expression pattern, as AML cells with MLL-AF10 or FLT3-ITD/NPM1$^{mut}$ have relatively higher Tet1 expression levels, as compared with normal HSPCs (FIG. 14c).

To assess potential toxicity of NSC-370284 and UC-514321 in normal tissues, especially the hematopoietic system, in vivo, NSC-370284 or UC-514321 were injected into normal C57BL/6 mice and assessed potential acute toxicity (24 hrs) or long-term (200 days) toxicity after 10 succeeding days' administration of either NSC-370284 or UC-514321. Body weights, spleen and liver weights, white blood cell (WBC) counts, all peripheral blood lineages, as well as granulocytes (Mac1$^+$Gr1$^+$, monocytes (Mac1$^+$Gr1$^-$) and progenitor (c-Kit$^+$) lineages of BM cells were assessed, and no evidence of either acute or long-term toxicity was observed (FIG. 15, 16 and Table 5).

TABLE 5

Acute or long-term effects of NSC-370284 and UC-514321 on mouse blood cell differentiation after 10 consecutive days' administration

| | WBC (K/µl) | NE (K/µl) | LY (K/µl) | MO (K/µl) | EO (K/µl) | BA (K/µl) | RBC (M/µl) | PLT (K/µl) |
|---|---|---|---|---|---|---|---|---|
| (a) Acute effects (24 hrs post the last administration) of NSC-370284 and UC-514321 on mouse blood cell differentiation. | | | | | | | | |
| DMSO | 10.32 ± 3.2 | 1.97 ± 0.65 | 7.49 ± 2.6 | 0.27 ± 0.02 | 0.2 ± 0.08 | 0.07 ± 0.03 | 8.61 ± 1.86 | 552.32 ± 131.22 |
| 370284 | 8.35 ± 2.34 | 1.67 ± 0.21 | 6.74 ± 2.55 | 0.22 ± 0.14 | 0.15 ± 0.01 | 0.05 ± 0.05 | 8.55 ± 3.34 | 460.21 ± 42.42 |
| 514321 | 8.64 ± 3.68 | 1.94 ± 0.56 | 6.54 ± 2.7 | 0.27 ± 0.1 | 0.14 ± 0.12 | 0.07 ± 0.05 | 9.54 ± 0.74 | 559.43 ± 116.9 |
| Normal range | 1.8-10.7 | 0.1-2.4 | 0.9-9.3 | 0.0-0.4 | 0.0-0.2 | 0.0-0.2 | 6.36-9.42 | 592-2972 |
| (b) Long-term effects (200 days post the last administration) of NSC-370284 and UC-514321 on mouse blood cell differentiation. | | | | | | | | |
| DMSO | 11.97 ± 3.26 | 1.83 ± 0.51 | 9.79 ± 2.85 | 0.22± 0.09 | 0.06 ± 0.04 | 0.01 ± 0.01 | 8.5 ± 1.59 | 954.95 ± 99.25 |
| 370284 | 10.34 ± 2.19 | 2.26 ± 0.54 | 7.68 ± 1.55 | 0.31± 0.03 | 0.11 ± 0.01 | 0.03 ± 0.02 | 7.38 ± 1.7 | 929.62 ± 154.61 |
| 514321 | 11.89 ± 1.64 | 2.11 ± 0.44 | 8.55 ± 1.18 | 0.25 ± 0.05 | 0.1 ± 0.01 | 0.07 ± 0.04 | 7.07 ± 0.42 | 681.56 ± 402.64 |
| Normal range | 1.8-10.7 | 0.1-2.4 | 0.9-9.3 | 0.0-0.4 | 0.0-0.2 | 0.0-0.2 | 6.36-9.42 | 592-2972 |

Note:
Normal C57BL/6 mice were treated with PBS (control), 2.5 mg/kg NSC-370284 or UC-514321, i.p., once every day for 10 days. Shown are data collected at the indicated time points (i.e. 24 hrs (a) or 200 days (b)) post the last i.p. injection of the chemical compounds or DMSO control (DMSO). WBC = white blood cells; NE = neutrophils; LY = lymphocytes; MO = monocytes; EO = eosinophils; BA = basophils; RBC = red blood cells; PLT = platelets. Means ± Standard deviations are shown.

The maximum tolerated dose of NSC-370284 and UC-514321 in mice was 65-85.6 mg/kg (Table 6). The LD50 was around 123 mg/kg (Table 6). Analysis of the pharmacokinetic properties of UC-514321 showed that the compound had a half-life of 11.02 hrs in mouse blood (Table 7; FIG. 17).

TABLE 6

Maximum tolerated dose (MTD) and median lethal dose ($LD_{50}$) of NSC-370284 and UC-514321.

| Animals | Routes | Dose | Number of Death | Number of Exposure |
|---|---|---|---|---|
| NSC-370284 ($LD_{50}$ = 123.1 mg/kg) | | | | |
| C57BL/6 | I.P. | 200 mg/kg | 10 | 10 |
| | I.P. | 150 mg/kg | 6 | 10 |
| | I.P. | 113.5 mg/kg | 3 | 10 |
| | I.P. | 85.6 mg/kg | 1 | 10 |
| | I.P. | 65 mg/kg | 0 | 10 |
| UC-514321 ($LD_{50}$ = 123.7 mg/kg) | | | | |
| C57BL/6 | I.P. | 200 mg/kg | 10 | 10 |
| | I.P. | 150 mg/kg | 7 | 10 |
| | I.P. | 113.5 mg/kg | 2 | 10 |
| | I.P. | 85.6 mg/kg | 1 | 10 |
| | I.P. | 65 mg/kg | 0 | 10 |

TABLE 7

Blood pharmacokinetic parameters of UC-514321 (data provided as mean ± SD).

| Pharmacokinetic Parameters | C57BL/6 Mice I.P. 15 mg/kg |
|---|---|
| Half-life (h) | 11.02 ± 2.51 |
| $AUC_{0-\infty}$ (µg · h · $mL^{-1}$) | 29.35 ± 2.75 |
| Mean Residence Time (h) | 16.12 ± 1.79 |

TABLE 7-continued

Blood pharmacokinetic parameters of UC-514321 (data provided as mean ± SD).

| | |
|---|---|
| Volume of Distribution (L · $kg^{-1}$) | 21.66 ± 1.74 |
| Clearance (L · $kg^{-1}$ · $h^{-1}$) | 1.36 ± 0.08 |

Example 6. Synergistic Effect with Standard Chemotherapy

Long-term treatment with a drug may cause drug resistance in patients, and thus combinatory therapy is often required. To treat AMVL cells that have gained resistance to inhibitors, the effects of a set of first-line AMVL chemotherapy drugs including daunorubicin (DNR), cytarabine (AraC), all-trans retinoic acid (ATRA), azacytidine (AZA), and decitabine (DAC) on the viability of parental THIP-1 cells and three NSC-370284-resistant clones were investigated (FIG. 6a and FIG. 18a-d). Strikingly, all 3 drug-resistant clones appeared to be much more sensitive to DNR than the parental control (FIG. 6a). NSC-370284 or UC-514321 works synergistically with DNR on inhibiting the viability of THIP-1 and KASUMI-1 cells (FIG. 6b,c). The synergistic effect between NSC-370284 or 514321 and the standard chemotherapy (i.e. the "5+3" regimen) was further validated in vivo. Even administrated at relative low doses, the combinatorial treatment of NSC-370284+DNR/AraC or UC-514321+DNR/AraC showed a better therapeutic effect in curing MLL-AF9 AML, as the combinatorial administrations cured 83.3% (5 out of 6) of the AML mice (FIG. 6d,e).

Through analysis of the RNA-seq data of the NSC-370284 resistant clones and parental cells, we showed that several gene clusters that are known to be associated with drug response, especially response to topoisomerase II inhibitors such as DNR, are enriched in NSC-370284 resistant cells. These gene clusters include JAK/STAT signaling, G2M checkpoint, MYC targets and E2F targets, etc. A potential DNR sensitizing mechanism might be through targeting G2M checkpoint. It was shown that overexpression of CDC25, a key phosphatase of G2M checkpoint control, could significantly sensitize tumor cells to doxorubicin treatment. RNA-seq data showed increased CDC25 levels in NSC-370284 resistant AML clones, relative to the parental cells. Also consistent is the enrichment of G2M checkpoint gene cluster in control samples relative to NSC-370284 treated samples. The activation of JAK/STAT pathway might, directly or indirectly, contribute to G2M checkpoint abnormality, as reported previously by others. Therefore, very likely the deregulation of G2M checkpoint in NSC-370284 resistant clones at least partially explains why the resistant clones, compared to the parental AML cells, are more sensitive to DNR treatment. Overall, the combination of NSC-370284 or UC-514321 with DNR represents a promising therapeutic strategy that will not only be effective in treating patients with TET1-high AMLs at relative low doses, but also avoid the occurrence of resistance to NSC-370284 or UC-514321.

Example 7. Materials and Methods

The Maintenance, Monitoring, and End-Point Treatment of Mice

C57BL/6 (CD45.2), B6.SJL (CD45.1) mice were purchased from the Jackson Lab (Bar Harbor, ME, USA) or Harlan Laboratories, Inc (Indianapolis, IN, USA). Both male and female mice were used for the experiments. All laboratory mice were maintained in the animal facility at University of Cincinnati or University of Chicago. All experiments on mice in the research protocol were approved by Institutional Animal Care and Use Committee (IACUC) of University of Cincinnati or University of Chicago. All methods were performed in accordance with the relevant guidelines and regulations. The maintenance, monitoring, and end-point treatment of mice were conducted as described previously (Jiang, X., et al., miR-22 has apotent anti-tumour role with therapeutic potential in acute myeloid leukaemia, *Nat Commun* 7: 11452 (2016); Jiang, X., et al., Eradication of Acute Myeloid Leukemia with FLT3 Ligand-Targeted miR-150 Nanoparticles, *Cancer Res* 76; 4470-80 (2016); Jiang, X., et al. Blockade of miR-150 Maturation by MLL-Fusion/MYCILIN-28 Is Required for MLL-Associated Leukemia, *Cancer Cell* 22; 524-35 (2012)). Randomization, allocation concealment and blind outcome assessment were conducted throughout all the experiments.

Mouse Bone Marrow Transplantation (BMT) Followed with Drug Treatment

Secondary mouse BMT was carried out as described previously. Upon the onset of leukemia (when mice had an engraftment (CD45.1) of over 20% and/or white blood cell counts higher than $4 \times 10^9$/L, usually 10 days post transplantation), the recipient mice were injected with DMSO control, 2.5 mg/kg NSC-311068, NSC-370284 or UC-514321, i.p., once per day, for ten days. For the "5+3" and NSC-370284 or UC-514321 combination treatment experiment, after the onset of AML, the recipient mice were treated with PBS control, or NSC-370284 or UC-514321 alone, i.p., once per day, for ten days or together with the "5+3" treatment. For the "5+3" treatment, AraC (Cytarabine, Bedford Laboratories) and DNR (Daunorubicin, Sigma-Aldrich) were reconstituted with PBS, filtered, and stored in aliquots at −20° C. The "5+3" therapy regimen consists of five consecutive daily doses of 50 mg/kg AraC along with 3 mg/kg DNR daily during the first three days of treatment. Drugs were delivered by tail vein and intraperitoneal injection. Weights were taken daily during treatment and doses were recalculated to ensure the mice received a consistent dose of 50 mg/kg AraC and 3 mg/kg DNR every treatment.

Cell Culture and Drug Treatment

MONOMAC-6, THP-1, KOCL-48, KASUMI-1, ML-2 and NB4 cells were purchased from ATCC (Manassas, VA), and cultured as described previously (Jiang, X., et al. Blockade of miR-150 Maturation by MLL-Fusion/MYC/LIN-28 Is Required for MLL-Associated Leukemia. *Cancer Cell* 22, 524-535 (2012); Li, Z., et al. miR-196b directly targets both HOXA9/MEIS1 oncogenes and FAS tumour suppressor in MLL-rearranged leukaemia. (Li, Z., et al., miR-196b directly targets both HOXA9/MEIS1 oncogenes and FAS tumour suppressor in MLL-rearranged leukaemia, *Nat Commun* 2:688 (2012)). All cell lines were tested for *mycoplasma* contamination yearly using a PCR *Mycoplasma* Test Kit (PromoKine) and were proven to be *mycoplasma* negative. All cell lines were authenticated through STR profiling yearly.

Cell Transfection and Retrovirus Infection siRNAs were transfected into MONOMAC-6 cells with Cell Line Nucleofector Kit V following program T-037, using the Amaxa Nucleofector Technology (Amaxa Biosystems, Berlin, Germany). Experiments were performed 48 h after transfection. Retrovirus infection of mouse BM progenitor cells were conducted as described previously with some modifications. Briefly, retrovirus vectors were co-transfected with pCL-Eco packaging vector (IMGENEX, San Diego, CA) into HEK293T cells using Effectene Transfection Reagent (Qiagen, Valencia, CA) to produce retrovirus. BM cells were harvested from a cohort of 4- to 6-week-old C57BL/6, Tet1$^{-/-}$, or Cre-Tet1$^{fl/fl}$ donor mice after five days of 5-fluorouracil (5-FU) treatment, and primitive hematopoietic progenitor cells were enriched with Mouse Lineage Cell Depletion Kit (Miltenyi Biotec Inc., Auburn, CA). An aliquot of enriched hematopoietic progenitor cells was added to retroviral supernatant together with polybrene in cell culture plates, which were centrifuged at 2,000 g for 2 hours at 32° C. (i.e., spinoculation) and then the medium was replaced with fresh media and incubated for 20 hours at 37° C. Next day, the same procedure was repeated once. Infected cells were grown in RPMI 1640 medium containing 10 ng/mL murine recombinant IL-3, 10 ng/mL IL-6, 100 ng/mL murine recombinant SCF (R&D Systems, Minneapolis, MN), along with 1.0 mg/ml of G418. Experiments were performed 7 days after infection.

RNA Extraction and Quantitative RT-PCR

Total RNA was extracted with the miRNeasy extraction kit (Qiagen) and was used as template for quantitative RT-PCR (qPCR) analysis.

Cell Apoptosis, Viability and Proliferation Assays

These experiments were conducted as described previously (Jiang, X., et al., Blockade of miR-150 Maturation by MLL-Fusion/MYCILIN-28 Is Required for MLL-AssociatedLeukemia, *Cancer Cell* 22:524-35 (2012); Li, Z., et al., miR-196b directly targets both HOXA91MEIS1 oncogenes and FAS tumour suppressor in MLL-rearranged leukaemia,

*Nat Commun* 2:688 (2012)) with ApoLive-Glo Multiplex Assay Kit, or CellTiter 96 AQ$_{ueous}$ Non-Radioactive Cell Proliferation Assay Kit (Promega, Madison, WI).

NMR Chemical Shift Perturbation (CSP)

Specific Ile—methyl labeled STAT3 for NMR studies was prepared as described previously (Byrd, J. C., et al. Repetitive cycles of high-dose cytarabine benefit patients with acute myeloid leukemia and inv(16)(p13q22) or t(16;16) (p13;q22): results from CALGB 8461. (Namanja, A. T., et al., Allosteric Communication across STAT3 Domains Associated with STAT3 Function and Disease-Causing Mutation, *J Mol Biol* 428:579-89 (2016)). For each compound, STAT3 was expressed and purified fresh, and a reference spectrum was acquired. Then, the complexes of STAT3 with each of the compounds in the same buffer as the free STAT3 (reference) sample were prepared and two-dimensional (2D) $^1$H-$^{13}$C-HMQC spectra of STAT3 were acquired. The protein samples contained 20 µM STAT3. Both compounds were added to a final concentration of 40 µM, respectively. All 2D $^1$H-$^{13}$C HMQC spectra were collected with 2048× 128 complex points at 35° C. on the Bruker Ascend 700 spectrometer equipped with a cryoprobe. The spectra were analyzed with the program Sparky (T. D. Goddard and D. G. Kneller, SPARKY 3, University of California, San Francisco).

Chromatin Immunoprecipitation-qPCR (ChIP-qPCR) ChIP assay was conducted as described previously (Barry, S. P., et al., STAT3 modulates the DNA damage response pathway, *Int J Exp Pathol* 91:506-14 (2010)), with SABiosciences Corporation's ChampionChIP One-Day kit (Qiagen, Frederick, MD) following the manufacturer's protocol. Chromatin from MONOMAC-6 cells were cross-linked, sonicated into an average size of ~500 bp, and then immunoprecipitated with antibodies against STAT3 (Santa Cruz, Dallas, TX), STAT5 (BD Biosciences, San Jose, CA), or IgG (Abcam, Cambridge, MA). Purified DNA was amplified by real-time qPCR using primers targeting the promoter of TET1 as described before (Huang, H., et al., TET1 plays an essential oncogenic role in MLL-rearranged leukemia, *Proc Natl Acad Sci USA* 110:11994-99 (2013)). Sequences of qPCR primers are: Site 1 forward: 5'-ACTTTGACCTCC-CAAAGTGCTGGA-3' (SEQ ID NO: 3), reverse: 5'-ACCT-GAGTGATGCTGAGACTTCCT-3' (SEQ ID NO: 4); Site 2 forward: 5'-TTTGGGAACCGACTCCTCACCT-3' (SEQ ID NO: 5), reverse: 5'-TCGGGCAAACTTTC-CAACTCGC-3' (SEQ ID NO: 6); Site 3 forward: 5'-ACGCTGGGCATTTCTGATCCACTA-3' (SEQ ID NO: 7), reverse: 5'-TATTGTGCAGCTCGTTTAGTGCCC-3' (SEQ ID NO: 8); Site 4 forward: 5'-CCATCTCCCGACACACA-3' (SEQ ID NO: 9); reverse: 5'-TTGGCAGTGACCTTGAGA-3' (SEQ ID NO: 10).

Electrophoretic-Mobility Shift Assay (EMSA)

EMSA was conducted with EMSA Assay Kit (Signosis, Santa Clara, CA) according to the manufacturer's protocol with minor modifications. Briefly, purified STAT3 protein was incubated with Biotin-labeled TET1-CPG probe (hot probe) and/or cold probe, and then protein/DNA complexes were separated on a non-denaturing polyacrylamide gel. Bands were detected using Streptavidin-HRP conjugate and a chemiluminescent substrate. The sequences of the TET1-CPG probe are: Forward: 5' Biotin-CCGGTAGGCGTCCTCCGCGACCCGC-3' (SEQ ID NO: 11); Reverse: 5' Biotin-GCGGGTCGCGGAGGACGCC-TACCGG-3' (SEQ ID NO: 12).

Western Blotting

Cells were washed twice with ice-cold phosphate-buffered saline (PBS) and ruptured with RIPA buffer (Pierce, Rockford, IL) containing 5 mM EDTA, PMSF, cocktail inhibitor, and phosphatase inhibitor cocktail. Cell extracts were microcentrifuged for 20 min at 10,000 g and supernatants were collected. Cell lysates were resolved by SDS-PAGE and transferred onto PVDF membranes. Membranes were blocked for 1 hour with 5% skim milk in Tris-buffered saline containing 0.1% Tween 20 and incubated overnight at 4° C. with anti-Tet1 antibody (GT1462, GeneTex, Irvine, CA) or anti-ACTIN antibody (8H10D10, Cell Signaling Technology Inc., Danvers, MA). Membranes were washed 30 min with Tris-buffered saline containing 0.1% Tween-20, incubated for 1 hour with appropriate secondary antibodies conjugated to horseradish peroxidase, and developed using chemiluminescent substrates.

5hmC Labeling Reaction and Dot-Blotting

The 5-hydroxymethylcytosine (5-hmC) labeling reactions and 5hmC dot blotting were performed as described previously (Huang, H., et al. TET1 plays an essential oncogenic role in MLL-rearranged leukemia. *Proc Natl Acad Sci USA* 110, 11994-11999 (2013)). Briefly, 3 jig sonicated genomic DNA (100-500 bp) fragments were incubated in solution containing 50 mM Hepes buffer (pH 7.9), 25 mM MgCl2, 100 jiM UDP-6-N3-Glc, and 1 jiM beta-glucosyltransferase (f3-GT) for 1 hr at 37° C. The CLICK was performed with addition of 150 jiM dibenzocyclooctyne modified biotin into the purified DNA solution, and the reaction mixture was incubated for 2 hrs at 37° C. Six hundred nanograms of labeled genomic DNA samples were spotted on an Amersham Hybond-N+ membrane (GE Healthcare, Little Chalfont, UK). DNA was fixed to the membrane by Stratagene UV Stratalinker 2400 (auto-crosslink). The membrane was then blocked with 5% BSA and incubated with Avidin-HRP (1:40,000) (Bio-Rad, Hercules, CA), and then visualized by enhanced chemiluminescence.

5hmC-Seal Library Construction 100 ng genomic DNA extracted from ML-2 cell were fragmented in 50 jiL Tagmentation buffer at 55° C. Fragmented DNA was purified by Zymo DNA clean&concentrator Kit (Zymo Research, Tustin, CA). Then, the selective 5hmC chemical labeling was performed in 25 jiL glucosylation buffer (50 mM HEPES buffer pH 8.0, 25 mM MgCl2) containing above fragmented DNA, 100 µM N3-UDP-Glc, 1 µM B-GT, and incubated at 37° C. for 2 hr. After purified in 45 µL ddH2O, 1.5 µL DBCO-PEG4-Biotin (Click Chemistry Tools, 4.5 mM stored in DMSO) was added and incubated at 37° C. for 2 hr. The biotin labeled DNA was pulled down by 5 µL C1 Streptavidin beads (Life Technologies, Carlsbad, CA) for 15 min at room temperature. Next, the captured DNA fragments were subjected to 13 cycles of PCR amplification using Nextera DNA sample preparation kit (Illumina, San Diego, CA). The resulting amplified product was purified by 1.0× AMPure XP beads. Input library was made by direct PCR from fragmented DNA without chemical labeling and capture. The libraries were quantified by a Qubit fluorometer (Life Technologies) and sequenced on an Illumina HiSEQ4000 sequencer with paired-end 50-bp reads.

Statistical Software and Statistical Analyses

The gene network was analyzed with Ingenuity Pathway Analysis (Qiagen). The modeling of protein-DNA/chemical compound binding was conducted with Molsoft ICM-Pro (Molsoft L.L.C., San Diego, CA). The t-test, Kaplan-Meier method, and log-rank test, etc. were performed with WinSTAT (R. Fitch Software), GraphPad Prism version 5.00 (GraphPad Software, San Diego, CA), and/or Partek Genomics Suite (Partek Inc). The P-values less than 0.05 were considered as statistically significant. For 5hmC sequencing analysis, illumina sequencing reads were mapped to UCSC hg19 human reference genome using bowtie program. Only uniquely mapped reads were retained for the following data analysis. PCR duplicates were removed using samtools. The identification of 5hmC peaks in each sample was performed using MACS, and an IDR cutoff of 0.01 was used to filter high confident peaks. Peaks from different samples were merged together into a unified catalog of 5hmC enriched regions using HOMER. To visualize sequencing signals in IGV, BigWig files were generated by deepTools with RPKM normalization method. All the data meet the assumptions of the tests, with acceptable variation within each group, and similar variance between groups.

Data Availability

Data referenced in this study are available in The Gene Expression Omnibus. The 5hmC sequencing data is available under GSE97407 (www.ncbi.nlm.nih.gov/geo/query/acc.cgi?token=etodaoikjtwnpgb&acc=GSE97407).

The invention claimed is:

1. A method of treating a subject suffering from a condition characterized by over-expression of Ten-eleven translocation 1 (TET1), wherein the condition comprises TET1-high AML, the method comprising administering to the subject an effective amount of a compound, or a pharmaceutically acceptable salt thereof, having the Formula:

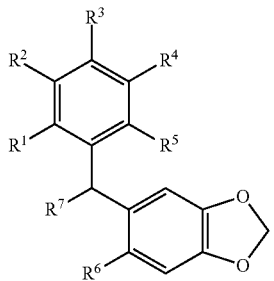

wherein:
$R^1$, $R^2$, $R^3$, $R^4$, and $R^5$ are each independently selected from the group consisting of H, hydroxyl, alkyl, alkoxy, amine, halo, and trifluoromethyl, and wherein any two adjacent moieties of $R^1$, $R^2$, $R^3$, $R^4$, and $R^5$ may come together to form a heterocyclic ring;
$R^6$ is H or hydroxyl; and
$R^7$ is selected from H,

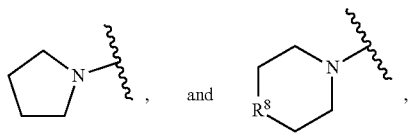

wherein $R^8$ is $CH_2$ or O.

2. The method of claim 1, wherein any two adjacent moieties of $R^1$, $R^2$, $R^3$, $R^4$, and $R^5$ come together to form a heterocyclic ring selected from the group consisting of azole, dioxole, and dioxolane.

3. The method of claim 1, wherein alkyl comprises straight or branched chain C1-C12 alkyl and wherein alkoxy comprises straight or branched chain C1-C12 alkoxy.

4. The method of claim 1, wherein the compound is selected from the group consisting of:
6-{1-Pyrrolidinyl[4-(trifluoromethyl)phenyl]methyl}-1,3-benzodioxol-5-ol;
6-[4-Morpholinyl(3,4,5-trimethoxyphenyl)methyl]-1,3-benzodioxol-5-ol;
6-[(2-Hydroxy-3-methoxyphenyl)(4-morpholinyl)methyl]-1,3-benzodioxol-5-ol;
6-[1-Pyrrolidinyl(2,4,6-trimethoxyphenyl)methyl]-1,3-benzodioxol-5-ol;
6-((4-(Dimethylamino)phenyl)(4-morpholinyl)methyl)-1,3-benzodioxol-5-ol;
6-[(2-Methoxyphenyl)(4-morpholinyl)methyl]-1,3-benzodioxol-5-ol;
6-{piperidino[4-(trifluoromethyl)phenyl]methyl}-1,3-benzodioxol-5-ol;
6-((2,4-Dimethoxyphenyl)-4-morpholinylmethyl)-1,3-benzodioxol-5-ol;
2-[1,3-Benzodioxol-5-yl(4-morpholinyl)methyl]-4-methylphenol;
6-[(2,3-Dimethoxyphenyl)(4-morpholinyl)methyl]-1,3-benzodioxol-5-ol;
6-{morpholino[4-(trifluoromethyl)phenyl]methyl}-1,3-benzodioxol-5-ol;
6-[1,3-Benzodioxol-5-yl(4-morpholinyl)methyl]-1,3-benzodioxol-5-ol;
6-{[4-Hydroxy-3,5-bis(2-methyl-2-propanyl)phenyl](4-morpholinyl)methyl}-1,3-benzodioxol-5-ol;
6-[4-Morpholinyl(2,3,4-trimethoxyphenyl)methyl]-1,3-benzodioxol-5-ol;
6-[(4-Fluorophenyl)(4-morpholinyl)methyl]-1,3-benzodioxol-5-ol;
6-{[4-(Dimethylamino)phenyl](1-pyrrolidinyl)methyl}-1,3-benzodioxol-5-ol;
6-(3,4,5-Trimethoxybenzyl)-1,3-benzodioxol-5-ol;
6-{[4-(Dimethylamino)phenyl](1-piperidinyl)methyl}-1,3-benzodioxol-5-ol;
6-((2-Hydroxyphenyl)(4-morpholinyl)methyl)-1,3-benzodioxol-5-ol;
6-[(2,3-Dimethoxyphenyl)(1-pyrrolidinyl)methyl]-1,3-benzodioxol-5-ol;
6-[1,3-Benzodioxol-5-yl(4-morpholinyl)methyl]-1,3-benzodioxol-5-ol;
6-[(2-Hydroxy-3-methoxyphenyl)(1-pyrrolidinyl)methyl]-1,3-benzodioxol-5-ol;
6-[(2,4-Dimethoxyphenyl)(1-pyrrolidinyl)methyl]-1,3-benzodioxol-5-ol;
6-[1,3-Benzodioxol-5-yl(1-pyrrolidinyl)methyl]-1,3-benzodioxol-5-ol;
6-[(2-Methoxyphenyl)(1-pyrrolidinyl)methyl]-1,3-benzodioxol-5-ol;
6-[(2,4-Dimethoxyphenyl)(1-piperidinyl)methyl]-1,3-benzodioxol-5-ol; and
6-(1-Pyrrolidinyl(3,4,5-trimethoxyphenyl)methyl)-1,3-benzodioxol-5-ol.

5. The method of claim 1, wherein the compound is selected from the group consisting of:
6-{[4-Hydroxy-3,5-bis(2-methyl-2-propanyl)phenyl](4-morpholinyl)methyl}-1,3-benzodioxol-5-ol; and 6-(1-Pyrrolidinyl(3,4,5-trimethoxyphenyl)methyl)-1,3-benzodioxol-5-ol.

6. The method of claim 1, further comprising administering to the subject a second anti-cancer agent.

7. The method of claim 6, wherein the second anti-cancer agent is selected from the group consisting of cytarabine, cladribine, fludarabine, topotecan, doxorubicin, daunorubicin, epirubicin, idarubicin, decitabine, azacitidine, all-trans-retinoic acid, arsenic trioxide, gemtuzumab ozogamicin, midostaurin, nelarabine, clofarabine, dasatinib, imatinib, ponatinib, JQ1, methotrexate, corticosteroids, histamine dihydrochloride, interleukin 2, and combinations thereof.

8. The method of claim 6 wherein the second anti-cancer agent is co-administered with the compound according to Formula I.

9. A method for selectively suppressing transcription of TET1 and/or reducing a level of 5-hydroxymethylcytosine in a subject, the method comprising administering to the subject an effective amount of a compound, or a pharmaceutically acceptable salt thereof, wherein the compound is selected from the group consisting of:
6-{[4-Hydroxy-3,5-bis(2-methyl-2-propanyl)phenyl](4-morpholinyl)methyl}-1,3-benzodioxol-5-ol; and 6-(1-Pyrrolidinyl(3,4,5-trimethoxyphenyl)methyl)-1,3-benzodioxol-5-ol.

* * * * *

SEQUENCE LISTING

```
<160> NUMBER OF SEQ ID NOS: 12

<210> SEQ ID NO 1
<211> LENGTH: 24
<212> TYPE: DNA
<213> ORGANISM: Homo sapiens

<400> SEQUENCE: 1
ttccctgaac agcttttaca tgtg                                        24

<210> SEQ ID NO 2
<211> LENGTH: 9
<212> TYPE: DNA
<213> ORGANISM: Homo sapiens
<220> FEATURE:
<221> NAME/KEY: misc_feature
<222> LOCATION: (4)..(6)
<223> OTHER INFORMATION: n is a, c, g, or t

<400> SEQUENCE: 2 ttcnnngaa                                                          9

<210> SEQ ID NO 3
<211> LENGTH: 24
<212> TYPE: DNA
<213> ORGANISM: Homo sapiens

<400> SEQUENCE: 3
actttgacct cccaaagtgc tgga                                        24

<210> SEQ ID NO 4
<211> LENGTH: 24
<212> TYPE: DNA
<213> ORGANISM: Homo sapiens

<400> SEQUENCE: 4
acctgagtga tgctgagact tcct                                        24

<210> SEQ ID NO 5
<211> LENGTH: 22
<212> TYPE: DNA
<213> ORGANISM: Homo sapiens
```

```
<400> SEQUENCE: 5
tttgggaacc gactcctcac ct                                                   22

<210> SEQ ID NO 6
<211> LENGTH: 22
<212> TYPE: DNA
<213> ORGANISM: Homo sapiens

<400> SEQUENCE: 6
tcgggcaaac tttccaactc gc                                                   22

<210> SEQ ID NO 7
<211> LENGTH: 24
<212> TYPE: DNA
<213> ORGANISM: Homo sapiens

<400> SEQUENCE: 7
acgctgggca tttctgatcc acta                                                 24

<210> SEQ ID NO 8
<211> LENGTH: 24
<212> TYPE: DNA
<213> ORGANISM: Homo sapiens

<400> SEQUENCE: 8
tattgtgcag ctcgtttagt gccc                                                 24

<210> SEQ ID NO 9
<211> LENGTH: 17
<212> TYPE: DNA
<213> ORGANISM: Homo sapiens

<400> SEQUENCE: 9
ccatctcccg acacaca                                                         17

<210> SEQ ID NO 10
<211> LENGTH: 18
<212> TYPE: DNA
<213> ORGANISM: Homo sapiens

<400> SEQUENCE: 10
ttggcagtga ccttgaga                                                        18

<210> SEQ ID NO 11
<211> LENGTH: 25
<212> TYPE: DNA
<213> ORGANISM: Homo sapiens

<400> SEQUENCE: 11
ccggtaggcg tcctccgcga cccgc                                                25

<210> SEQ ID NO 12
<211> LENGTH: 25
<212> TYPE: DNA
<213> ORGANISM: Homo sapiens

<400> SEQUENCE: 12
gcgggtcgcg gaggacgcct accgg                                                25
```